US007348181B2

(12) United States Patent
Walt et al.

(10) Patent No.: US 7,348,181 B2
(45) Date of Patent: *Mar. 25, 2008

(54) SELF-ENCODING SENSOR WITH MICROSPHERES

(75) Inventors: David R. Walt, Lexington, MA (US); Todd A. Dickinson, San Diego, CA (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/287,573

(22) Filed: Apr. 6, 1999

(65) Prior Publication Data

US 2001/0029049 A1    Oct. 11, 2001

Related U.S. Application Data

(63) Continuation-in-part of application No. PCT/US98/21193, filed on Oct. 6, 1998, and a continuation-in-part of application No. 08/944,850, filed on Oct. 6, 1997, now Pat. No. 7,115,884.

(51) Int. Cl.
G01N 21/76 (2006.01)

(52) U.S. Cl. .......................... 436/172; 435/6; 435/7.1; 435/287.2; 435/288.4; 436/19; 436/164; 436/171; 436/518; 422/55; 422/68.1; 422/82.05; 422/82.06; 422/82.07; 422/82.08; 422/91

(58) Field of Classification Search ............... 422/55, 422/68.1, 82.05, 82.06, 82.07, 82.08, 82.09, 422/91; 435/7.92, 6, 808, 91.2, 7.1, 91, 287.2, 435/288.4; 436/164, 171, 172, 7.24, 536, 436/518, 19; 385/12, 38, 147
See application file for complete search history.

(56) References Cited

U.S. PATENT DOCUMENTS

| 4,200,110 A | 4/1980 | Peterson et al. |
| 4,499,052 A | 2/1985 | Fulwyler |
| 4,682,895 A | 7/1987 | Costello |
| 4,785,814 A | 11/1988 | Kane |
| 4,822,746 A | 4/1989 | Walt |
| 4,824,789 A | 4/1989 | Yafuso et al. |
| 4,999,306 A | 3/1991 | Yafuso et al. |
| 5,002,867 A | 3/1991 | Macevicz |
| 5,028,545 A | 7/1991 | Soini |
| 5,105,305 A | 4/1992 | Betzig et al. |
| 5,114,864 A | 5/1992 | Walt |
| 5,132,242 A | 7/1992 | Cheung |
| 5,143,853 A | 9/1992 | Walt |
| 5,194,300 A | 3/1993 | Cheung |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,302,509 A | 4/1994 | Cheeseman |
| 5,308,771 A | 5/1994 | Zhou et al. |
| 5,320,814 A | 6/1994 | Walt et al. |
| 5,357,590 A | 10/1994 | Auracher |
| 5,380,489 A | 1/1995 | Sutton et al. |
| 5,435,724 A | 7/1995 | Goodman et al. |
| 5,474,895 A | 12/1995 | Ishii et al. |
| 5,481,629 A | 1/1996 | Tabuchi |
| 5,494,798 A | 2/1996 | Gerdt et al. |
| 5,494,810 A | 2/1996 | Barany et al. |
| 5,496,997 A | 3/1996 | Pope |
| 5,512,490 A | 4/1996 | Walt et al. |
| 5,516,635 A | 5/1996 | Ekins et al. |
| 5,518,883 A | 5/1996 | Soini |
| 5,565,324 A | 10/1996 | Still et al. |
| 5,573,909 A | 11/1996 | Singer et al. |
| 5,575,849 A | 11/1996 | Honda et al. |
| 5,599,668 A * | 2/1997 | Stimpson et al. ............. 435/6 |
| 5,633,972 A | 5/1997 | Walt et al. |
| 5,639,603 A | 6/1997 | Dower et al. |
| 5,656,241 A | 8/1997 | Seifert et al. |
| 5,679,524 A | 10/1997 | Nikiforov et al. |
| 5,690,894 A | 11/1997 | Pinkel et al. |
| 5,739,000 A * | 4/1998 | Bierre et al. ............. 435/7.24 |

(Continued)

FOREIGN PATENT DOCUMENTS

EP        0269764        6/1988

(Continued)

OTHER PUBLICATIONS

Sadana et al., Antigen-antibody diffusion-limited binding kinetics for biosensors: A fractal analysis Sensors and Actuators B-Chemical, (Jun. 1996) vol. 32, No. 3, pp. 195-201.*

(Continued)

*Primary Examiner*—Gailene Rio Gabel
(74) *Attorney, Agent, or Firm*—Knobbe, Martens, Olson and Bear, LLP

(57) ABSTRACT

A microsphere-based analytic chemistry system is disclosed in which self-encoding microspheres having distinct characteristic optical response signatures to specific target analytes may be mixed together while the ability is retained to identify the sensor type and location of each sensor in a random dispersion of large numbers of such sensors in a sensor array using an optically interrogatable encoding scheme. An optical fiber bundle sensor is also disclosed in which individual microsphere sensors are disposed in microwells at a distal end of the fiber bundle and are optically coupled to discrete fibers or groups of fibers within the bundle. The identities of the individual sensors in the array are self-encoded by exposing the array to a reference analyte while illuminating the array with excitation light energy. A single sensor array may carry thousands of discrete sensing elements whose combined signal provides for substantial improvements in sensor detection limits, response times and signal-to-noise ratios.

31 Claims, 26 Drawing Sheets

U.S. PATENT DOCUMENTS

| | | | |
|---|---|---|---|
| 5,814,524 A | 9/1998 | Walt et al. | |
| 5,830,711 A | 11/1998 | Barany et al. | |
| 5,837,196 A * | 11/1998 | Pinkel et al. | 422/55 |
| 5,840,256 A | 11/1998 | Demers et al. | |
| 5,854,684 A | 12/1998 | Stabile et al. | |
| 5,856,083 A | 1/1999 | Chelsky et al. | |
| 5,858,659 A | 1/1999 | Sapolsky et al. | |
| 5,858,732 A | 1/1999 | Solomon et al. | |
| 5,863,708 A | 1/1999 | Zanzucchi et al. | |
| 5,866,331 A | 2/1999 | Singer et al. | |
| 5,888,723 A | 3/1999 | Sutton et al. | |
| 5,900,481 A | 5/1999 | Lough et al. | |
| 6,013,456 A | 1/2000 | Akhavan-Tafti | |
| 6,023,540 A * | 2/2000 | Walt et al. | 385/12 |
| 6,027,889 A | 2/2000 | Barany et al. | |
| 6,051,380 A | 4/2000 | Sosnowski et al. | |
| 6,054,564 A | 4/2000 | Barany et al. | |
| 6,083,763 A | 7/2000 | Balch | |
| 6,110,678 A | 8/2000 | Weisburg et al. | |
| 6,172,218 B1 | 1/2001 | Brenner | |
| 6,251,639 B1 | 6/2001 | Kurn | |
| 6,268,148 B1 | 7/2001 | Barany et al. | |
| 6,300,063 B1 | 10/2001 | Lipshutz et al. | |
| 6,309,822 B1 | 10/2001 | Fodor et al. | |
| 6,344,316 B1 | 2/2002 | Lockhart et al. | |
| 6,468,476 B1 | 10/2002 | Friend et al. | |

FOREIGN PATENT DOCUMENTS

| | | |
|---|---|---|
| EP | 0 392 546 | 10/1990 |
| EP | 0478 319 | 4/1992 |
| EP | 0 723 146 | 7/1996 |
| GB | 2 294 319 | 4/1996 |
| WO | 89/11101 | 11/1989 |
| WO | WO91/02975 | 3/1991 |
| WO | 93/02360 | 2/1993 |
| WO | WO 93/25563 A1 | 12/1993 |
| WO | 94/12863 | 6/1994 |
| WO | WO95/11454 | 4/1995 |
| WO | 96/03212 | 2/1996 |
| WO | WO 96/28538 | 9/1996 |
| WO | 97/12030 | 4/1997 |
| WO | 97/14028 | 4/1997 |
| WO | 97/14928 | 4/1997 |
| WO | WO 97/31256 A3 | 8/1997 |
| WO | 97/40385 | 10/1997 |
| WO | WO 98/13523 A1 | 4/1998 |
| WO | 98/40726 | 9/1998 |
| WO | 98/50782 | 11/1998 |
| WO | 98/53093 | 11/1998 |
| WO | 98/53300 | 11/1998 |
| WO | 99/18434 | 4/1999 |
| WO | WO99/54724 | 10/1999 |
| WO | WO 99/60170 A1 | 11/1999 |
| WO | WO99/60450 | 11/1999 |
| WO | 99/67414 | 12/1999 |
| WO | WO 99/67641 A2 | 12/1999 |
| WO | 00/04372 | 1/2000 |
| WO | WO 00/16101 A2 | 3/2000 |
| WO | WO 99/13004 A3 | 3/2000 |
| WO | WO00/18962 | 4/2000 |
| WO | WO00/34788 | 6/2000 |
| WO | WO00/39587 | 7/2000 |
| WO | WO 00/39587 A1 | 7/2000 |
| WO | WO00/47607 | 8/2000 |
| WO | WO 00/47996 A2 | 8/2000 |
| WO | 00/48000 | 9/2000 |
| WO | WO 00/58516 A2 | 10/2000 |
| WO | WO00/60332 | 10/2000 |
| WO | WO 00/63437 A2 | 10/2000 |
| WO | WO 00/71243 A1 | 11/2000 |
| WO | WO 00/71995 A2 | 11/2000 |
| WO | WO 00/75373 A2 | 12/2000 |
| WO | WO01/46675 | 6/2001 |
| WO | WO03/002979 | 1/2003 |

OTHER PUBLICATIONS

U.S. Appl. No. 08/818,199, filed Mar. 1997, Walt et al.

U.S. Appl. No. 08/851,203, filed May 1997, Walt et al.

Anonymous, "Fluorescent Microspheres," Tech. Note 19, Bang Laboratories, (Fishers, In) Feb. 1997.

Anonymous, "Microsphere Selection Guide," Bangs Laboratories, (Fisher, In) Sep. 1998.

Bangs, L.B., "Immunological Applications of Microspheres," The Latex Course, Bangs Laboratories (Carmel, IN) Apr. 1996.

Healey, B., et al. "Development of a Penicillin Biosensor Using a Single Optical Imaging Fiber," SPIE 2388:568-573 (1995).

Healey, B., et al. "Improved Fiber-Optic Chemical Sensor for Penicillin," Analytical Chemistry, 67(24): 4471-4476 (1995).

Michael, K., et al. "Fabrication of Micro- and Nanostructures Using Optical Imaging Fibers and Their Use as Chemical Sensors," Electrochemical Society Proceedings 97-5: 153-158 (1997).

Pantoano, P. et al., "Ordered nanowell Arrays," Chem. Mater., 8:2832-2835 (1996).

Peterson J. et al., "Fiber Optic pH Probe for Physiological Use," Anal. Chem., 52:864-869 (1980).

Pope, E. "Fiber Optic Chemical Microsensors Employing Optically Active Silica Microspehres," SPIE, 2388:245-256 (1995).

Walt, D. "Fiber-Optic Sensors for Continuous Clinical Monitoring," Proceedings of the IEEE, 80(6):903-911 (1992).

Ferguson, J. et al. "A Fiber-Optic DNA BiosensorMicroarray for the Analysis of Gene Expression," Nature Biotechnology, 14:1681-1684 (1996).

Healey, B. et al. "Fiberoptic DNA Sensor Array Capable of Detecting Point Mutations," Analytical Biochemistry, 251:270-279 (1997).

Piunno, P. et al. "Fiber-Optic DNA Sensor for Fluorometric Nucleic Acid Determination," Anal. Chem. 67:2635-2643 (1995).

Abel, A. et al. "Fiber-Optic Evanescent Wave Biosensor for the Detection of Oligonucleotides," Anal. Chem. 68:2905-2912 (1996).

Strachan, N.J.C. et al. "A Rapid General Method for the Identification of PCR Products Using a Fibre-Optic Biosensor and its Application to the detection of Listeria," Letters in Applied Microbiology, 21:5-9 (1995).

Barnard et al., "A Fibre-Optic Chemical Sensor with Discrete Sensing Sites," Nature, 353:338-340 (Sep. 26, 1991).

Fuh, et al., "Single Fibre Optic Fluorescence pH Probe," Analyst, 112:1159-1163 (1987).

Hirschfeld, et al., "Laser-Fiber-Optic "Optrode" for Real Time In Vivo Blood Carbon Dioxide Level Monitoring," Journal of Lightwave Technology, LT-5(7):1027-1033 (Jul. 1987).

Mignani, et al., "In-Vivo Biomedical Monitoring by Fiber-Optic Systems," Journal of Lightwave Technology, 13(7):1396-1406 (1995).

Peterson, et al., "Fiber-Optic Sensors for Biomedical Applications," Science, 13:123-127 (1984).

Drmanac, R. et al., "Sequencing by Oligonucleotide Hybridization: A Promising Framework in Decoding of the Genome Program," The First International Conference on Electrophoresis, Supercomputing and the Human Genome, Proceedings os th Apr. 10-13, 1990 Conference at Florida State University. Ed. C. Cantor and H. Lim.

Drmanac, R. et al., "Prospects for a Miniaturized, Simplified and Frugal Human Genome Project," Scientia Yugoslavica, 16(1-2):97-107 (1990).

Drmanac, R. et al., "Sequencing by Hybridization (SBH) with Oligonucleotide Probes as an Integral Approach for the Analysis of Complex Genomes," International Journal of Genome Research, 1(1):59-79 (1992).

Drmanac, R. et al., "Sequencing by Hybridization," Automated DNA Sequencing and Analysis, ed. M. Adams, C. Fields and J. Venter. (1994).

Czarnik, "Illuminating the SNP Genomic Code," Modern Drug Discovery, 1(2): 49-55 (1998).

Walt, D. "Fiber Optic Imaging Sensors," Accounts of Chemical Research, 31(5): 267-278 (1998).

Lyamichev et al., "Polymorphism identification and quantitative detection of genomic DNA by invasive cleavage of oligonucleotide probes," Nature Biotechnolgoy, 17:292-296 (1999).

Shoemaker et al., "Quantitative phenotypic analysis of yeast deletion mutants using a highly parallel molecular bar-coding strategy," Nature Genetics, 14:450-456 (1996).

Chen et al., "A Microsphere-Based Assay for Multiplexed Single Nucleotide Polymorphism Analysis Using Single Base Chain Extension," Genome Research, 10(4):549-557 (2000).

Iannone et al., "Multiplexed Single Nucleotide Polymorphism Genotyping by Oligonucleotide Ligation and Flow Cytometry," Cytometry, 39:131-140 (2000).

Michael et al., "Making Sensors out of Disarray: Optical Sensor Microarrays," Proc. SPIE, 3270: 34-41 (1998).

Michael et al., "Randomly Ordered Addressable High-Density Optical Sensor Arrays," Anal. Chem. 70(7): 1242-1248 (Apr. 1998).

* cited by examiner

FIG._3

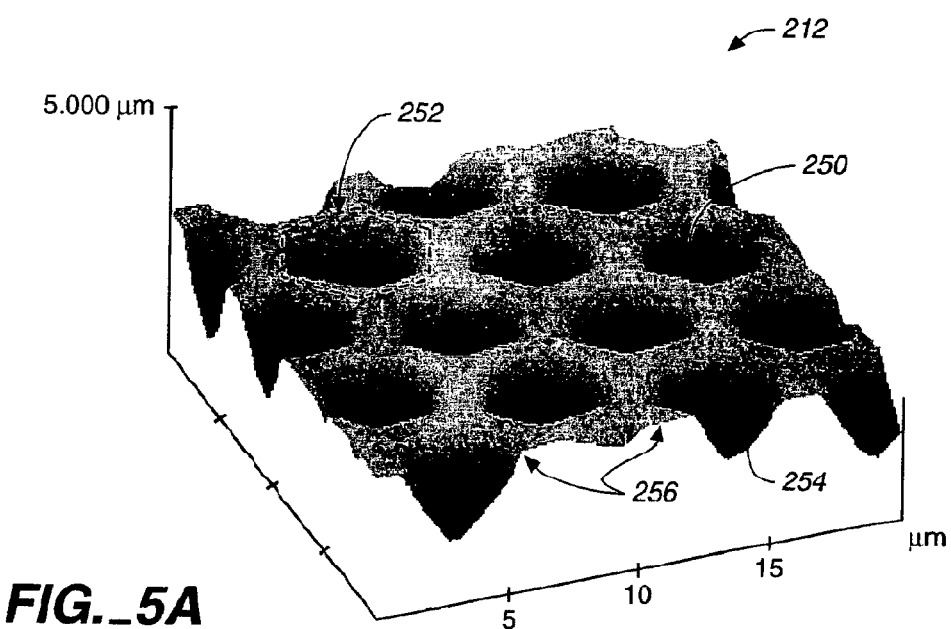
FIG._5A
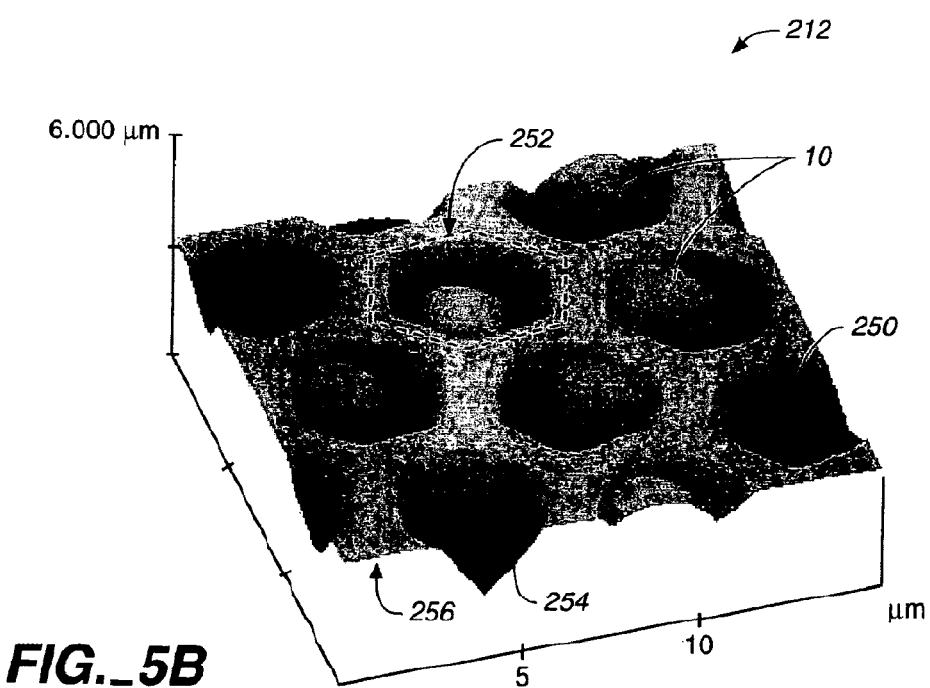
FIG._5B

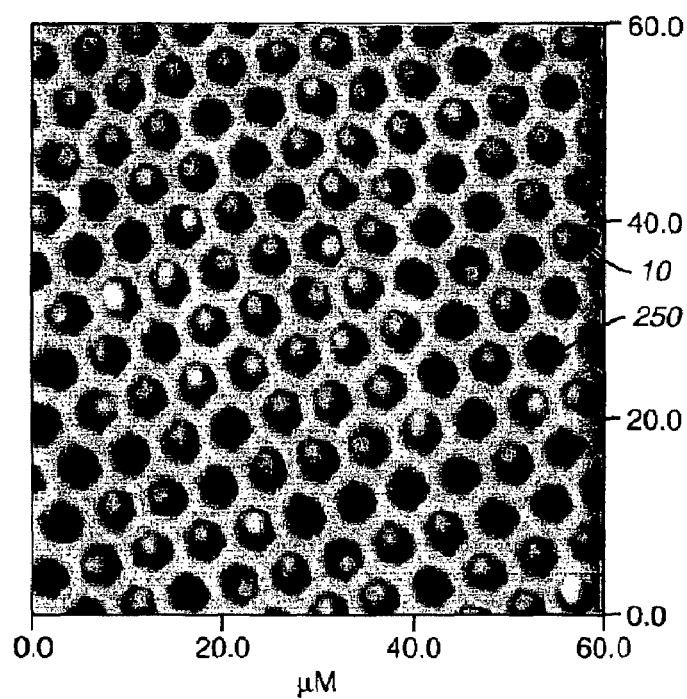
FIG._6A
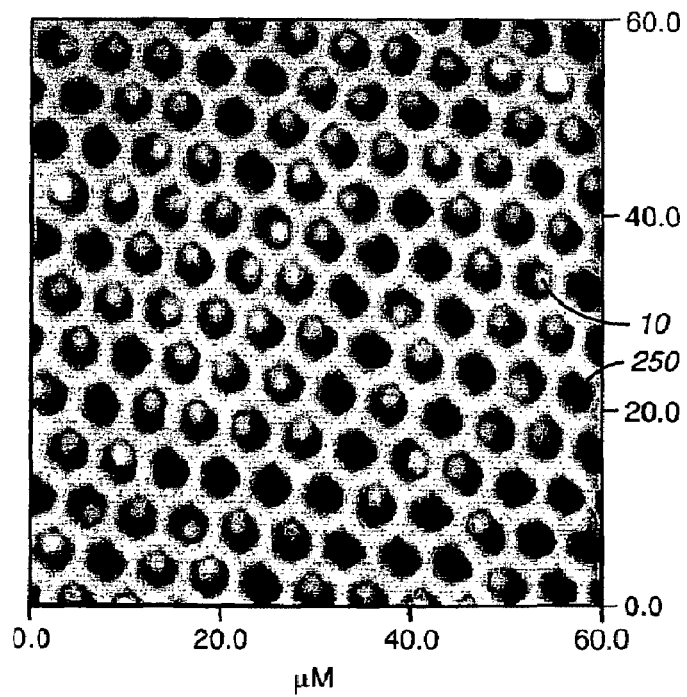
FIG._6B

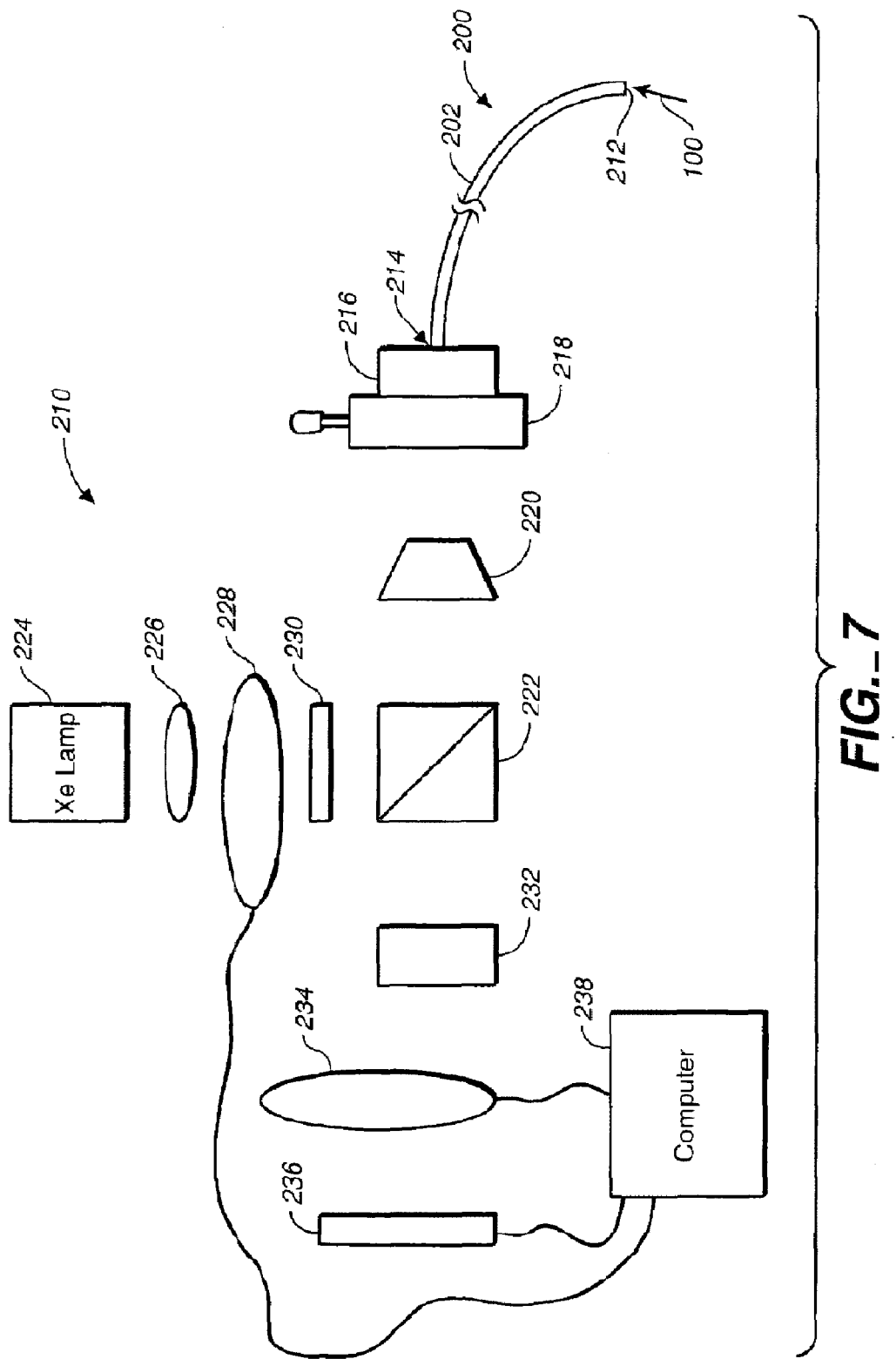
FIG._7

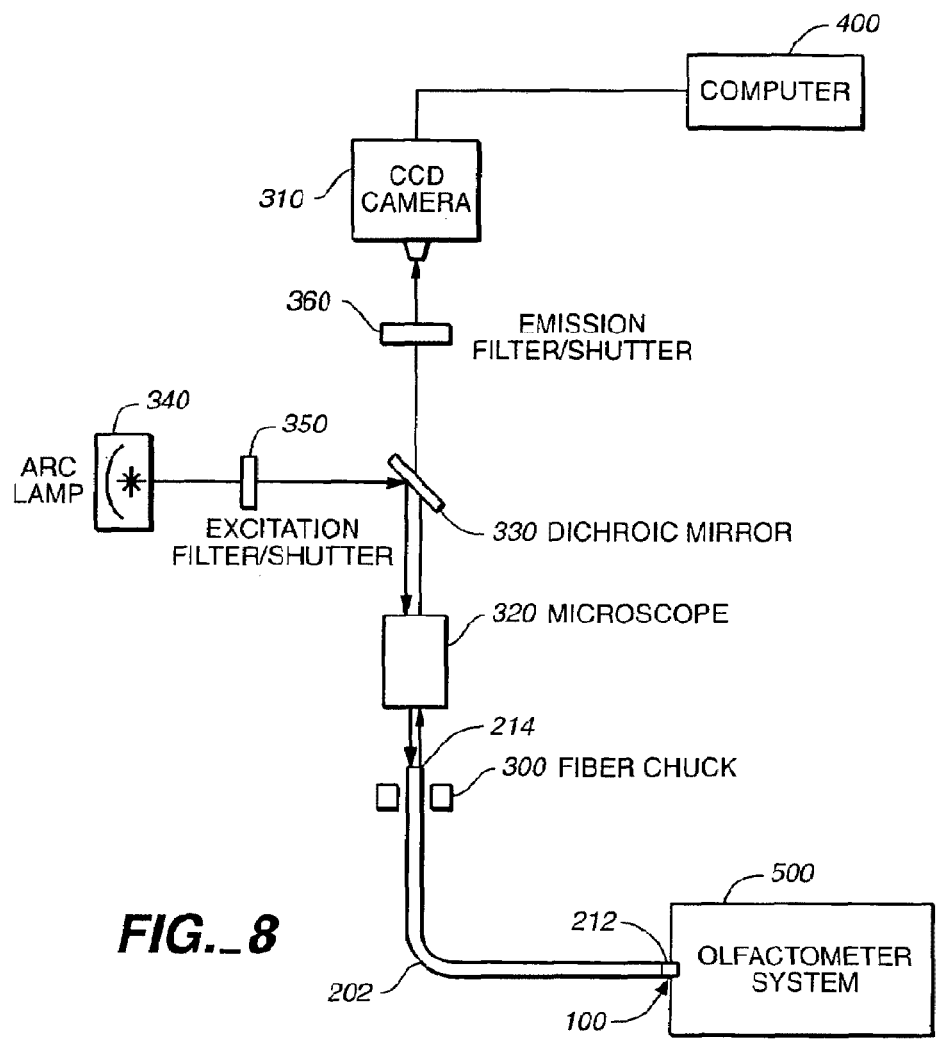
FIG._8

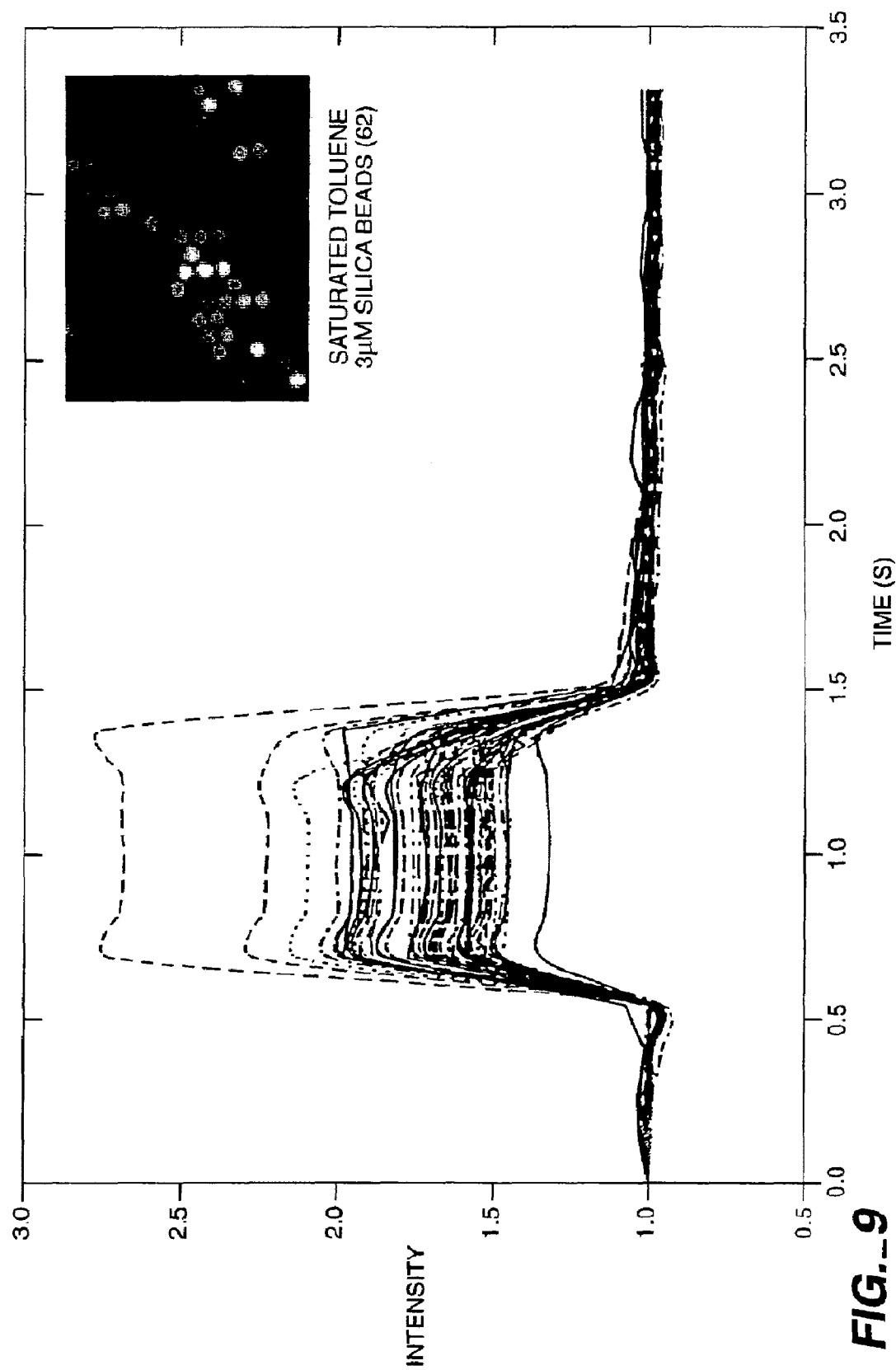
FIG._9

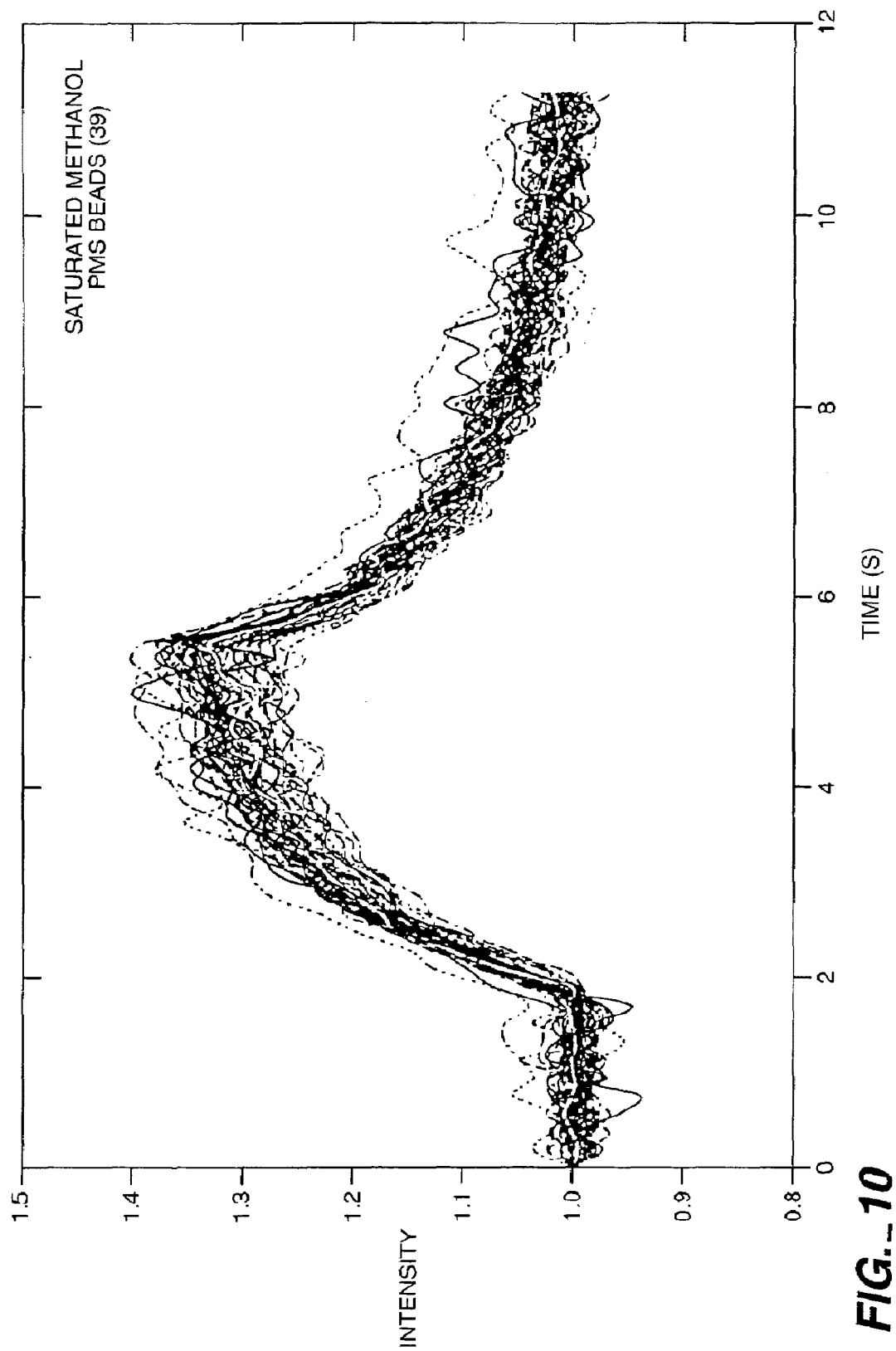
FIG._10

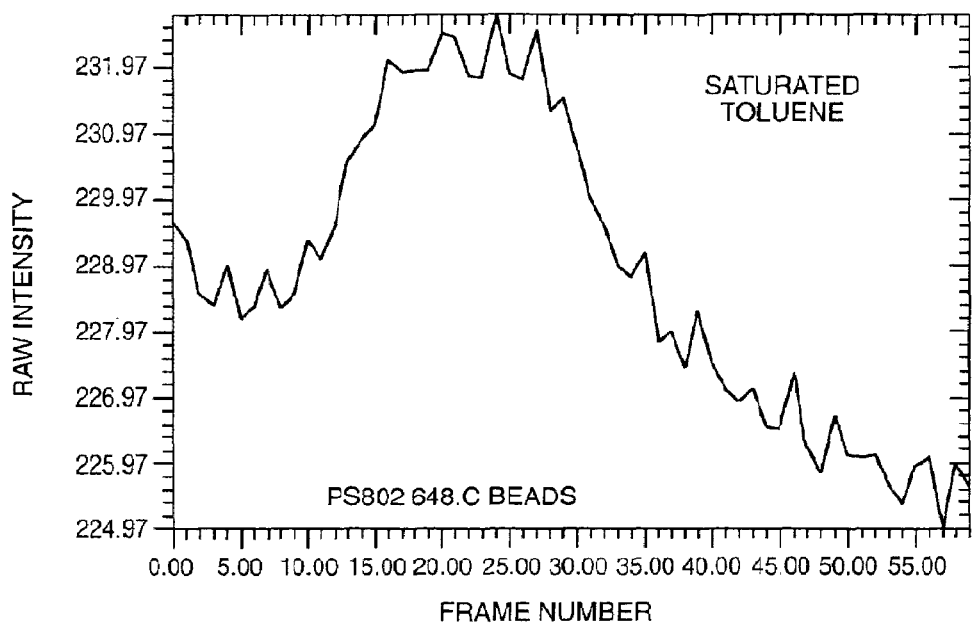
FIG._11A
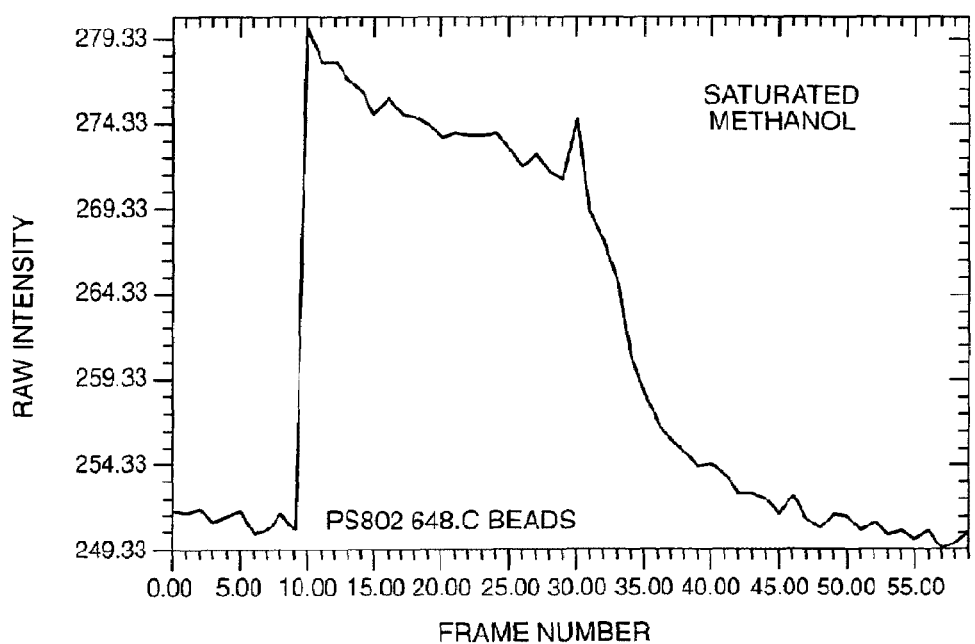
FIG._11B

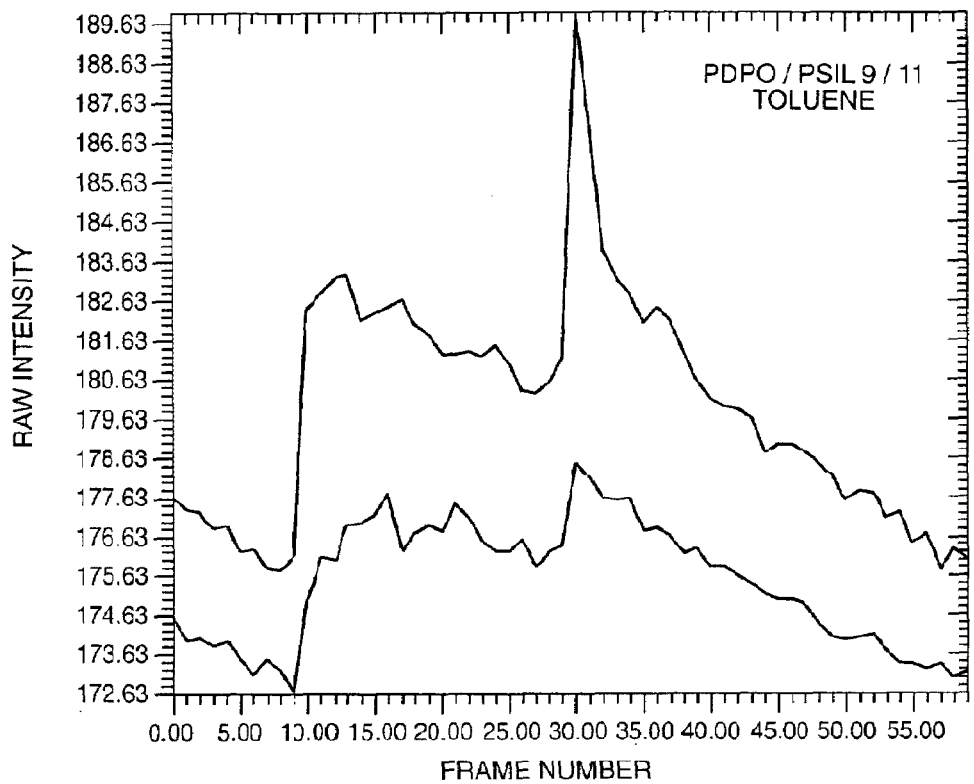
FIG._12A
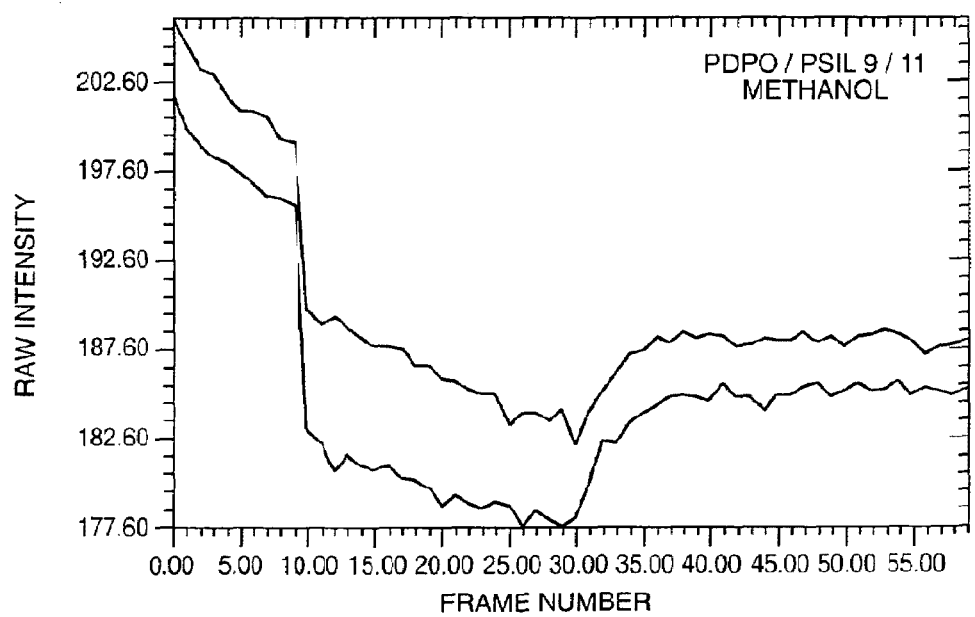
FIG._12B

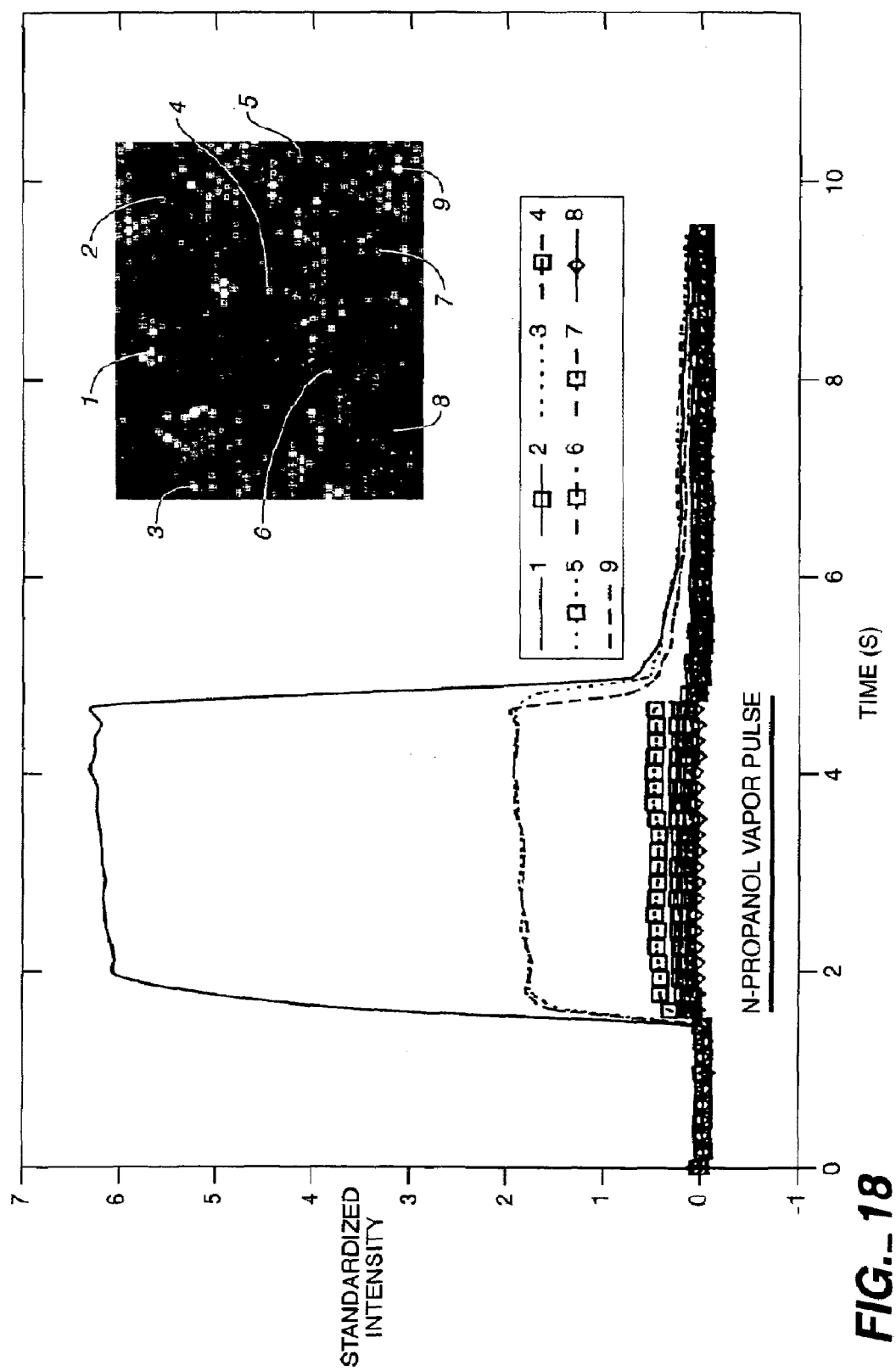
FIG._18

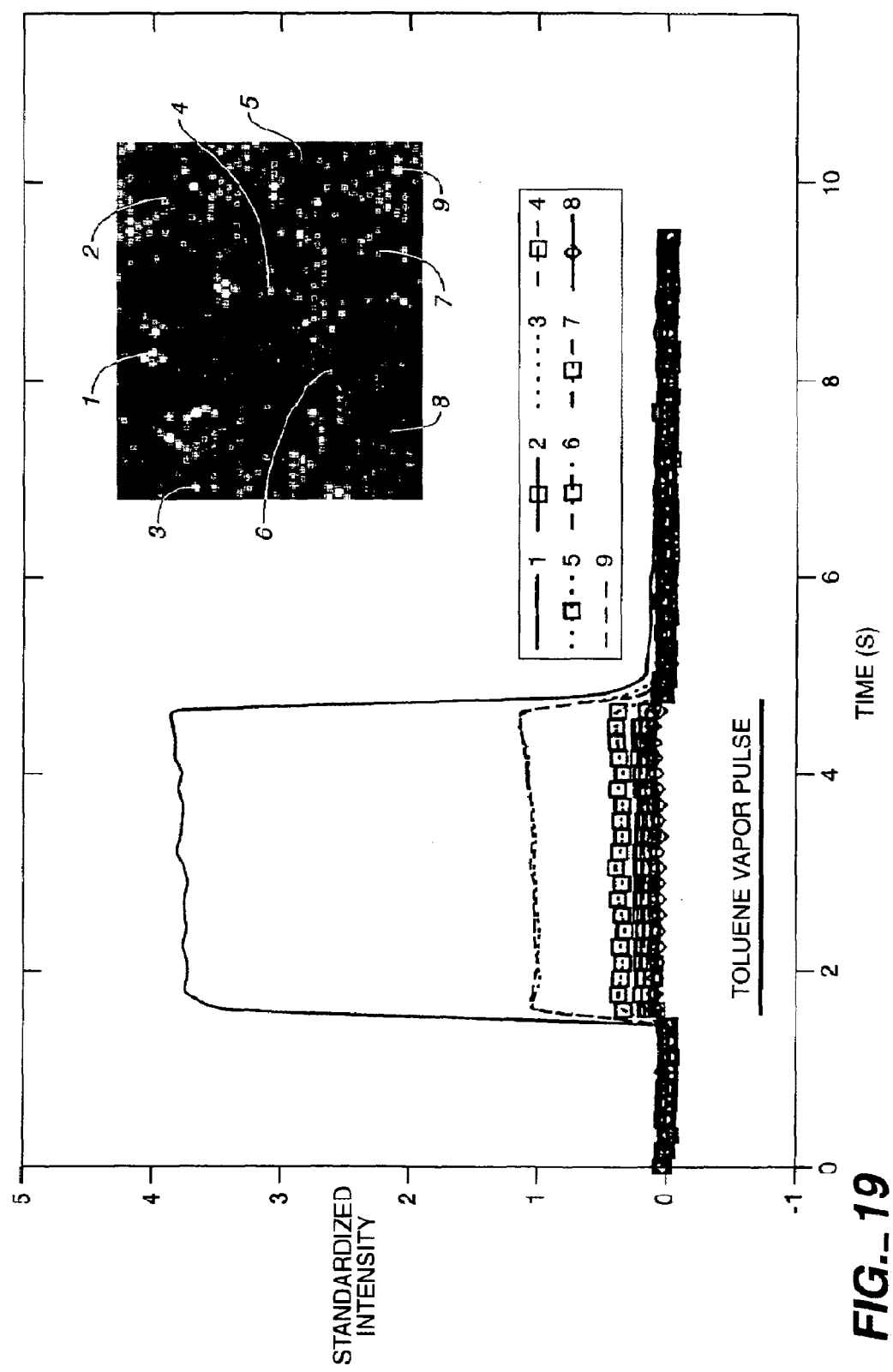
FIG._19

PS802 648.C
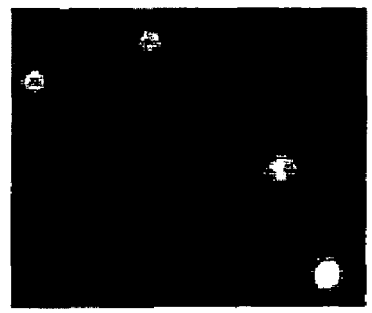
AIR
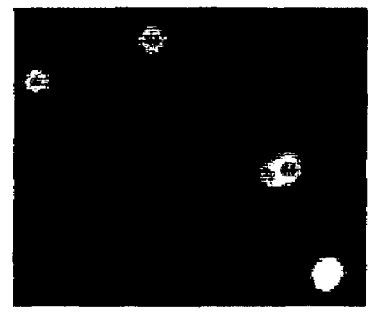
TOLUENE
POLY METHYL STYRENE /
2% DIVINYL BENZENE
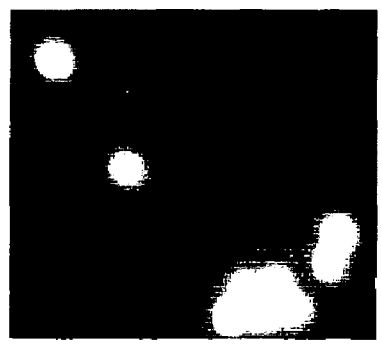
AIR
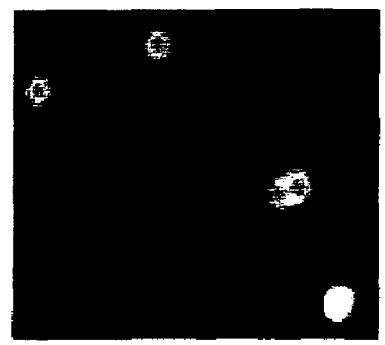
TOLUENE
POLY METHYL STYRENE
AIR
TOLUENE
*FIG._20*

1) β-glo (segment of human β-globin)[26]
TCA ACT TCA TCC ACG TTC ACC (SEQ ID NO: 12)
2) IFNG (interferon gamma 1)[26]
IFNG TGG GTT CTC TTG GCT GTT ACT (SEQ ID NO: 13)
3) IL2 (interleukin-2)[26]
TA CAA GAA TCC CAA ACT CAC CAG (SEQ ID NO: 14)
4) IL4 (interleukin-4)[26]
CC AAC TGC TTC CCC CTC TGT (SEQ ID NO: 15)
5) IL6 (interleukin-6)[26]
GT TGG GTC AGG GGT GGT TAT T (SEQ ID NO: 16)
6) K-ras WT[27]
GGA GCT GGT GGC GTA (SEQ ID NO: 17)
7) H-ras WT[27]
CCG GCG GTG T (SEQ ID NO: 18)
8) CFTR (cystic fibrosis exon 11)[13]
CAT TAT ACT TGT AGA G (SEQ ID NO: 19)
9) R553X (cystic fibrosis exon 10)[13]
TGT AGA ATT ATC TTC (SEQ ID NO: 20)
10) PAN132[16] (human peripheral lymphocyte)
CCT CTA TAC TTT AAC GTC AAG (SEQ ID NO: 21)
11) Scherm-2[16]
AAG TTT AAC CTA TAC CCT GTC (SEQ ID NO: 22)
12) Hakala-1[20]
CCT ATG ATG AAT ATA G (SEQ ID NO: 23)
13) Hakala-2[26]
AAT ATG ATA ATG GCC T (SEQ ID NO: 24)
14) complement to probe 1
TG AAC GTG GAT GAA GTT G (SEQ ID NO: 6)
15) complement to probe 2
AG TAA CAG CCA AGA GAA CCC AAA (SEQ ID NO: 7)
16) complement to probe 3
CT GGT GAG TTT GGG ATT CTT GTA (SEQ ID NO: 8)
17) complement to probe 4
AC AGA GGG GGA AGC AGT TGG (SEQ ID NO: 9)
18) complement to probe 5
AA TAA CCA CCC CTG ACC CAA C (SEQ ID NO: 10)
19) complement to probe 6
TAC GCC ACC AGC TCC (SEQ ID NO: 25)
20) complement to probe 7
ACA CCG CCG G (SEQ ID NO: 26)
21) complement to probe 8
CTC TAC AAG TAT AAT G (SEQ ID NO: 27)
22) complement to probe 9
GAA GAT GTT AAA GTA TAG AGG (SEQ ID NO: 28)
23) complement to probe 10
CTA GAC GTT AAA GTA TAG AGG (SEQ ID NO: 29)
24) complement to probe 12
CTA TAT TCA TCA TAG G (SEQ ID NO: 30)
25) complement to probe 13
AGG CCA TTA TCA TAT T (SEQ ID NO: 31)

FIG. 21

| Probe | [Cy5] | [Tamra] | [Eu-dye] | Correct Target Identification |
|---|---|---|---|---|
| HWt | 1 | | 0.1 | 93% |
| Bglo | 0.5 | | 0.05 | 88% |
| KWt | 0.5 | | 0.005 | 91% |
| IL6 | 0.1 | | 0.1 | 96% |
| IL4 | 0.1 | | 0.005 | 95% |
| IFNG | | 0.4 | 0.005 | 95% |
| IL2 | | 0.04 | 0.05 | 98% |

FIG. 22

| Target Identity | No. of beads in analysis section | [Cy5] | [Tamra] | [Eu-dye] | Correct Target Identification |
|---|---|---|---|---|---|
| 2 | 19 | | 3 | 0.5 | 89% |
| 4 | 15 | 0.01 | 0.1 | 0.1 | 87% |
| 5 | 13 | | 0.1 | 0.1 | 100% |
| 9 | 5 | 0.01 | | | 100% |
| 10 | 14 | | | 0.001 | 86% |
| 11 | 12 | | 0.1 | | 92% |
| 15 | 8 | 0.01 | 0.1 | | 100% |
| 16 | 24 | 0.1 | | | 92% |
| 21 | 21 | 0.1 | 3 | | 95% |
| 24 | 16 | 0.3 | 3 | | 94% |

FIG. 23

| Sequences | Number of microspheres | Mean background ± s.d. | Fluorescence after hybridization | Signal |
|---|---|---|---|---|
| Complementary target | 10 | 997.01 ± 4.62 | 1036.94 | 39.93 |
| | 10 | 1003.46 ± 6.05 | 1035.83 | 32.37 |
| | 10 | 957.44 ± 5.59 | 985.25 | 27.81 |
| | 100 | 977.88 ± 3.21 | 1010.74 | 32.86 |
| Poly A | 10 | 1213.79 ± 6.33 | 1221.61 | (7.81) |
| | 10 | 1185.25 ± 9.39 | 1194.74 | (9.49) |
| | 10 | 1190.20 ± 4.85 | 1198.35 | (8.15) |
| | 100 | 1190.67 ± 4.05 | 1199.81 | (9.14) |
| IL2 | 10 | 1090.58 ± 4.97 | 1096.11 | (5.53) |
| | 10 | 1120.62 ± 3.09 | 1113.88 | (-6.74) |
| | 10 | 1101.82 ± 5.51 | 1091.28 | (-10.55) |
| | 100 | 1104.36 ± 1.40 | 1103.06 | (-1.30) |

FIG. 24

SELF-ENCODING SENSOR WITH MICROSPHERES

RELATED APPLICATIONS

This application is a continuation-in-part application of U.S. application U.S. application Ser. No. 08/944,850, filed Oct. 6, 1997 and PCT application PCT/US98/21193 filed Oct. 6, 1998, the text of which applications is expressly incorporated by reference herein.

STATEMENT REGARDING FEDERALLY SPONSORED RESEARCH

This invention was made with government support under N00014-94-0312 awarded by the Department of the Navy, Office of Naval Research. The government may have certain rights in the invention.

FIELD OF THE INVENTION

The present invention is generally concerned with chemical sensors, sensor arrays and sensing apparatus for the detection of gaseous and liquid analytes. More particularly, the invention is directed to optical chemical sensors and the detection and evaluation of optical data generated by sensing receptor units.

BACKGROUND OF THE INVENTION

The use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in *C.R.C. Critical Reviews In Analytical Chemistry*, Vol. 19, 1988, pp. 135-173; Wolfbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2(4):38 (1987); Walt, et al., "Chemical Sensors and Microinstrumentation", *ACS Symposium Series*, Vol. 403, 1989, p. 252, and Wolfbeis, O. S., *Fiber Optic Chemical Sensors*, Ed. CRC Press, Boca Raton, Fla., 1991, 2nd Volume.

When using an optical fiber in an in vitro/in vivo sensor, one or more light absorbing dyes are located near its distal end. Typically, light from an appropriate source is used to illuminate the dyes through the fiber's proximal end. The light propagates along the length of the optical fiber; and a portion of this propagated light exits the distal end and is absorbed by the dyes. The light absorbing dye may or may not be immobilized; may or may not be directly attached to the optical fiber itself; may or may not be suspended in a fluid sample containing one or more analytes of interest; and may or may not be retainable for subsequent use in a second optical determination.

Once the light has been absorbed by the dye, some light of varying wavelength and intensity returns, conveyed through either the same fiber or collection fiber(s) to a detection system where it is observed and measured. The interactions between the light conveyed by the optical fiber and the properties of the light absorbing dye provide an optical basis for both qualitative and quantitative determinations.

Of the many different classes of light absorbing dyes which conventionally are employed with bundles of fiber strands and optical fibers for different analytical purposes are those more common compositions that emit light after absorption termed "fluorophores" and those which absorb light and internally convert the absorbed light to heat, rather than emit it as light, termed "chromophores."

Fluorescence is a physical phenomenon based upon the ability of some molecules to absorb light (photons) at specified wavelengths and then emit light of a longer wavelength and at a lower energy. Substances able to fluoresce share a number of common characteristics: the ability to absorb light energy at one wavelength; reach an excited energy state; and subsequently emit light at another light wavelength. The absorption and fluorescence emission spectra are individual for each fluorophore and are often graphically represented as two separate curves that are slightly overlapping. The same fluorescence emission spectrum is generally observed irrespective of the wavelength of the exciting light and, accordingly, the wavelength and energy of the exciting light may be varied within limits; but the light emitted by the fluorophore will always provide the same emission spectrum. Finally, the strength of the fluorescence signal may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., *Principles of Fluorescence Spectroscopy*, Plenum Press, New York, 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis, vol.* 77, Wiley & Sons, Inc., 1985; *The Theory of Luminescence*, Stepanov and Gribkovskii, Iliffe Books, Ltd., London, 1968.

Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses. These developments are exemplified by the following publications: Freeman, et al., *Anal Chem.* 53:98 (1983); Lippitsch et al., *Anal. Chem. Acta.* 205:1, (1988); Wolfbeis et al., *Anal Chem.* 60:2028 (1988); Jordan, et al., *Anal. Chem.* 59:437 (1987); Lubbers et al., *Sens. Actuators* 1983; Munkholm et al., *Talanta* 35:109 (1988); Munkholm et al., *Anal Chem.* 58:1427 (1986); Seitz, W. R., *Anal Chem.* 56:16A-34A (1984); Peterson, et al., *Anal Chem.* 52:864 (1980): Saari, et al., *Anal Chem.* 54:821 (1982); Saari, et al., *Anal Chem.* 55:667 (1983); Zhujun et al., *Anal Chem. Acta.* 160:47 (1984); Schwab, et al., *Anal Chem.* 56:2199 (1984); Wolfbeis, O. S., "Fiber Optic Chemical Sensors", Ed. *CRC Press*, Boca Raton, Fla., 1991, 2nd Volume; and Pantano, P., Walt, D. R., *Anal Chem.*, 481A-487A, Vol. 67, (1995).

More recently, fiber optic sensors have been constructed that permit the use of multiple dyes with a single, discrete fiber optic bundle. U.S. Pat. Nos. 5,244,636 and 5,250,264 to Walt, et al disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

Most recently, fiber optic sensors have been employed in arrays of semi-selective chemical sensors and pattern recognition schemes to discriminate and quantify odors. Such approaches have been useful in implementing the principles of biological olfaction in the design of sensing devices or systems. In this field of biomimetry, various technologies have been applied to the sensor transduction mechanism. For example, surface acoustic wave, conducting polymer, metal oxide sensor field-effect transistor (MOSFET), piezoelectric, and quartz crystal microbalance sensor arrays have been pursued.

While such technologies provide inventive approaches utilizing a variety of physical and chemical phenomena to odor sensing, there are a number of limitations to these methods which restrict the efficacy of such devices. Firstly, element-to-element reproducibility both within a single array and between sensor arrays is typically unsatisfactory and thus requires recalibration and network retraining from sensor to sensor. Secondly, most of these methods have a relatively slow response time, frequently requiring several minutes to respond to the presence of an odor. Thirdly, such methods have relatively high detection limits and low sensitivity, typically not functioning at odor levels below 10 ppm. Fourthly, devices which embody such technologies typically require a relatively large inherent size, thereby restricting miniaturization of the sensor array for use in remote sensing applications. Finally, construction of multi-sensor arrays by these methods is complex and involves expensive and tedious preparation and placement of individual sensors within a well-defined array.

Most recently, many of these shortcomings have been overcome through the application of fiber optic sensor arrays in an artificial nose sensor device and system. U.S. Pat. Nos. 5,320,814 and 5,512,490 to Walt, et al., the teachings of each of these patents being incorporated herein by reference, disclose a fiber optic array formed of heterogeneous, semi-selective thin films which function as sensing receptor units and are able to detect a variety of different analytes and ligands using spectral recognition patterns. This technology has been applied to a vapor-sensing system which utilizes arrays of polymer-dye combinations which coat the ends of select optical fibers in a fiber optic bundle. These developments are further described in Dickinson, et al, *Nature* 382:697 (1996) and White, et al, *Anal. Chem.* 68:2191 (1996).

An innovative feature of the four previously referenced patents to Walt, et al., was the placement of multiple chemical functionalities at the end of a single optical fiber bundle sensor. This configuration yielded an analytic chemistry sensor that could be remotely monitored via the typically small bundle. The drawback, however, was the difficulty in applying the various chemistries associated with the chemical functionalities at the sensor's end; the functionalities were built on the sensor's end in a step-wise serial fashion. This was a slow process, and in practice, only tens of functionalities could be applied.

U.S. patent application Ser. No. 08/818,199 to Walt, et al, the teachings of which are incorporated herein by this reference, discloses the use of dye infiltrated polymer microspheres as a substitute for polymer-dye coating layers in optical fiber array sensors. With this approach, a fiber optic bundle serves as a substrate for dye-polymer microsphere array which contains a variety of microsphere bead sensors having different chemical and optical responses to the presence of target analytes. One innovative feature of this invention is in providing for a bead-based analytic chemistry system in which beads or microspheres carrying different chemical functionalities may be mixed together while retaining the ability to identify the functionality of each bead using an optically interrogatable encoding scheme. Additionally, this invention provides for an optical fiber bundle sensor in which the separate beads or microspheres may be optically coupled to discrete fibers or groups of fibers within the bundle. While the innovative features of this invention have separate applications, when implemented together, the invention provides for an optical fiber sensor that can support large numbers, thousands or more, of separate chemical sensor elements, which can be incorporated into a chemical sensor array and chemical analysis system. This approach provides for rapid fabrication and assembly of individual sensors and complex sensor arrays containing a multitude of discrete sensor types. The method also provides for a high degree of reproducibility and conformity within a batch of sensors and sensor arrays. Additional advantages are realized due to the ultrafine sizing available in microspheres. The overall size of the sensor array can be substantially reduced to submillimeter scale. This reduction in scale is particularly advantageous for remote sensing arrays.

While the method of applying microsphere sensor elements in chemical sensor arrays as taught in U.S. patent application Ser. No. 08/818,199 to Walt, et al, has many innovative features, this method has certain limitations. The method requires a complex multi-step bead encoding process to identify the type and location of bead subpopulations used in the sensor array. Beads are encoded by employing combinations of fluorescent dyes in varying ratio. The choice of encoding dyes is limited to those dyes which emit light at different wavelengths upon exposure to excitation light energy. While combinations of dyes in different ratios provide for encoding subpopulations of beads, the number of dye ratios available for encoding beads with a given dye pair or combination is significantly limited due to crowding the emission spectrum from peak overlap. In addition, a separate reporting dye is necessary for obtaining a unique characteristic optical response signature for a target analyte. Thus, the encoding dye choice is further limited by selecting dyes whose emission wavelengths do not overlap or interfere with the reporting dye which is uniquely responsive to the presence of an analyte.

Another limiting feature of this invention is that the process of encoding beads requires a series of measurements which calibrate and train the sensors and the sensor array. Encoding is initially accomplished by first illuminating the beads with excitation light energy and monitoring and recording the type and location of the specific bead subpopulation within the sensor array having a given encoding dye ratio. Next, the array is exposed to an analyte while illuminating the array with excitation light energy in the presence of a reporter dye. Those beads which are responsive to the analyte in the presence of the reporter dye are monitored and mapped on the sensor array. In addition, the characteristic optical response signature is stored in a library. This step is repeated for each analyte of interest in combination with a reporter dye. Once all bead subpopulations are encoded and their response characteristics monitored and recorded, the entire sensor array must be decoded for each analyte by indexing each sensor element with the stored optical response signature for each analyte. This process of decoding individual subpopulations of beads may be require additional steps when a large number of subpopulations are deployed in the array, thereby increasing the training time required for each array.

Other alternative approaches to bead encoding, utilizing molecular tagging, capillary gas chromatography and electron capture detection have been disclosed by Still, et al, *Acc. Chem. Res.* 29:155 (1996). However, such methods are limited in scope and have been applied only to a narrow class of bead materials having specific chemical functionality and molecular tags which are readily analyzable.

SUMMARY OF THE INVENTION

In general, the invention provides self-encoding analytic chemical sensor arrays comprising a substrate with a surface comprising discrete sites and a population of microspheres comprising at least a first and a second subpopulation, wherein each subpopulation comprises at least one reporter dye. The reporting dye has a first characteristic optical response signature when subjected to excitation light energy in the presence of a reference analyte, and the microspheres are distributed on the surface. The beads may further comprise a bioactive agent.

In an additional aspect, the invention provides methods of detecting a target analyte in a sample comprising contacting the sample with an sensor array. The sensor array comprises a substrate with a surface comprising discrete sites and a population of microspheres. The microspheres comprise at least a first and a second subpopulation, each subpopulation comprising a bioactive agent and at least one reporter dye. The reporting dye has a first characteristic optical response signature when subjected to excitation light energy in the presence of a reference analyte and the microspheres are distributed on the surface. The presence or absence (or quantity) of the analyte is then detected. The methods may further comprise identifying the location of each bioactive agent on said substrate by adding the reference analyte.

In a further aspect, the invention provides methods for reducing the signal-to-noise ratio in the characteristic optical response signature of a sensor array having a subpopulations of array elements. The methods comprise decoding the array so as to identify the location of each sensor element within each sensor subpopulation within the array and measuring the characteristic optical response signature of each sensor element in the array. The baseline of the optical response signature is then adjusted for each sensor element in said array, and the baseline-adjusted characteristic optical response signature of all sensor elements within each of the sensor subpopulations is summed. The characteristic optical response signature of each sensor subpopulation as a summation of said baseline-adjusted characteristic optical response signatures of all sensor elements within each of said subpopulations is then reported.

In an additional aspect, the invention provides methods for amplifying the characteristic optical response signature of a sensor array having subpopulations of array elements. The methods comprise decoding the array so as to identify the location of each sensor element within each sensor subpopulation within the array and measuring a characteristic optical response signature of each sensor element in the array. The baseline of the optical response signature for each sensor element in said array is then adjusted. The baseline-adjusted characteristic optical response signature of all sensor elements within each of the sensor subpopulations is then summed and the characteristic optical response signature of each sensor subpopulation as a summation of the baseline-adjusted characteristic optical response signatures of all sensor elements within each of the subpopulations is reported.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 5A and 5B are micrographs illustrating the microwells formed on the distal end of a fiber optic bundle and microspheres inserted in the microwell cavities;

FIGS. 6A and 6B are micrographs showing the array of microspheres in their corresponding microwells prior to and subsequent to agitation by tapping and an air pulse, demonstrating the electrostatic binding of the microspheres in the microwell cavities;

FIG. 7 is a schematic diagram of the inventive fiber optic sensor and associated instrumentation and control system;

FIG. 8 is a schematic diagram illustrating the experimental apparatus used in the optical measurements of Examples 7 through 17;

FIG. 9 illustrates the characteristic optical response signature of porous silica beads infiltrated with Nile Red dye upon exposure to toluene vapor;

FIG. 10 illustrates the characteristic optical response signature of PMS beads infiltrated with Nile Red dye upon exposure to methanol vapor;

FIGS. 11A and 11B illustrate the characteristic optical response signature of a PS802 coated porous silica bead infiltrated with Nile Red dye upon exposure to toluene and methanol vapor;

FIGS. 12A and 12B illustrate the characteristic optical response signature of a PDPO coated porous silica beads infiltrated with Nile Red dye upon exposure to toluene and methanol vapor;

FIG. 18 compares the characteristic optical response signatures of Nile Red infiltrated porous silica and PMS bead subpopulations to n-proponal vapor in a self-encoded fiber optic sensor array of the present invention;

FIG. 19 compares the characteristic optical response signatures of Nile Red infiltrated porous silica and PMS bead subpopulations to toluene vapor in a self-encoded fiber optic sensor array of the present invention;

FIG. 20 compares the differences in bead swelling response of PS802 coated porous silica, poly methyl styrene, and poly methyl styrene/divinyl benzene bead subpopulations upon exposure to toluene vapor;

FIG. 21 depicts sequences used in the array. Each probe has a 5'-($NH_2$—$(CH_2)_6$—) functionality for cyanuric chloride activation and attachment to the microspheres. Each complementary target has a 5'-fluorescein label;

FIG. 22 depicts microsphere code and target identification. The left most column lists the names of the seven probes. The middle columns list the dye concentrations (mM) used to encode the microspheres. Each microsphere type incorporated two encoding dyes for identification of the probe on the bead. The right column lists the percentage of beads that correctly identified the target solution.

FIG. 23 depicts microsphere code and target identification. The left most column lists the numbers from FIG. 21 which identify the probes. The middle columns list the dye concentrations (mM) used to encode the microspheres. Each microsphere type incorporated at least one encoding dye for identification of the probe on the bead. The right column lists the percentage of beads that correctly identified the target solution;

FIG. 24 depicts microsphere array sensitivity. The sensitivity of the system using an intensified CCD camera.

DETAILED DESCRIPTION OF THE PREFERRED EMBODIMENTS

Figure 1:
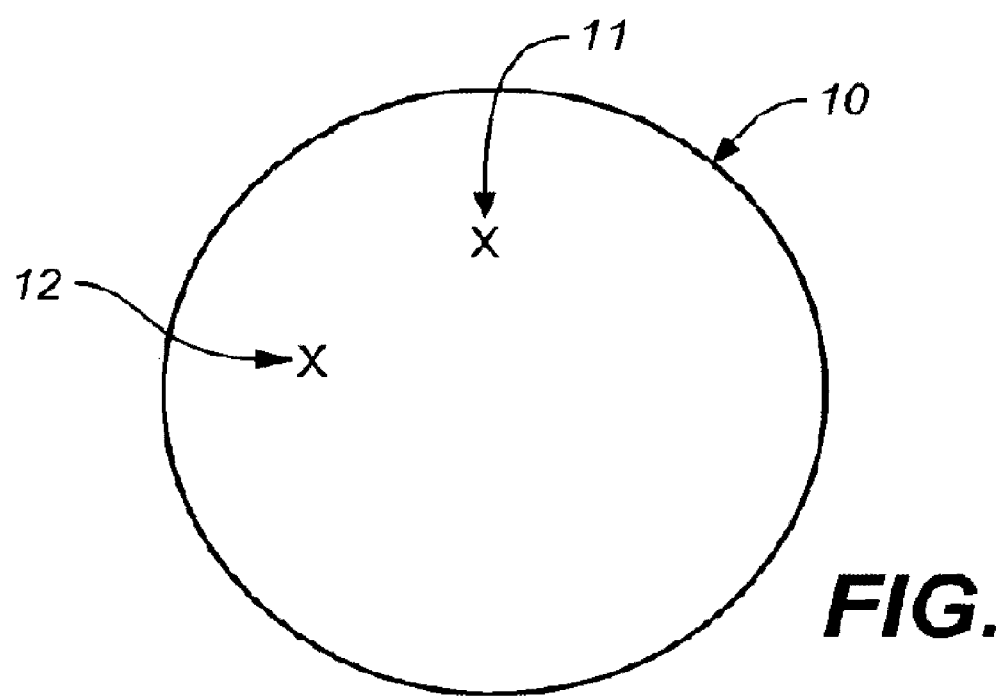
FIG. 1 is a schematic diagram illustrating the self-encoding microsphere sensor according to the present invention.

The present invention provides an analytic chemistry system that comprises a self-encoding sensor array comprising a population of beads or microspheres on discrete locations on the surface of a substrate. Within the bead population are separate bead subpopulations, each of which provides a characteristic optical response signature when illuminated by excitation light energy in the presence of a reference analyte, which may in some cases be the target analyte. Although the subpopulations may be randomly mixed together, the identity and location of each bead is determined via a characteristic optical response signature when illuminated by excitation light energy in the presence of a reference analyte.

This allows the decoding of the array, i.e. the identification of the location of each subpopulation of beads on an array, to proceed very simply. In a preferred embodiment, the beads are encoded with one or more reporter dyes that exhibit a characteristic, i.e. unique, optical response signature to a reference analyte, generally a fluid such as a vapor. Thus, in this embodiment, exposure of the entire array to a reference analyte will allow the identification of the location of each bead of each subpopulation. As a result, by comparing the response of the entire sensor array to a known analyte, the individual sensor elements of the array are conveniently decoded simultaneous in one simple measurement. The self-encoding feature of the present invention eliminates the need for a more complex, multi-step encoding system.

The sensor array can then be used to detect the presence of target analytes, for example when the beads also comprise bioactive agents such as oligonucleotides, by looking for changes in the optical signature of the beads upon binding of the target analyte, for example a substantially complementary labelled oligonucleotide. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event. Thus, once the location of each species of oligonucleotide probe has been identified, the array can then be used to detect the presence of unknowns that will preferably specifically associate with the bioactive agents on the beads.

In an alternate preferred embodiment, when the target analyte is not labeled, the optical response of each element in the array can be compared to a library of characteristic optical response signatures for its corresponding bead subpopulation type, where the characteristic optical response signature to various analytes has been previously measured and recorded, and either the identity of the unknown can be determined or the sensor array can be trained to associate the measured response with a particular analyte which is then added to the library of response signatures.

The present invention overcomes certain limitations of the current art by embodying the innovation of a self-encoding sensor array wherein a characteristic optical response signature is produced by the interaction of specific bead subpopulation compositions with a reporter dye. In the self-encoding sensor array of the present invention, the response signal to a target analyte serves both as a response signature for the target analyte and as the encoding signal for the entire sensor array and subpopulations within the array. The decoding of the array is thus accomplished in a one-step process during the array response measurement of a target analyte and utilizes the very response which is used to identify the target analyte. The bead encoding is thus incorporated into the array by the nature of the bead subpopulation responses to target analytes.

In the present invention, each bead-dye combination of a subpopulation has a characteristic optical response signature when exposed to a given fluid, usually a vapor. The self-encoding concept is provided by the unique response characteristics of the dye in combination with a specific bead matrix material. Thus the bead subpopulations which are randomly dispersed in a sensor array can be rapidly identified and located after placement in the array simply by exposing the sensor array to a known test fluid and matching the resulting optical response signature to those obtained for each bead subpopulation. With this approach, the beads are self encoding and the response characteristics of the entire sensor array are rapidly determined and stored for measurement of a target analyte. The method of the present invention is particularly useful in applications of sensor arrays containing thousands of sensors having distinctive optical response signature characteristics.

An additional benefit of the present invention is that it allows the synthesis of the bioactive agents (i.e. compounds such as nucleic acids and antibodies) to be separated from their placement on an array, i.e. the bioactive agents may be synthesized on the beads, and then the beads are randomly distributed on a patterned surface. Since the beads are self-encoded by having dyes present that have known responses to a reference analyte, this means that the array can later be "decoded", i.e. after the array is made, a correlation of the location of an individual site on the array with the bead or bioactive agent at that particular site can be made. This means that the beads may be randomly distributed on the array, a fast and inexpensive process as compared to either the in situ synthesis or spotting techniques of the prior art. Once the array is loaded with the beads, the array can be decoded, or can be used, with full or partial decoding occurring after testing, as is more fully outlined below.

In a preferred embodiment of the present invention, ultra-fine, porous microbeads or microspheres are utilized as individual sensors. The utilization of porous micron-scale sensors provides for improved sensor response and sensitivity. The reduction in sensor dimension substantially reduces the diffusion length and time for analyte interaction with individual sensors and significantly shortens the sensor response time, while simultaneously enhancing sensor sensitivity and lowering detection limits.

In another preferred embodiment of the present invention, the sensor array is comprised of subpopulations of beads or microspheres which are disposed on a distal end of an optical fiber bundle wherein the separate beads or microspheres may be optically coupled to discrete fibers or groups of fibers within the bundle. Since typically, such fiber optic bundles comprise thousands of discrete fibers, the present invention thus provides for an optical fiber sensor which can support a large number, thousands or more, of sensor array elements of distinct and varying subpopulations each having a characteristic optical response signature when exposed to an analyte while being illuminated by excitation light energy.

In one preferred embodiment, the distal end of a fiber optic bundle substrate is chemically etched so as to create a cavity or micro-well at the end of a discrete fiber. In the preferred embodiment, each one of the beads is located within separate microwells formed at terminal ends of optical fibers of the bundle. These microwells are formed by anisotropic etching of the cores of the optical fibers with respect to the cladding. The resultant etched cavity is dimensioned for accommodating an individual microbead sensor and for providing optical coupling of the individual bead sensor with the discrete optical fiber in the fiber bundle. Since typical fiber optic bundles contain thousands of discrete fibers, this embodiment provides for the individual optical coupling of thousands of sensors in a sensor array, thereby providing for a large number of independent sensor measurements for each bead subpopulation within the array.

Due to both the large number of bead sensor subpopulations available and the correspondingly large number of sensor elements within each subpopulation, a significant innovation of the present invention is in providing for thousands of independent sensor response measurements in a single sensor array. This enables another significant innovation of the present invention by providing for the summing and amplification of the characteristic optical response signatures of multiple independent measurements taken from sensor beads within each sensor array bead subpopulation. This approach directly mimics the actual behavior of the human olfactory where the combined signals from thousands of receptor cells in each of grouping of nearly a thousand different receptor cell types found in the epithelium layer, none of which are particularly sensitive in themselves, lead to a highly amplified sensory response to odors [see J. S. Kauer, *Trends Neurosci.* 14:79-95(1991)].

The present invention thus embodies the evolutionary scent amplification process found in the human olfactory system in order to significantly enhance sensor array sensitivity to analytes by summing the low-level responses of a large number of sensor array elements. By summing the responses from several beads at low vapor concentrations, a substantial improvement in signal-to-noise ratios is achieved, exceeding a factor of ten or more. This innovation has led to reducing the detection limit of the sensor array by over an order of magnitude. The enhancement in sensitivity provided by the sensor array of the present invention is generally known to be directly proportional to the square root of the number of independent sensor bead responses available for summing. With such enhancements, detection limits approaching parts per billion are achievable.

In preferred embodiments, the sensor beads are self-encoded using a reporter dye that is preferably infiltrated or entrapped within the beads. The reporter dye may be a chromophore or phosphor but is preferably a fluorescent dye, which due to characteristically strong optical signals provide a good signal-to-noise ratio for decoding. Although not necessary, the self-encoding can also be accomplished by utilizing the ratios of two or more reporting dyes having characteristic and discrete emission peaks and measuring the peak intensity ratios upon illumination with excitation light energy.

According to another embodiment, the invention also concerns a chemical sensor array designed with a predetermined chemical specificity. In this embodiment, additional chemical functionality can be incorporated into each sensor subpopulation by attaching a desired moiety to the surfaces of the beads. In another embodiment, the sensor array has a population of beads carrying chemical functionality at, on or near, a distal end of the bundle. The ability to monitor optical signature changes associated with individual or multiple beads interacting with a target analyte is provided by optically coupling those signature changes into separate optical fibers or groups of fibers of a fiber optic bundle for transmission to the proximal end where analysis is performed either manually, by the user, or automatically, using image processing techniques.

Although each sensor is different insofar that it has a different distribution of the subpopulations of beads within its microwells, only those beads that exhibit a positive optical response or signature change to a target analyte of interest need to be decoded. Therefore, the burden is placed on the analysis rather than on sensor manufacture. Moreover, since the beads and fibers in the array can be monodisperse, the fluorescent regions arising from signal generation are extremely uniform and can be analyzed automatically using commercially available microscopy analysis software. Such image processing software is capable of defining different spectral regions automatically and counting the number of segments within each region in several seconds.

Accordingly, the present invention provides array compositions comprising at least a first substrate with a surface comprising individual sites. By "array" herein is meant a plurality of bioactive agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 50,000 being particularly preferred, and from about 20,000 to about 30,000 being especially preferred. Low density arrays are generally less than 10,000, with from about 1,000 to about 5,000 being preferred. Very low density arrays are generally less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 nm can be used, and very small fibers are known, it is possible to have as many as 250,000 different fibers and beads in a 1 mm$^2$ fiber optic bundle, with densities of greater than 15,000,000 individual beads and fibers per 0.5 cm$^2$ obtainable.

The compositions comprise a substrate. By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybtitylene, polyurethanes, Teflon™, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not appreciably fluoresce.

Generally the substrate is flat or planar, although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

The compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon™ may all be used.

Synthetic beads may be fabricated by polymerizing or copolymerizing a variety of condensation or vinyl precursor monomers or by way of combinatorial polymer synthesis. Such polymers can be further modified by the addition of plasticizers, such as tritolyl phosphate (TTP), triphenyl phospate (TTP) or dibutyl phthalate (DBP). Particularly useful dye-encoding bead candidates for use in sensor array subpopulations are polymer and copolymer materials which exhibit either a characteristic swelling upon exposure to various vapor analytes, a characteristic polarity difference due to their chemical structure, or a characteristic chemical adsorption response with various vapor analytes. In prescreening candidate polymers as bead materials and evaluating candidates based on desirable swelling, polarity and adsorption characteristics, two particularly useful references are: R. A. McGill, et al., *Chemtech*, Sep. 24, 1996, p27-37 and J. W. Grate, et al., *Anal. Chem.* 68:913-7 (1996).

A variety of bead chemistries may be utilized in fabricating a wide diversity of sensor bead subpopulations. For example, the following compositions have been found to be particularly useful as candidate bead materials: silica, poly (ethylene glycol), polycaprolactone, poly(1,4-butylene adipate), PDPO [poly(2,6-dimethyl-1,4-phenyleneoxide)], PS078.5 [triethoxysilyl-modified polybutadiene (50% in toluene)], PS078.8 [diethoxymethylsilyl-modified polybutadiene in toluene], CPS2067 [acryloxypropylmethyl-cyclosiloxane], PS802 [(80-85%) dimethyl-(15-20%) (acryloxypropyl) methylsiloxane copolymer], PS901.5 poly (acryloxypropyl-methyl)siloxane], PS851 [(97-98%) dimethyl-(2-3%) (methacryloxypropyl) methylsiloxane copolymer], PABS [poly(acrylonitrile-butadiene-styrene)], poly(methyl methacrylate), poly(styrene-acrylonitrile 75:25), acryloxypropylmethylsiloxane-dimethylsiloxane copolymer, methylstyrene, polystyrene, acrylic polymers, and poly(methyl styrene/divinyl benzene). Other adsorbents, such as commercially available silica beads adapted with a variety of bonded phases for use in phenomenex columns, such as beads comprising C8, C18 and phenyl hexyl, are useful as sensor bead matrices. Inorganic materials such as alumina and zeolites may also be utilized. Other polymers and copolymers having distinguishable and suitable swelling behavior, polarity and chemical adsorption characteristics are also anticipated as likely bead candidate materials. Particularly useful bead candidate materials include the polymers, copolymers, and polymerized monomers listed in Table 7, Table 8 and Table 10 of U.S. Pat. No. 5,512,490 to Walt, et al, which are herein incorporated by reference. In alternative embodiments, any synthesized or commercially available bead materials may be further modified by applying either a surface treatment or coating to modify the characteristic optical response signature. For example, where porous silica beads are utilized, N-octadecyltriethyoxysilane or 3-(trimethoxysilyl)propyl methacrylate may be applied as a silanization treatment. In general, "*Microsphere Detection Guide*" from Bangs Laboratories, Fishers Ind. is a helpful guide.

The choice of subpopulations used to form the sensor array elements in a particular sensor array is primarily determined based on the analytical purposes of the sensor and the specific analytes which are targeted for detection. Typically, bead subpopulations are selected based on distinguishable differences in their characteristic optical response signatures when illuminated by excitation light energy in the presence of a target analyte. In fabricating self-encoding sensor arrays, bead subpopulations are selected which have characteristic optical response signatures when infiltrated with a reporting dye and illuminated by excitation light energy in the presence of both a reference analyte and target analyte. Thus, preferred bead materials for the sensor array are preselected based on either physical or chemical differences in bead subpopulations which produce a characteristic optical response signature in the presence of the analyte when illuminated by excitation light energy.

Features such bead material polarity, chemical structure, chemical functionality, bead surface area, bead pore size, bead swelling characteristics, or chemical adsorption behavior, either separately or in combination, contribute to the characteristic optical response signature of a given bead subpopulation. In one embodiment, bead materials which are permeable or semi-permeable to fluids including vapors and liquid analytes are preferred. In another embodiment, bead materials that swell upon contact with fluids such as vapor or liquid analytes are preferred. In general, bead materials which have unique polarity, structure, pore size, surface area, functionality or adsorption characteristics are particularly useful for sensor bead matrices of the present invention.

The microspheres comprise a reporting dye that, in combination with the characteristic bead matrix material, provides an optical response signature that can be used to identify the bead, and thus the attached bioactive agent, upon exposure to a reference analyte. That is, each subpopulation of microspheres (i.e. each sensor element) comprises a unique optical response signature or optical tag, that can be used to identify the unique bioactive agent of that subpopulation of microspheres; a bead comprising the unique optical response signature may be distinguished from beads at other locations with different optical response signatures. As is outlined herein, each bioactive agent will have an associated unique optical response signature such that any microspheres comprising that bioactive agent will be identifiable on the basis of the signature upon exposure to a reference analyte or fluid. As is more fully outlined below, it is possible to reuse or duplicate optical response signatures within an array, for example, when another level of identification is used, for example when beads of different sizes are used, or when the array is loaded sequentially with different batches of beads.

The selection of chemical dye indicators is equally important to the design of a fiber optic sensor array system of the present invention. In the preferred embodiment, at least one dye 11 is incorporated into the microsphere 10. In the preferred embodiment, this dye 11 acts as both an encoding dye, for identifying the bead subpopulation location in the sensor array, and a reporting dye, for detecting a target analyte of interest. In an alternative embodiment, two or more dyes may be utilized as encoding-reporter dyes. In a preferred embodiment, at least one dye is used solely as an encoding dye and a separate dye is added during analysis as a reporting dye. In one embodiment, where two or more encoding dyes are used, the ratio of peak intensities for dye pairs may be used for encoding the bead subpopulation and a separate reporter dye may be added during analysis. In an alternative embodiment, conjugated dyes, such as acrlyoyl fluorescein and others, may be utilized where it is desirable to incorporate the dye directly into a synthesized polymer or copolymer bead material.

While the reporter dye 11 may be either a chromophore-type or a fluorophore-type, a fluorescent dye is preferred because the strength of the fluorescent signal provides a better signal-to-noise ratio when decoding. In the most preferred embodiment, polarity-sensitive dyes or solvatochromic dyes are utilized. Solvatochromic dyes are dyes whose absorption or emission spectra are sensitive to and altered by the polarity of their surrounding environment. Typically, these dyes exhibit a shift in peak emission wavelength due to a change in local polarity. Polarity changes which cause such wavelength shifts can be introduced by the bead matrix used for a particular sensor bead subpopulation or, the presence of a target analyte. The change in polarity creates a characteristic optical response signature which is useful for both encoding subpopulations of bead types and for detecting specific target analytes. One preferred solvatochromic dye, Nile Red (Eastman Kodak, Rochester, N.Y.), exhibits large shifts in its emission wavelength peak with changes in the local environment polarity. In addition, Nile Red is soluble in a wide range of solvents, is photochemically stable, and has a relatively strong fluorescence peak. Additional dyes which are conventionally known in the art and may be used as dyes in the present invention are those found in U.S. Pat. No. 5,512,490 to Walt, et al., of which Table 3, Table 4, Table 5, Table 6 and Table I1 are incorporated herein by reference.

Different subpopulations of bead sensing elements can be fabricated for the sensor array of the present invention by immobilizing Nile Red in polymer matrices of varying composition. By incorporating Nile Red in bead subpopulations made from different polymer matrices of varying polarity, hydrophobicity, pore size, flexibility and swelling tendency, unique subpopulations of sensor beads are produced that react differently with molecules of individual fluids, giving rise to different fluorescence responses when exposed to organic fluids. This results in each bead subpopulation having a characteristic optical response signature when exposed to a variety of analytes.

In a preferred embodiment, the dyes are covalently attached to the surface of the beads. This may be done as is generally outlined below for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the bead matrix or pores of the beads.

In one embodiment, the dyes are added to the bioactive agent, rather than the beads, although this is generally not preferred.

Figure 2:
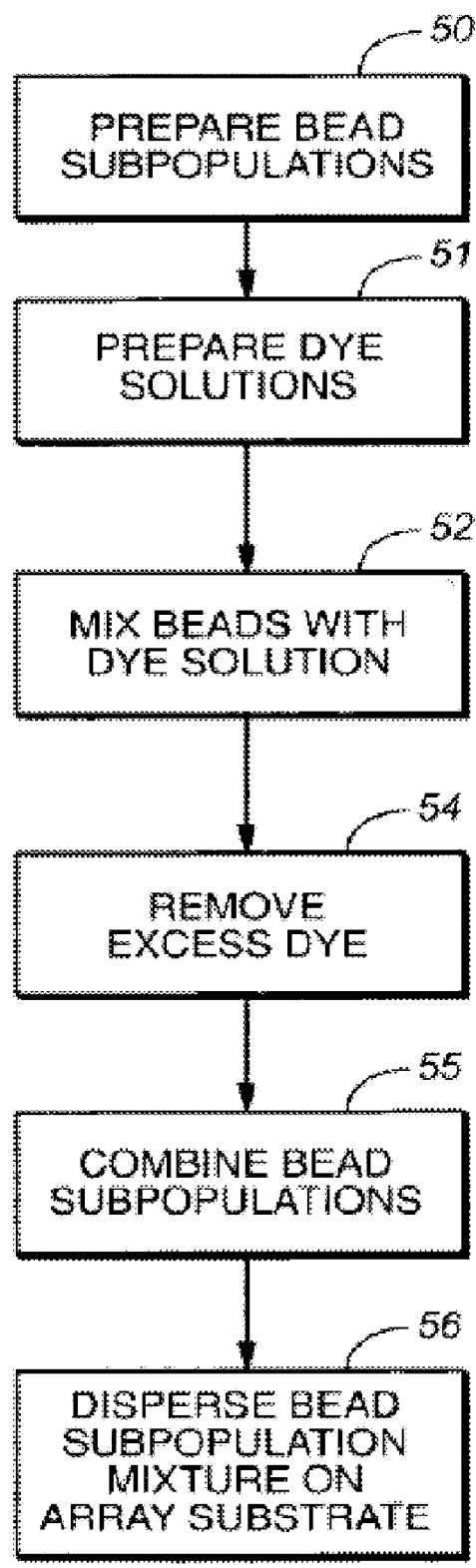
FIG. 2 is a process flow diagram of the preparation, encoding and incorporation of microspheres into a sensor array of the present invention.

FIG. 2 is a process diagram illustrating the preparation of the sensor bead subpopulations and sensor bead array. In step 50, suspensions of the various bead subpopulations are individually prepared from either commercial bead materials or synthesized bead materials which have been made from preferred polymeric materials. In this step, the beads may be prewashed, surface treated with a coupling agent, such as a silanizing solution as used in Example 2 and Example 3, or treated with a plasticizer, such as TTP, TPP or DBP as used in Example 6. In preparing the bead subpopulations, each bead grouping is typically dispersed in an appropriate solvent which may comprise additions of surfactants or dispersants to enhance dispersion. For example, Tween 20 (J. T. Baker, Cleveland, Ohio), a polyoxyethylenesorbitan monolaurate, has been found to be particularly useful as a surfactant.

A dye solution is prepared 51 for tagging or encoding each of the bead subpopulations for subsequent identification and indexing subpopulations in the sensor array in a later decoding step. In the most preferred embodiment, a single dye serves both as a sensor bead subpopulation encoding dye and as an analyte reporting dye that is used to detect the presence of a target analyte. In another embodiment, the dye serves solely to encode the sensor bead subpopulation and an additional dye is used as a reporter dye for detection of a target analyte. In one embodiment, two or more dyes may be incorporated into the bead subpopulation and the peak intensity ratios of dye pairs may be used for encoding the sensor bead subpopulation. Typically, a single solvatochromic dye is used as both the encoding dye and reporting dye. In a preferred embodiment, Nile Red dye (Aldrich, Milwaukee, Wis.) is used. For incorporating dye into each bead subpopulation, suspensions of the beads prepared in step 50 are mixed in step 52 with dye solutions prepared in step 51. Preferably, in step 52, the beads or microspheres are placed in a dye solution comprising dye dissolved in an organic solvent that will swell the microspheres. In step 54, the beads are washed, centrifuged or filtered to remove excess dye. The microspheres are typically washed in water, methanol, or any suitable solvent that does not swell the microspheres, but in which the dyes are still soluble. This allows the residual dye to be rinsed off without rinsing the dye out of the microspheres. In an alternative embodiment, a chemical moiety or functional group may be attached to the bead surface following removal of excess dye.

The beads need not be spherical; irregular particles may be used. While both porous and non-porous beads may be utilized, porous beads are preferred for infiltrating the reporter dye and enhancing the responsivity and sensitivity of the microsphere sensor due to an increase in surface area for attachment of the reporter dye, bioactive agents, etc. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used. FIG. 1 illustrates the construction of a typical bead or microsphere sensor 10 comprising a reporting dye 11 entrapped within bead pores 12.

It should be noted that a key component of the invention is the use of a substrate/bead pairing that allows the association or attachment of the beads at discrete sites on the surface of the substrate, such that the beads do not move during the course of the assay.

The present invention embodies a bead-based analytical chemistry system in which beads or microspheres are fabricated from various inorganic or organic materials wherein each material can be identified by a characteristic temporal optical response signature which enables verifying both the identity and location of a particular bead within a sensor array upon exposure to a reference analyte while illuminating with excitation light energy. The invention provides for utilization of any source of excitation light energy and is not limited to a specific wavelength. The principal requirement of the excitation light is that it produces emitted light of a characteristic wavelength upon illumination of a reporter dye associated with a given bead composition.

In a preferred embodiment, the microspheres further comprise a bioactive agent. By "candidate bioactive agent" or "bioactive agent" or "chemical functionality" or "binding ligand" herein is meant as used herein describes any molecule, e.g., protein, oligopeptide, small organic molecule, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins. Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least 10⁹ different bioactive agents are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic acids" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron*, 49(10): 1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al, *J. Am. Chem. Soc.*, 111:2321 (1989)), O-methylphosphoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Ensl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English*, 30:423 (1991); Letsinger, et al., *J. Am. Chem. Soc.*, 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al, *J. Biomolecular NMR*, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev.*, (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and basepair analogs such as nitropyrrole and nitroindole, etc.

As described above generally for proteins, nucleic acid bioactive agents may be naturally occurring nucleic acids, random nucleic acids, or "biased" random nucleic acids. For example, digests of procaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres are listed in Table I.

TABLE I

| Surface chemistry | Name |
| --- | --- |
| $NH_2$ | Amine |
| COOH | Carboxylic Acid |
| CHO | Aldehyde |
| $CH_2$—$NH_2$ | Aliphalic Amine |
| $CONH_2$ | Amide |
| $CH_2$—Cl | Chloromethyl |
| CONH—$NH_2$ | Hydrazide |
| OH | Hydroxyl |
| $SO_4$ | Sulfate |
| $SO_3$ | Sulfonate |
| $ArNH_2$ | Aromatic Amine |

These functional groups can be used to add any number of different bioactive agents to the beads, generally using known chemistries. For example, bioactive agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155-200, incorporated herein by reference) which can be used to attach cysteine containing proteinaceous agents to the support. Alternatively, an amino group on the bioactive agent may be used for attachment to an amino group on the surface. For example, a large number of stable bifunctional groups are well known in the art, including homobifunctional and heterobifunctional linkers (see Pierce Catalog and Handbook, pages 155-200). In an additional embodiment, carboxyl groups (either from the surface or from the bioactive agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems* 7(4):275-308 (1991), expressly incorporated herein). Proteinaceous bioactive agents may also be attached using other techniques known in the art, for example for the attachment of antibodies to polymers; see Slinkin et al., *Bioconj. Chem.* 2:342-348 (1991); Torchilin et al., supra; Trubetskoy et al., *Bioconj. Chem.* 3:323-327 (1992); King et al., *Cancer Res.* 54:6176-6185 (1994); and Wilbur et al., *Bioconjugate Chem.* 5:220-235 (1994), all of which are hereby expressly incorporated by reference). It should be understood that the bioactive agents may be attached in a variety of ways, including those listed above. What is important is that manner of attachment does not significantly alter the functionality of the bioactive agent; that is, the bioactive agent should be attached in such a flexible manner as to allow its interaction with a target.

Specific techniques for immobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, KCl). This is stirred on a stir bed for approximately 2 hours at room temperature. The microspheres are then rinsed with ultrapure water plus 0.01% tween 20 (surfactant)-0.02%, and rinsed again with a pH 7.7 PBS plus 0.01% tween 20. Finally, the enzyme is added to the solution, preferably after being prefiltered using a 0.45 µm amicon micropure filter.

Figure 3:
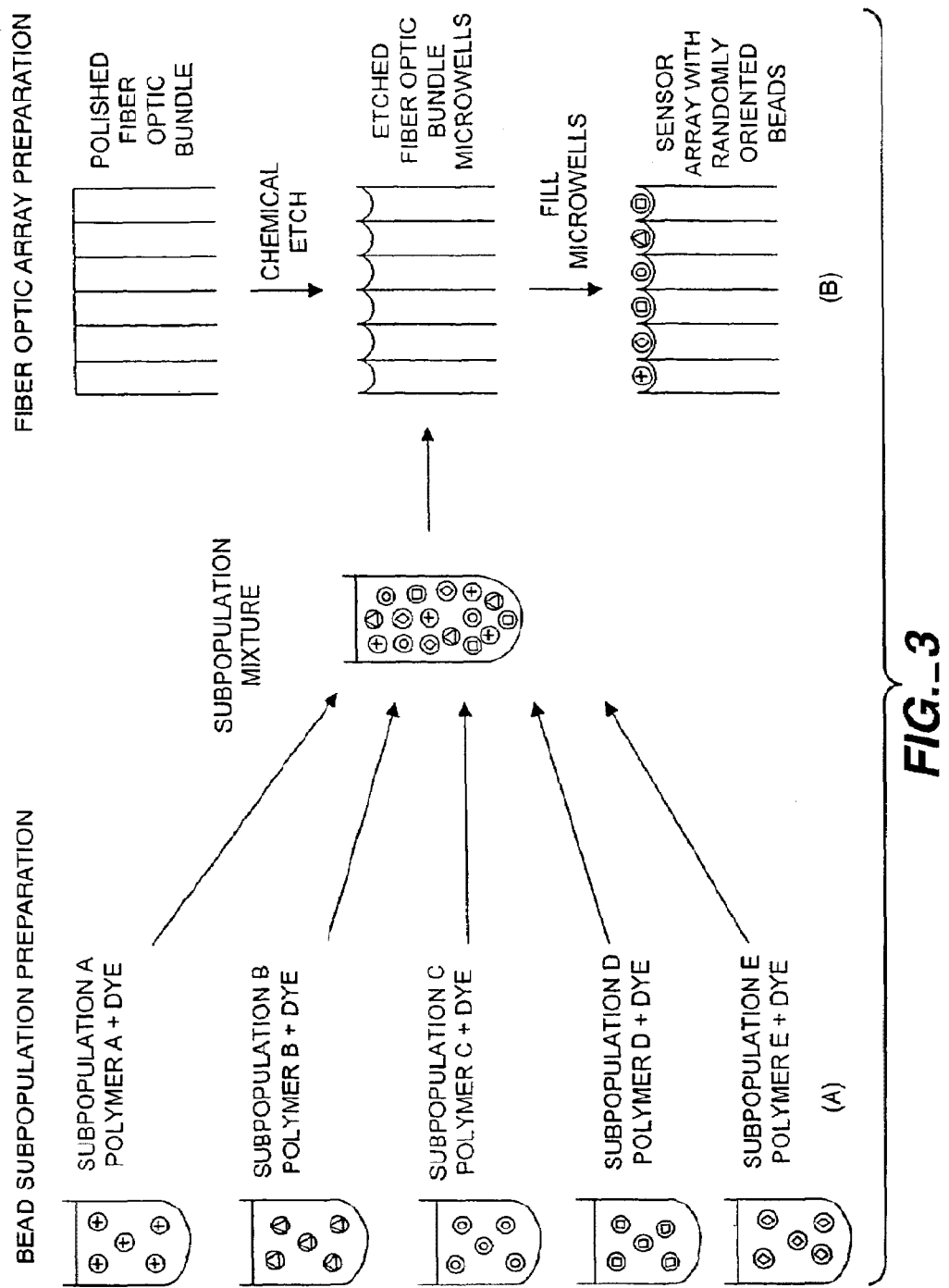
FIGS. 3A and 3B is a schematic process diagram illustrating the preparation and placement of self-encoded microsphere subpopulations in fiber optic sensor array of the present invention.

After the desired number of bead subpopulations are prepared by the method of steps 50 through 54, discussed above, the subpopulations are typically combined in step 55 to provide a random mixture of subpopulations for use as sensor array elements prior to dispersing the subpopulation mixture on the array substrate in step 56. In a preferred embodiment, FIG. 3. shows a schematic process diagram which illustrates the preparation and placement of self-encoded sensor bead subpopulations in fiber optic bundle sensor array. In an alternative embodiment, step 55 may be omitted and each of the sensor bead subpopulations may be separately and sequentially positioned on the array substrate in predetermined locations.

Thus, once the microspheres are made comprising at least one bioactive agent and a self-encoding reporter dye, the microspheres are added to discrete sites on the surface of the substrate. This can be done in a number of ways, but generally comprises adding the beads to the surface under conditions that will allow the association of the microspheres on or at the discrete sites. The association of the beads on the surface may comprise a covalent bonding of the bead to the surface, for example when chemical attachment sites are added to both the substrate and the bead; an electrostatic or hydroaffinity, when charge, hydrophobicity or hydrophilicity is used as the basis of the binding; a physical yet non-covalent attachment such as the use of an adhesive; or a spatial attachment, for example the localization of a bead within a well. In some embodiments it may be preferable to effect a more permanent attachment after the initial localization, for example through the use of cross-linking agents, a film or membrane over the array.

The microsphere system may be attached to the distal end of the optical fiber bundle using a variety of compatible processes as outlined below. It is important that the microspheres are located close to the end of the bundle. This ensures that the light returning in each optical fiber predominantly comes from only a single microsphere. This feature is necessary to enable the interrogation of the optical response signature of individual microspheres to identify reactions involving the microsphere's functionality and also to decode the dye/bead sets contained in those microspheres. The adhesion or affixing technique, however, must not chemically insulate the microspheres from the analyte.

FIG. 7 is a schematic block diagram showing the inventive optical fiber sensor 200 and associated control system 210. The fiber optic sensor 200 comprises a fiber optic bundle 202 (Galileo Electro-Optics, Sturbridge, Mass.), that is typically constructed from many thousands of separately clad discrete fibers, each only a few microns in diameter, so that light does not mix between the individual fibers. Any suitable fiber optic bundle 202 may be employed having a range in the number of individual fibers or a range of individual fiber diameters. The microsphere or bead sensor array 100 is attached to the bundle's distal end 212, with the proximal end 214 being received by a conventional z-translation microscope stage 216, for vertical positioning of the array 100 for focusing, and an x-y micropositioner 218 (Burleigh Instruments, Fishers, N.Y.), for horizontal alignment of the array 100 with the optical train. These two components act in concert to properly position the proximal end 214 of the bundle 202 for a microscope objective lens 220. Light collected by the objective lens 220 is passed to a reflected light fluorescence attachment with a four position dichromic cube wheel 222. The attachment 222 allows insertion of light from a 75 Watt Xenon arc lamp 224 through the objective lens 220 to be coupled into the fiber bundle 202. The light from the source 224 is condensed by condensing lens 226, then filtered and/or shuttered by filter and shutter wheel 228.

Light returning from the distal end 212 of the bundle 202 is passed by the attachment 222 and is then shuttered and filtered by a second wheel 234. The light is then imaged on a charge coupled device (CCD) camera 236. A conventional computer 238 executes imaging processing software to process the information from the CCD camera 236 and also possibly control the first and second shutter and filter wheels 228, 234. Either a Macintosh or, alternatively, an IBM-compatible personal computer may be utilized for controlling the instrumentation and data acquisition. The instrumentation and optical apparatus deployed at the proximal end 214 of the fiber optic sensor 200, exclusive of the fiber optic sensor 200, are discussed more completely by Bronk, et al., Anal. Chem. 67(17):2750-2752(1995) and Bronk, et al., Anal. Chem. 66:3519 (1994).

The bead sensor array 100 may be attached to the distal end of the optical fiber bundle 202 using a variety of compatible processes. It is important that the microspheres 10 are located close to the end of the bundle. This ensures that the light returning in each discrete optical fiber predominantly comes from only a single microsphere. This feature is necessary to decode the self-encoded bead subpopulations for the purpose of identifying both bead type and location, to enable the interrogation of the optical signature of individual microspheres within a bead subpopulation, and to provide for the summing of individual bead responses within each subpopulation for reducing signal to noise and improving signal enhancement. The bead adhesion or affixing technique, however, must not chemically insulate the microspheres from the analyte or interfere with the optical measurement.

FIGS. 5A and 5B are micrographs illustrating the preferred method for attaching beads to a sensor array substrate. Microwells 250 are formed on the distal end 212 of a fiber optic bundle 202 and microspheres 10 are inserted in the microwell cavities 250. The microwells 250 are formed at the center of each optical fiber 252 of the fiber optic bundle 202. As shown in FIG. 5B, the size of the microwells 250 are coordinated with the size of the microspheres 10 so that the microspheres 10 can be placed within the microwells 250. Thus, each optical fiber 252 of the bundle 202 conveys light from the single microsphere 10 contained in its well. Consequently, by imaging the end of the bundle 202 onto the CCD array 236, the optical signatures of the microspheres 10 are individually interrogatable.

Figure 4:
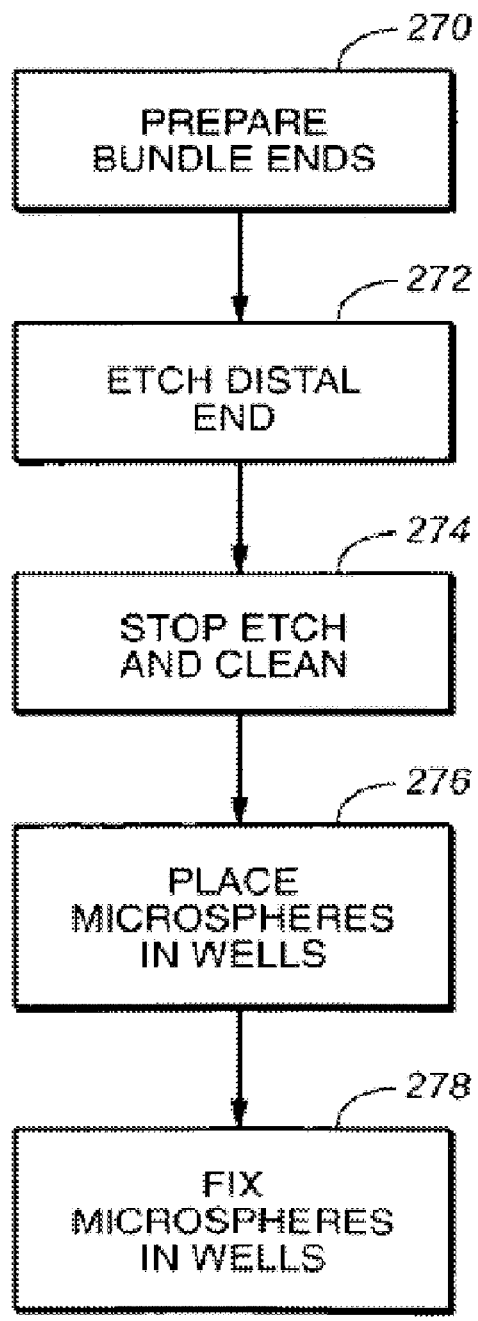
FIG. 4 is a process flow diagram illustrating microwell formation in the fiber optic bundle and placement of the microspheres in the microwells according to the method of the present invention.

FIG. 4 illustrates how the microwells 250 are formed and microspheres 10 placed in the microwells. In one embodiment, a 1 mm hexagonally-packed imaging fiber bundle 202 was employed comprising approximately 20,600 individual optical fibers having cores approximately 3.7 µm across (Part No. ET26 from Galileo Fibers, Sturbridge, Mass.). Typically, the cores of each fiber are hexagonally shaped as a result of glass hardness and drawing during fiber fabrication. In some cases, the shape can be circular, however.

In step 270, both the proximal 214 and distal 212 ends of the fiber bundle 202 are successively polished on 12 µm, 9 µm, 3 µm, 1 µm, and 0.3 µm lapping films. Subsequently, the ends can be inspected for scratches on a conventional atomic force microscope. In step 272, etching is performed on the distal end 212 of the bundle 202. A solution of 0.2 grams $NH_4F$ (ammonium fluoride) with 600 µl $dH_2O$ and 100 µl of HF (hydrofluoric acid), 50% stock solution, may be used. The distal end 212 is etched in this solution for a specified time, preferably approximately 80 seconds.

Upon removal from this solution, the bundle end is immediately placed in deionized water to stop any further etching in step 274. The fiber is then rinsed in running tap water. At this stage, sonication is preferably performed for several minutes to remove any salt products from the reaction. The fiber is then allowed to air dry.

As illustrated in FIGS. 5A and 5B, the foregoing procedure produces microwells by the anisotropic etching of the fiber cores 254 favorably with respect to the cladding 256 for each fiber of the bundle 202. The microwells have approximately the diameter of the cores 254, 3.7 µm. This diameter is selected to be slightly larger than the diameters of the microspheres used, 3.1 µm, in the example. The preferential etching occurs because the pure silica of the cores 254 etches faster in the presence of hydrofluoric acid than the germanium-doped silica claddings 256.

The microspheres are then placed in the microwells 250 in step 276 according to a number of different techniques. The placement of the microspheres may be accomplished by dripping a solution containing the desired randomly mixed subpopulations of the microspheres over the distal end 212, sonicating the bundle to settle the microspheres in the microwells, and allowing the microsphere solvent to evaporate. Alternatively, the subpopulations could be added serially to the bundle end. Microspheres 10 may then be fixed into the microwells 250 by using a dilute solution of sulfonated Nafion that is dripped over the end. Upon solvent evaporation, a thin film of Nafion was formed over the microspheres which holds them in place. This approach is compatible for fixing microspheres for pH indication that carry FITC functionality. The resulting array of fixed microspheres retains its pH sensitivity due to the permeability of the sulfonated Nafion to hydrogen ions. This approach, however, can not be employed generically as Nafion is impermeable to most water soluble species. A similar approach can be employed with different polymers. For example, solutions of polyethylene glycol, polyacrylamide, or polyhydroxymethyl methacrylate (polyHEMA) can be used in place of Nafion, providing the requisite permeability to aqueous species.

In an another embodiment, an alternative fixation approach employs microsphere swelling to entrap each microsphere 10 in its corresponding microwell 250. In this approach, the microspheres are first distributed into the microwells 250 by sonicating the microspheres suspended in a non-swelling solvent in the presence of the microwell array on the distal end 212. After placement into the microwells, the microspheres are subsequently exposed to an aqueous buffer in which they swell, thereby physically entrapping them in the microwells. By way of example of this particular embodiment, one commonly known microsphere material is tentagel, a styrene-polyethylene glycol copolymer. These microspheres can be unswollen in nonpolar solvents such as hexane and swell approximately 20-40% in volume upon exposure to a more polar or aqueous media. In certain embodiments, this fixation approach may be desirable since it does not significantly compromise the diffusional or permeability properties of the microspheres themselves.

FIGS. 6A and 6B show typical microspheres 10 in microwells 250 after their initial placement and then after tapping and exposure to air pulses. FIGS. 7A and 7B illustrate that there is no appreciable loss of microspheres from the microwells due to mechanical agitation even without a specific fixing technique. This effect is probably due to electrostatic forces between the microspheres and the optical fibers. These forces tend to bind the microspheres within the microwells. Thus, in most environments, it may be unnecessary to use any chemical or mechanical fixation for the microspheres.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to attach the beads in a non-random or ordered way. For example, using photoactivatible attachment linkers or photoactivatible adhesives or masks, selected sites on the array may be sequentially rendered suitable for attachment, such that defined populations of beads are laid down.

In addition, since the size of the array will be set by the number of unique optical response signatures, it is possible to "reuse" a set of unique optical response signatures to allow for a greater number of test sites. This may be done in several ways; for example, by using a positional coding scheme within an array; different sub-bundles may reuse the set of optical response signatures. Similarly, one embodiment utilizes bead size as a coding modality, thus allowing the reuse of the set of unique optical response signatures for each bead size. Alternatively, sequential partial loading of arrays with beads can also allow the reuse of optical response signatures.

In a preferred embodiment, a spatial or positional coding system is done. In this embodiment, there are sub-bundles or subarrays (i.e. portions of the total array) that are utilized. By analogy with the telephone system, each subarray is an "area code", that can have the same tags (i.e. telephone numbers) of other subarrays, that are separated by virtue of the location of the subarray. Thus, for example, the same unique dye/bead combinations can be reused from bundle to bundle. Thus, the use of 50 unique tags in combination with 100 different subarrays can form an array of 5000 different bioactive agents. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of optical response signatures; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye/bead combinations could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical response signatures can be "reused". In this embodiment, the library of microspheres each comprising a different bioactive agent (or the subpopulations each comprise a different bioactive agent), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each bioactive agent is determined, using its optical response signature. The second sublibrary is then added, and the location of each optical response signature is again determined. The signal in this case will comprise the "first" optical response signature and the "second" optical response signature; by comparing the two matrices the location of each bead in each sublibrary can be determined. Similarly, adding the third, fourth, etc. sublibraries sequentially will allow the array to be filled.

Thus, arrays are made of a large spectrum of chemical functionalities utilizing the compositions of invention comprising microspheres and substrates with discrete sites on a surface. Specifically, prior art sensors which can be adapted for use in the present invention include four broad classifications of microsphere sensors: 1) basic indicator chemistry sensors; 2) enzyme-based sensors; 3) immuno-based sensors (both of which are part of a broader general class of protein sensors); and 4) geno-sensors.

In a preferred embodiment, the bioactive agents are used to detect chemical compounds. A large number of basic indicator sensors have been previously demonstrated. Examples include:

TABLE III

| TARGET ANALYTE | Bioactive agent | NOTES ($\lambda_{AB}/\lambda_{EM}$) |
|---|---|---|
| pH Sensors based on: | seminaphthofluoresceins | e.g., carboxyl-SNAFL |
| | seminaphthorhodafluors | e.g., carboxyl-SNARF |
| | 8-hydroxypyrene-1,3,6-trisulfonic acid | |
| | fluorescein | |
| CO2 Sensors based On: | seminaphthofluoresceins | e.g., carboxyl-SNAFL |
| | seminaphthorhodafluors | e.g., carbody-SNARF |
| | 8-hydroxypyrene-1,3,6-trisulfonic acid | |
| Metal Ions Sensors based on: | desferriozamine B | e.g., Fe |
| | cyclen derivative | e.g., Cu, Zn |
| | derivatized peptides | e.g., FITC-Gly-Gly-His, and FITC-Gly His, Cu, Zn |
| | fluorexon (calcine) | e.g., Ca, Mg, Cu, Pb, Ba |
| | calcine blue | e.g., Ca, Mg, Cu |
| | methyl calcine blue | e.g., Ca, Mg, Cu |
| | ortho-dianisidine tetracetic acid (ODTA) | e.g., Zn |
| | bis-salicylidene ethylenediamine (SED) | e.g., Al |
| | N-(6-methozy-8-quinolyl-p-toluenesulfonamine (TSQ) | e.g., Zn |
| | Indo-1 | e.g., Mn, Ni |
| | Fura-2 | e.g., Mn, Ni |
| | Magesium Green | e.g., Mg, Cd, Tb |
| $O_2$ | Siphenylisobenzofuran | 409/476 |
| | Methoxyvinyl pyrene | 352/401 |
| Nitrite | diaminonaphthalene | 340/377 |
| NO | luminol | 355/411 |
| | dihydrohodamine | 289/none |
| $Ca^{2+}$ | Bis-fura | 340/380 |
| | Calcium Green | visible light/530 |
| | Fura-2 | 340/380 |
| | Indo-1 | 405/485 |
| | Fluo-3 | visible light/525 |
| | Rhod-2 | visible light/570 |
| $Mg^{2+}$ | Mag-Fura-2 | 340/380 |
| | Mag-Fura-5 | 340/380 |
| | Mag-Indo-1 | 405/485 |
| | Magnesium Green | 475/530 |
| | Magnesium Orange | visible light/545 |
| $Zn^{2+}$ | Newport Green | 506/535 |
| TSQ | Methoxy-Quinobyl | 334/385 |
| $Cu^+$ | Phen Green | 492/517 |
| $Na^+$ | SBFI | 339/565 |
| | SBFO | 354/575 |
| | Sodium Green | 506/535 |
| $K^+$ | PBFI | 336/557 |
| $Cl^-$ | SPQ | 344/443 |
| | MQAE | 350/460 |

Each of the chemicals listed in Table III directly produces an optically interrogatable signal or a change in the optical signature, as is more fully outlined below, in the presence of the targeted analyte.

Enzyme-based microsphere sensors have also been demonstrated and could be manifest on microspheres. Examples include:

TABLE IV

| SENSOR TARGET | Bioactive agent |
|---|---|
| Glucose Sensor | glucose oxidase (enz.) + $O_2$-sensitive dye (see Table I) |
| Penicillin Sensor | penicillinase (enz.) + pH-sensitive dye (see Table I) |
| Urea Sensor | urease (enz.) + pH-sensitive dye (see Table I) |
| Acetylcholine Sensor | acetylcholinesterase (enz.) + pH-sensitive dye (see Table I) |

Generally, as more fully outlined above, the induced change in the optical signal upon binding of the target analyte due to the presence of the enzyme-sensitive chemical analyte occurs indirectly in this class of chemical functionalities. The microsphere-bound enzyme, e.g., glucose oxidase, decomposes the target analyte, e.g., glucose, consume a co-substrate, e.g., oxygen, or produce some by-product, e.g., hydrogen peroxide. An oxygen sensitive dye is then used to trigger the signal change.

Immuno-based microsphere sensors have been demonstrated for the detection for environmental pollutants such as pesticides, herbicides, PCB's and PAH's. Additionally, these sensors have also been used for diagnostics, such as bacterial (e.g., leprosy, cholera, lyme disease, and tuberculosis), viral (e.g., HIV, herpes simplex, cytomegalovirus), fungal (e.g., aspergillosis, candidiasis, cryptococcoses), Mycoplasmal (e.g., mycoplasmal pneumonia), Protozoal (e.g., amoebiasis, toxoplasmosis), Rickettsial (e.g., Rocky Mountain spotted fever), and pregnancy tests.

Microsphere genosensors may also be made. These are typically constructed by attaching a probe sequence to the microsphere surface chemistry, typically via an $NH_2$ group. A fluorescent dye molecule, e.g., fluorescein, is attached to the target sequence, which is in solution. The optically interrogatable signal change occurs with the binding of the target sequences to the microsphere. This produces a higher concentration of dye surrounding the microsphere than in the solution generally. A few demonstrated probe and target sequences, see Ferguson, J. A. et al. *Nature Biotechnology*, Vol. 14, December 1996, are listed below in Table V.

TABLE V

| PROBE SEQUENCES | TARGET SEQUENCES |
|---|---|
| B-glo(+) (segment of human B-globin)5'-$NH_2$-$(CH_2)_8$-)TT TTT TTT TCA ACT TCA TCC ACG TTC ACC-3 | B-glo(+)-CF 5'-Fluorescein-TC AAC GTG GAT GAA GTT C-3' |
| IFNG(interferon gamma 1)5'-$NH_2$-$(CH_2)_8$-$T_{12}$-TGG CTT CTC TTG GCT GTT ACT-3' | IFNG-CF 5'-Fluorescein-AG TAA CAG CCA AGA GAA CCC AAA-3' |
| IL2(interleukin-2)5'-$NH_2$-$(CH_2)_8$-$T_{12}$-TA ACC GAA TCC CAA ACT CAC CAG-3' | IL2-CF 5'-Fluorescein-CT GGT GAG TTT GGG ATT CTT GTA-3' |
| IL4(interleukin-4)5'$NH_2$-$(CH_2)_8$-$T_{12}$-CC AAC TGC TTC CCC CTC TGT-3' | IL4-CF 5'-Fluorescein-AC AGA GGG GGA AGC AGT TGG-3' |
| IL6(interleukin-6)5'$NH_2$-$(CH_2)_8$-T12-GT TGG GTC AGG GGT GOT TAT T-3' | IL6-CF 5'-Fluorescein-AA TAA CCA CCC CTG ACC CAA C-3' |

It should be further noted that the genosensors can be based on the use of hybridization indicators as the labels. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up.

The present invention may be used with any or all of these types of sensors. As will be appreciated by those in the art, the type and composition of the sensor will vary widely, depending on the composition of the target analyte. That is, sensors may be made to detect nucleic acids, proteins (including enzyme sensors and immunosensors), lipids, carbohydrates, etc; similarly, these sensors may include bioactive agents that are nucleic acids, proteins, lipids, carbohydrates, etc. In addition, a single array sensor may contain different binding ligands for multiple types of analytes; for example an array sensor for HIV may contain multiple nucleic acid probes for direct detection of the viral genome, protein binding ligands for direct detection of the viral particle, immuno-components for the detection of anti-HIV antibodies, etc.

In addition to the beads and the substrate, the compositions of the invention may include other components, such as light sources, optical components such as lenses and filters, detectors, computer components for data analysis, etc.

The arrays of the present invention are constructed such that information about the identity of the bioactive agent is built into the array, such that the random deposition of the beads on the surface of the substrate can be "decoded" to allow identification of the bioactive agent at all positions. This may be done in a variety of ways.

In a preferred embodiment, the beads are loaded onto the substrate and then the array is decoded, prior to running the assay. This is done by detecting the optical response signature associated with the bead at each site on the array upon exposure to a reference analyte. This may be done all at once, if unique optical signatures are used, or sequentially, as is generally outlined above for the "reuse" of sets of optical signatures. Alternatively, full or partial decoding may occur after the assay is run.

Once made and decoded if necessary, the compositions find use in a number of applications. As a preliminary matter, the invention finds use in methods for reducing the signal-to-noise ratio in the characteristic optical response signature of a sensor array having a subpopulations of array elements. The methods comprise a) decoding the array so as to identify the location of each sensor element within each sensor subpopulation within the array; b) measuring the characteristic optical response signature of each sensor element in the array; c) adjusting the baseline of the optical response signature for each sensor element in the array; d) summing the baseline-adjusted characteristic optical response signature of all sensor elements within each of the sensor subpopulations; and e) reporting the characteristic optical response signature of each sensor subpopulation as a summation of the baseline-adjusted characteristic optical response signatures of all sensor elements within each of the subpopulations. This can result in an increase in the signal-to-noise ratio by a factor of at least about ten, with at least about 100 being preferred.

Similarly, the invention provides methods for amplifying the characteristic optical response signature of a sensor array having subpopulations of array elements, comprising: a) decoding the array so as to identify the location of each sensor element within each sensor subpopulation within the array; b) measuring a characteristic optical response signature of each sensor element in the array; c) optionally adjusting the baseline of the optical response signature for each sensor element in the array; d) summing the baseline-adjusted characteristic optical response signature of all sensor elements within each of the sensor subpopulations; and e) reporting the characteristic optical response signature of each sensor subpopulation as a summation of the baseline-adjusted characteristic optical response signatures of all sensor elements within each of the subpopulations. In a preferred embodiment, the signal is amplified by a factor of at least about fifty and an analyte detection limit is reduced by a factor of at least about 100.

Generally, a sample containing a target analyte (whether for detection of the target analyte or screening for binding partners of the target analyte) is added to the array, under conditions suitable for binding of the target analyte to at least one of the bioactive agents, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorochromes, for example during PCR amplification as is known in the art. Alternatively, upon binding of the target sequences, an intercalating dye (e.g., ethidium bromide) can be added subsequently to signal the presence of the bound target to the probe sequence. Upon binding of the target analyte to a bioactive agent, there is a new optical signal generated at that site, which then may be detected.

Alternatively, in some cases, as discussed above, the target analyte such as an enzyme generates a species (for example, a fluorescent product) that is either directly or indirectly detectable optically.

Furthermore, in some embodiments, a change in the optical response signature may be the basis of the optical signal. For example, the interaction of some chemical target analytes with some fluorescent dyes on the beads may alter the optical response signature, thus generating a different optical signal. For example, fluorophore derivatized receptors may be used in which the binding of the ligand alters the signal.

As will be appreciated by those in the art, in some embodiments, the presence or absence of the target analyte may be done using changes in other optical or non-optical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In a preferred embodiment, the compositions are used to probe a sample solution for the presence or absence of a target analyte. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e. drug candidate) is sought.

Suitable analytes include organic and inorganic molecules, including biomolecules. When detection of a target analyte is done, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc), whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are nucleic acids and proteins.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins.

In a preferred embodiment, the target analyte is a nucleic acid. These assays find use in a wide variety of applications.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

The present invention also finds use as a methodology for the detection of mutations or mismatches in target nucleic acid sequences. For example, recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). The compositions of the present invention may easily be substituted for the arrays of the prior art.

In a preferred embodiment, the compositions of the invention are used to screen bioactive agents to find an agent that will bind, and preferably modify the function of, a target molecule. As above, a wide variety of different assay formats may be run, as will be appreciated by those in the art. Generally, the target analyte for which a binding partner is desired is labeled; binding of the target analyte by the bioactive agent results in the recruitment of the label to the bead, with subsequent detection.

In a preferred embodiment, the binding of the bioactive agent and the target analyte is specific; that is, the bioactive agent specifically binds to the target analyte. By "specifically bind" herein is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Characteristic temporal optical response data measurements of sensor bead and sensor array response to specific vapor analytes and excitation light energy were made according to the established method and instrumentation disclosed by White, et al., *Anal. Chem.* 68:2191-2202(1996). In FIG. 8, a schematic diagram illustrates the experimental apparatus and instrumentation used for the data measurements reported in Examples 7 through 17. In a typical measurement, the proximal end 214 of a fiber optic bundle 202 was placed into a fiber chuck 300 and secured for viewing with an Olympus microscope-based imaging system. In other embodiments, a conventional Olympus microscope slide platform and slide clamp was used for positioning alternative sensor array substrates, such as glass cover slips. An Olympus microscope 320 equipped with an epi-illuminator was utilized for optical measurements. The microscope 320 was equipped with Olympus 20× and 40× and Zeiss 100× objectives. An Omega 560 DCRP dichroic mirror 330 was used to direct filtered exitation light energy from a 75 W Xenon arc lamp 340 to the sensor array 100 and to permit the emitted light energy, due to the characteristic optical response signature originating from each of the sensor beads 10 in the sensor array 100, to be recorded by a CCD frame transfer camera 310. The excitation light energy emanating from the arc lamp 340 was filtered by an Omega 535 BP40 integrated excitation light filter/shutter 350. The emission light energy which emitted from the sensor beads 10 of the sensor array 100 was filtered with an Omega 640 BP20 integrated emitted light filter/shutter 360 prior to the CCD frame transfer camera 310.

Experiments generally consist of collecting video camera frames of fluorescence response images of the characteristic optical response signatures of individual sensor beads in the sensor array 100 conveyed by the fiber optic bundle 202 to its proximal end 214. The bead and array images are recorded with a CCD frame transfer camera 310 (Model TE512EFT from Princeton Instruments, Trenton, N.J.). A preselected number of image frames are captured and sent to a computer system 400, comprising a Princeton Instruments NUBus camera interface card installed in a 8100 AV Macintosh Power PC. Camera frame rates can be set at any desired value and typically range between 80 to 250 ms/frame. The following is a list of frame rates (time between data points) used in acquiring the data shown in for FIGS. 9-16. The specified frame rate corresponds to a specific time interval between data points.

Figure 13:
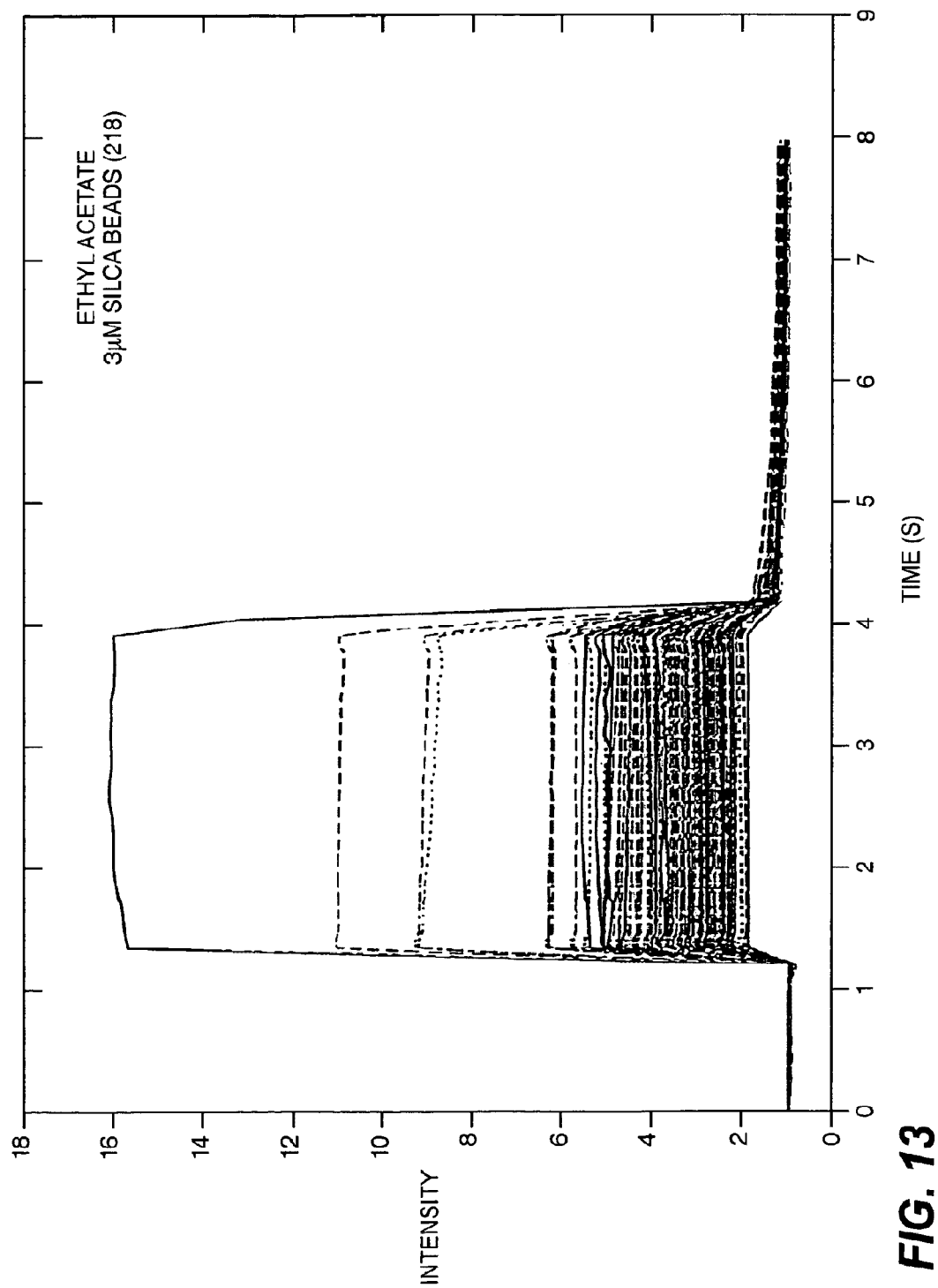
FIG. 13 illustrates the characteristic optical response signature of porous silica beads infiltrated with Nile Red dye upon exposure to ethyl acetate vapor.

| Figure | Rate (ms/frame) | Total No. of Frames |
|---|---|---|
| FIG. 9 | 135 | 30 |
| FIG. 10 | 183.3 | 60 |
| FIG. 11 | 103.3 | 60 |
| FIG. 12 | 190.6 | 60 |
| FIG. 13 | 133 | 60 |

-continued

Figure 14:
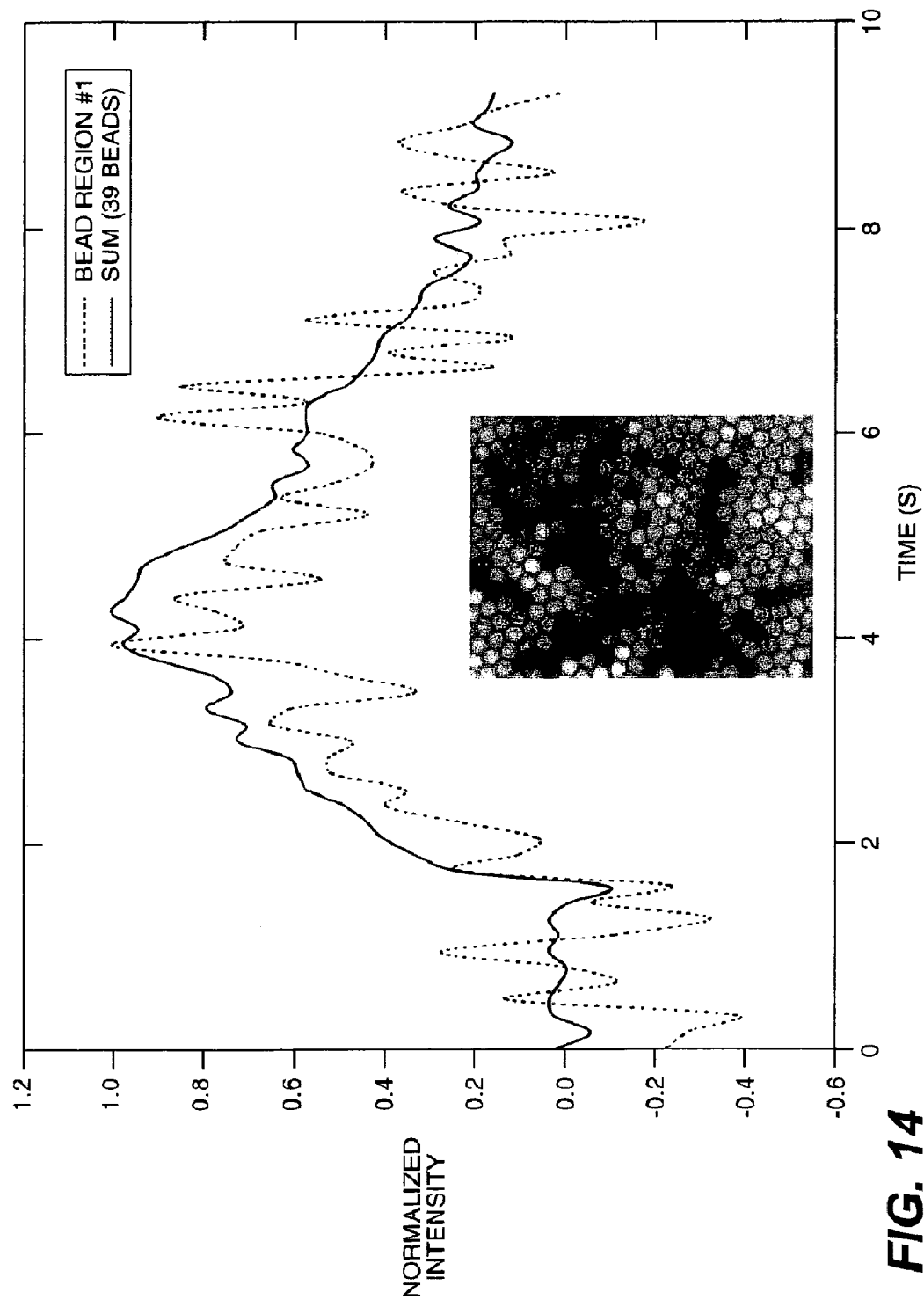
FIG. 14 illustrates the innovation of optical response signal summing for reducing signal-to-noise ratios in Nile Red infiltrated PMS bead subpopulation measurements of methanol vapor.
Figure 15:
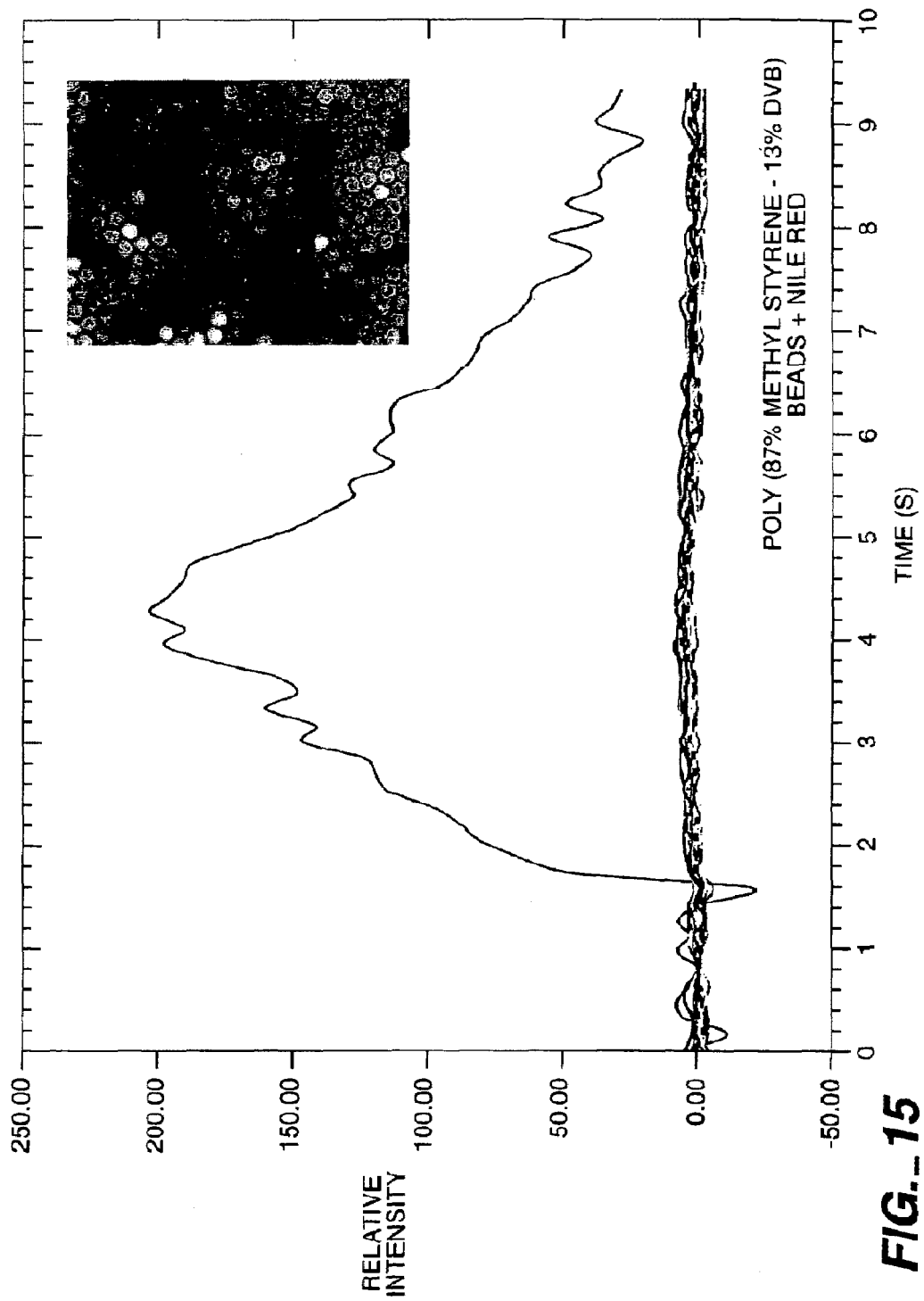
FIG. 15 illustrates the innovation of optical response signal summing for signal enhancement in PMS bead subpopulation measurements of methanol vapor.
Figure 16:
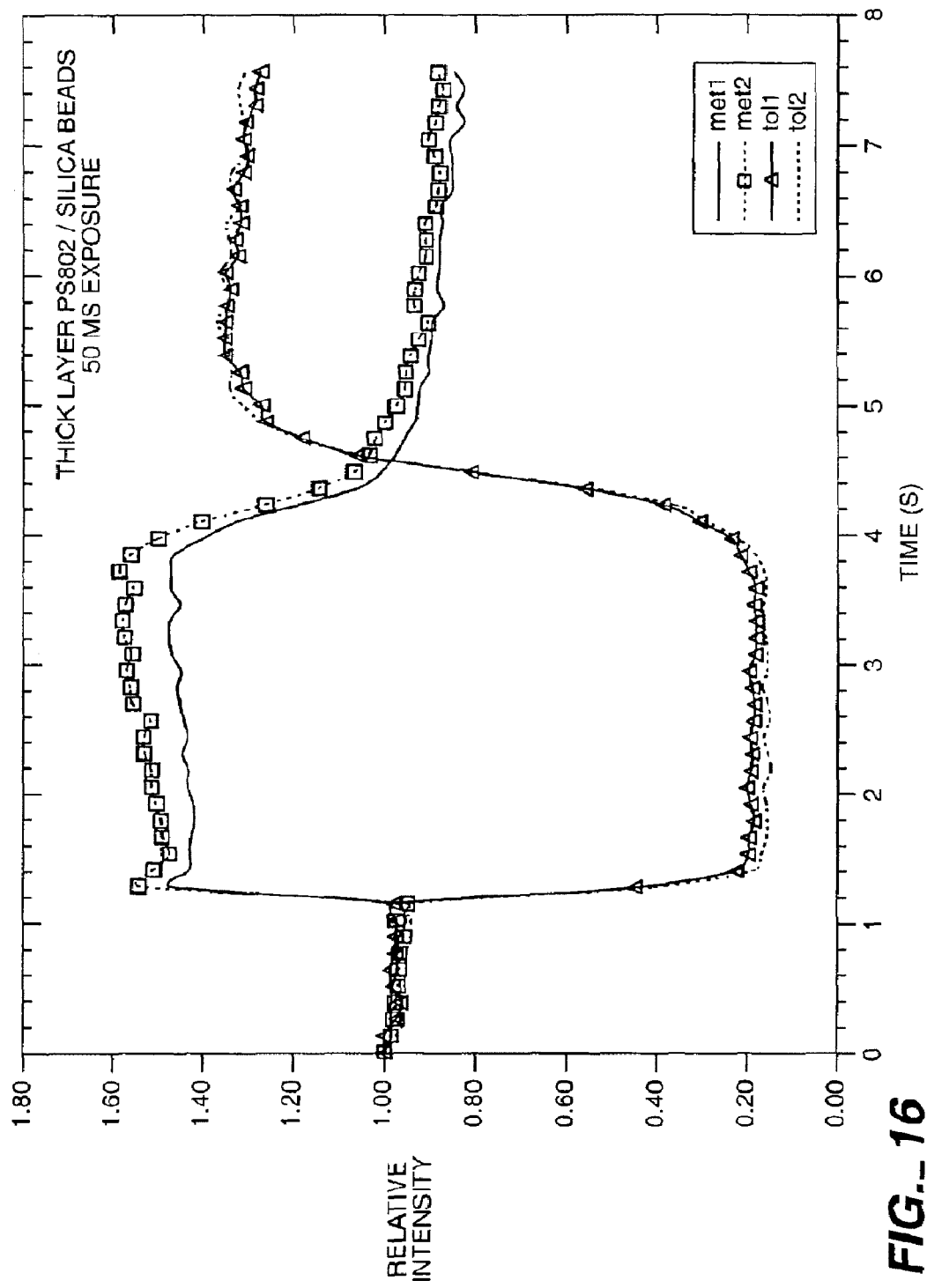
FIG. 16 compares the characteristic optical response signatures of two PS802 coated porous silica beads infiltrated with Nile Red dye upon exposure to toluene and methanol vapor.

| Figure | Rate (ms/frame) | Total No. of Frames |
|---|---|---|
| FIG. 14 | 155 | 60 |
| FIG. 15 | 155 | 60 |
| FIG. 16 | 124 | 60 |

A conventional air dilution olfactometer and vacuum-controlled vapor delivery system 500, as commonly known and used in olfactory research and described in Kauer, et al., *J. Physiol.* 272:495-516 (1977), was used to apply controlled pulses of analyte vapor and air carrier gas to either a sensor bead substrate or the distal end 212 of a fiber optic sensor array 100 containing an array of sensor beads 10 immobilized in microwells 250.

To produce a saturated vapor sample, generally, a stream of air carrier gas is passed through a 5 ml cartridge containing filter paper saturated with the analyte. Analyte dilutions are produced by adjusting the relative flow rates of saturated vapor and clean carrier gas streams. Typically, a flow rate of 100 ml/min is used for the combined gas flow to the sensor array. At this flow rate, a 2 second pulse would deliver approximately 3.3 ml of analyte vapor with carrier gas. In generally, depending on the analyte vapor pressure and dilution factor, vapor pulses contain between $10^{-7}$ to $10^{-5}$ mol of analyte.

The vapor pulse was typically delivered during the 11th through 30th frame, commencing on the 11th frame. The duration of the vapor pulse varied with the specific frame rate utilized and typically ranged between 2 to 3 seconds. Baseline control measurements were performed with high purity, Ultra Zero grade air. The air pulse measurements were performed to account for any bead responses due to the vapor carrier gas.

Data processing: Following the collection of a temporal series of sensor bead or sensor array images, segments are drawn, using IPLab image processing software (Signal Analytics, Vienna, Va.), over each pixel which corresponds to an individual fiber where the fiber is coupled to one sensor bead at its distal end. The mean fluorescence intensity was measured for each one of these segments in each frame in the sequence. This is done for both the vapor pulse responses and the baseline air pulse responses. Averages of multiple runs of each may be performed to improve data quality where needed. The air pulse data is then subtracted from the vapor pulse data to subtract the background due to air alone. The resulting data can be plotted to yield temporal intensity responses for all beads of interest. In a preferred embodiment, the sensor array data are used in a neural network analysis according to the method disclosed in White, et al, *Anal. Chem.* 68:2193-2202 (1996).

All data manipulation is performed within the IPLab program environment using simple operator scripts that call standardized image or data processing routines included with the software. These scripts and routines consist of a data collection portion and a data analysis portion.

In the data collection portion, there are three segments or loops as follows: Loop 1. This establishes the baseline fluorescence of each sensor. This loop can be shortened or extended to adjust to slower or faster response times of specific sensor beads or sensor arrays to certain analytes. For Examples 7 through 17, this loop was set between 5 to 10 frames.

Loop 2. This is the vapor exposure loop. A vapor pulse is applied just before this loop starts by way of a script command that sends a 5 volt pulse to an attached solenoid valve which switches a vacuum line off, thereby allowing a vapor sample to emit from the end of a nozzle. Typically, this loop is 20 frames in duration. In Example 7, a 10 frame duration was utilized.

Loop 3. This is a sensor recovery loop. Another 5 volt trigger pulse is sent to a solenoid which switches back to its initial position, causing the vacuum system to resume collection of the solvent vapor and carry it off to waste. Typically, this loop is of 30 frames duration. In Example 7, a 15 frame duration was utilized.

Data analysis: In the data analysis portion, pre-selected segments taken from a previously collected "focus" image are transferred to the sequence of images collected. These segments, drawn by the user, allow the mean pixel intensity to be measured in particular regions throughout the image field. Typically, they are drawn over individual pixels of a fiber optic sensor array, each of which contains a bead. The script then enters a loop that steps through each frame, measuring the mean pixel intensity within each segment, and placing the values in data columns. The resulting columns can then be plotted to yield the temporal response of each bead of interest. Before plotting, however, responses are "standardized" by dividing the data for each bead response by its first point. Thus, all responses can be normalized to start at a value of 1.0.

Redundancy: As shown in the Examples, the present invention shows that building redundancy into an array gives several significant advantages, including the ability to make quantitative estimates of confidence about the data and significant increases in sensitivity. Thus, preferred embodiments utilize array redundancy. As will be appreciated by those in the art, there are at least two types of redundancy that can be built into an array: the use of multiple identical sensor elements (termed herein "sensor redundancy"), and the use of multiple sensor elements directed to the same target analyte, but comprising different chemical functionalities (termed herein "target redundancy"). For example, for the detection of nucleic acids, sensor redundancy utilizes of a plurality of sensor elements such as beads comprising identical binding ligands such as probes. Target redundancy utilizes sensor elements with different probes to the same target: one probe may span the first 25 bases of the target, a second probe may span the second 25 bases of the target, etc. By building in either or both of these types of redundancy into an array, significant benefits are obtained. For example, a variety of statistical mathematical analyses may be done.

In addition, while this is generally described herein for bead arrays, as will be appreciated by those in the art, this techniques can be used for any type of arrays designed to detect target analytes. Furthermore, while these techniques are generally described for nucleic acid systems, these techniques are useful in the detection of other binding ligand/target analyte systems as well.

Bead response summing: In a preferred embodiment, sensor redundancy is used. In this embodiment, a plurality of sensor elements, e.g. beads, comprising identical bioactive agents are used. That is, each subpopulation comprises a plurality of beads comprising identical bioactive agents (e.g. binding ligands). By using a number of identical sensor elements for a given array, the optical signal from each sensor element can be combined and any number of statistical analyses run, as outlined below. This can be done for a variety of reasons. For example, in time varying measurements, redundancy can significantly reduce the noise in the system. For non-time based measurements, redundancy can significantly increase the confidence of the data.

In a preferred embodiment, a plurality of identical sensor elements are used. As will be appreciated by those in the art, the number of identical sensor elements will vary with the application and use of the sensor array. In general, anywhere from 2 to thousands may be used, with from 2 to 100 being preferred, 2 to 50 being particularly preferred and from 5 to 20 being especially preferred. In general, preliminary results indicate that roughly 10 beads gives a sufficient advantage, although for some applications, more identical sensor elements can be used.

Once obtained, the optical response signals from a plurality of sensor beads within each bead subpopulation can be manipulated and analyzed in a wide variety of ways, including baseline adjustment, averaging, standard deviation analysis, distribution and cluster analysis, confidence interval analysis, mean testing, etc.

In a preferred embodiment, the first manipulation of the optical response signals is an optional baseline adjustment. In a typical procedure, the standardized optical responses are adjusted to start at a value of 0.0 by subtracting the integer 1.0 from all data points. Doing this allows the baseline-loop data to remain at zero even when summed together and the random response signal noise is canceled out. When the sample is a vapor, the vapor pulse-loop temporal region, however, frequently exhibits a characteristic change in response, either positive, negative or neutral, prior to the vapor pulse and often requires a baseline adjustment to overcome noise associated with drift in the first few data points due to charge buildup in the CCD camera. If no drift is present, typically the baseline from the first data point for each bead sensor is subtracted from all the response data for the same bead. If drift is observed, the average baseline from the first ten data points for each bead sensor is substracted from the all the response data for the same bead. By applying this baseline adjustment, when multiple bead responses are added together they can be amplified while the baseline remains at zero. Since all beads respond at the same time to the sample (e.g. the vapor pulse), they all see the pulse at the exact same time and there is no registering or adjusting needed for overlaying their responses. In addition, other types of baseline adjustment may be done, depending on the requirements and output of the system used.

Once the baseline has been adjusted, a number of possible statistical analyses may be run to generate known statistical parameters. Analyses based on redundancy are known and generally described in texts such as Freund and Walpole, Mathematical Statistics, Prentice Hall, Inc. New Jersey, 1980, hereby incorporated by reference in its entirety.

In a preferred embodiment, signal summing is done by simply adding the intensity values of all responses at each time point, generating a new temporal response comprised of the sum of all bead responses. These values can be baseline-adjusted or raw. As for all the analyses described herein, signal summing can be performed in real time or during post-data acquisition data reduction and analysis. In one embodiment, signal summing is performed with a commercial spreadsheet program (Excel, Microsoft, Redmond, Wash.) after optical response data is collected.

In a preferred embodiment, cumulative response data is generated by simply adding all data points in successive time intervals. This final column, comprised of the sum of all data points at a particular time interval, may then be compared or plotted with the individual bead responses to determine the extent of signal enhancement or improved signal-to-noise ratios as shown in FIGS. 14 and 15.

In a preferred embodiment, the mean of the subpopulation (i.e. the plurality of identical beads) is determined, using the well known Equation 1:

$$\mu = \sum \frac{x_i}{n} \qquad \text{Equation 1}$$

In some embodiments, the subpopulation may be redefined to exclude some beads if necessary (for example for obvious outliers, as discussed below).

In a preferred embodiment, the standard deviation of the subpopulation can be determined, generally using Equation 2 (for the entire subpopulation) and Equation 3 (for less than the entire subpopulation):

$$\sigma = \sqrt{\frac{\sum (x_i - \mu)^2}{n}} \qquad \text{Equation 2}$$

$$s = \sqrt{\frac{\sum (x_i - \bar{x})^2}{n-1}} \qquad \text{Equation 3}$$

As for the mean, the subpopulation may be redefined to exclude some beads if necessary (for example for obvious outliers, as discussed below).

In a preferred embodiment, statistical analyses are done to evaluate whether a particular data point has statistical validity within a subpopulation by using techniques including, but not limited to, t distribution and cluster analysis. This may be done to statistically discard outliers that may otherwise skew the result and increase the signal-to-noise ratio of any particular experiment. This may be done using Equation 4:

$$t = \frac{\bar{x} - \mu}{s/\sqrt{n}} \qquad \text{Equation 4}$$

In a preferred embodiment, the quality of the data is evaluated using confidence intervals, as is known in the art. Confidence intervals can be used to facilitate more comprehensive data processing to measure the statistical validity of a result.

In a preferred embodiment, statistical parameters of a subpopulation of beads are used to do hypothesis testing. One application is tests concerning means, also called mean testing. In this application, statistical evaluation is done to determine whether two subpopulations are different. For example, one sample could be compared with another sample for each subpopulation within an array to determine if the variation is statistically significant.

In addition, mean testing can also be used to differentiate two different assays that share the same code. If the two assays give results that are statistically distinct from each other, then the subpopulations that share a common code can be distinguished from each other on the basis of the assay and the mean test, shown below in Equation 5:

$$z = \frac{\bar{x_1} - \bar{x_2}}{\sqrt{\frac{\sigma_1^2}{n_1} + \frac{\sigma_2^2}{n_2}}} \qquad \text{Equation 5}$$

Furthermore, analyzing the distribution of individual members of a subpopulation of sensor elements may be done. For example, a subpopulation distribution can be evaluated to determine whether the distribution is binomial, Poisson, hypergeometric, etc.

Target redundancy: In addition to the sensor redundancy, a preferred embodiment utilizes a plurality of sensor elements that are directed to a single target analyte but yet are not identical. For example, a single target nucleic acid analyte may have two or more sensor elements each comprising a different probe. This adds a level of confidence as non-specific binding interactions can be statistically minimized. When nucleic acid target analytes are to be evaluated, the redundant nucleic acid probes may be overlapping, adjacent, or spatially separated. However, it is preferred that two probes do not compete for a single binding site, so adjacent or separated probes are preferred. Similarly, when proteinaceous target analytes are to be evaluated, preferred embodiments utilize bioactive agent binding agents that bind to different parts of the target. For example, when antibodies (or antibody fragments) are used as bioactive agents for the binding of target proteins, preferred embodiments utilize antibodies to different epitopes.

In this embodiment, a plurality of different sensor elements may be used, with from about 2 to about 20 being preferred, and from about 2 to about 10 being especially preferred, and from 2 to about 5 being particularly preferred, including 2, 3, 4 or 5. However, as above, more may also be used, depending on the application.

As above, any number of statistical analyses may be run on the data from target redundant sensors.

One benefit of the sensor element summing (referred to herein as "bead summing" when beads are used), is the increase in sensitivity that can occur. As shown in Example 19, detection limits in the zeptomole range can be observed.

EXAMPLES

Example 1

Preparation of porous silica/Nile Red beads: Approximately 0.5 cm³ of nominally 3.2 micron diameter commercial porous silica beads were removed from a LUNA column (Phenomenex, Torrance, Calif.). Sample of beads were placed onto a filter paper and, using vacuum filtration, 0.5 mL of Nile Red (Eastman Kodak, Rochester, N.Y.) solution (1 mg/mL in toluene) was poured over beads. Nile Red was immediately taken up by silica beads, turning them a deep purple color. The beads were washed repeatedly with toluene to remove any excess, non-adsorbed Nile Red. The beads were dried on a watch glass overnight. Beads were then placed into microwells formed by etching a fiber optic bundle according to the method of the present invention.

Example 2

Preparation of PDPO polymer coated porous silica beads: A silanizing solution was prepared from 20 µL N-octadecyltriethyoxysilane in 980 µL of ethanol/water (95% ethanol, 5% ultrapure water with pH adjusted to 4.9 with acetic acid).

The LUNA porous silica beads of Example 1 were dispersed in an excess of silanizing solution for approximately 10 minutes, vortexing continuously. The particles were rinsed three times with ethanol and dried in a 120° C. oven, overnight for approximately 12 hours.

Stock solution of PDPO, poly(2,6-dimethyl-1,4-phenylene oxide), (Aldrich, Milwaukee, Wis.) and Nile Red was prepared from 0.09 g PDPO and 1.0 mL chloroform. After complete dissolution of the polymer, a 100 µL aliquot of 1 mg/mL nile red in chloroform was added. The resultant solution was vortexed continuously for uniform dispersion.

Excess PDPO/Nile Red was added to a small fraction of the silanized porous beads, approximately 100 µL polymer/dye solution to approximately 1 mg of beads. The sample was vortexed for approximately 3 hours then washed. Excess polymer dye was removed and the beads were then washed repeatedly with methylene chloride, two to three times, followed by a washing with 0.01% polyoxyethylene-sorbitan monolaurate, Tween 20 (J. T. Baker, Cleveland, Ohio), in water. The washed beads were collected in a solution of 0.01% Tween 20/ultrapure water. A single, small drop was placed on a microscope coverslip and allowed to dry protected from light.

Example 3

Preparation of Non-Porous Silica/Nile Red Beads Coated with Polysiloxane polymer: Commercially available non-porous 3.1 µm silica beads (Bangs Laboratory, Fishers, Ind.) were first silanized in excess silanizing solution, a 10% solution by volume of 3-(trimethoxysilyl)propyl methacrylate (Aldrich, Milwaukee, Wis.) in acetone, overnight. Excess silanizing solution was decanted and the beads were rinsed repeatedly, two to three times, with ultrapure acetone, vortexing and centrifuging between washes. The beads were soaked in excess Nile Red solution (1 mg/ml in toluene) for approximately 3 hours while vortexing so as to fully saturate the surface. The bead solution was centrifuged and excess dye solution was decanted. A mixture of 7.9 mg benzoin ethyl ether (Polysciences Inc., Warrington, Pa.), 250 microliters stock Nile Red in toluene and 250 microliters (15-20% acryloxypropyl-methylsiloxane) 80-85% dimethylsiloxane copolymer (Gelest Inc., Tullytown Pa.) were then added to the beads. The bead suspension was vortexed to uniformly coat the particles. The resultant suspension mixture was added dropwise to approximately 100 mL 0.1% Tween 20 in ultrapure water stirring at approximately 350 rpm. Polymerization was accomplished by ultraviolet excitation for 10 second durations for a total exposure of 30 seconds. The sample solution was stirred over night. The suspension was passed through a 230 micron sieve, followed by a 5 µm sieve. The filtrate was centrifuged at 3000 rpm for approximately 5 minutes and the beads were collected into centrifuge tubes and washed with 0.01% Tween 20 in ultrapure water. A single small drop was placed on a microscope coverslip and allowed to dry protected from light.

Example 4

Preparation of (15-20% acryloxypropylmethylsiloxane) 80-85% dimethylsiloxane copolymer beads with nile red: Approximately 25 mL of ultrapure water plus 25 mL ethanol were placed in a 100 mL round bottom flask and stirred with a stirbar at approximately 350 rpm. A mixture of 500 µL (15-20% acryloxypropylmethylsiloxane) 80-85% dimethyl-siloxane copolymer, 200 µL Nile Red solution (1 mg/ml in chloroform) and 250 µL methylene chloride was made and added dropwise to the stirred water/ethanol solution. A solution of 5.5 mg AIBN, N,N'-azobis-isobutyl nitrile (2,2'-azobis-2-methylproprio-nitrile)(Phaltz & Bauer, Inc.), in methylene chloride was added to the stirring dispersion. The mixture was degassed with argon for approximately one hour and then heated to approximately 70 degrees celcius. After approximately three hours of heating, 20 mL of 0.01% Tween 20 in ultrapure water was added to the mixture. Heating and stirring was continued for approximately 12 hours. The mixture was passed through 230 micron sieve, then solids collected from centrifugation at up to 5000 rpm. The solids were washed twice with methanol and then washed with 0.01% Tween 20 in ultrapure water. The resultant beads were collected in a solution of 0.01% Tween 20 in ultrapure water. A single drop of the bead suspension was placed on a microscope coverslip and allowed to dry protected from light.

Example 5

Nile red dyed poly(methylstyrene/divinyl benzene) beads: Approximately 1 mg of commercially available 3.15 µm polymer beads, 87% methyl styrene, 13% divinyl benzene with amine functionalized surface (Bangs Laboratories, Fishers, Ind.), was washed in 1 ml of methanol by vortexing, centrifuging at approximately 3000 rpm and decanting the solvent. The beads were transferred to brown vial and approximately 100 µL of Nile Red solution (1 mg/ml in toluene) was added. The sample was vortexed and placed on a wrist shaker to agitate overnight. The suspension was transferred to a microcentrifuge tube and washed with methanol until the decanted solvent was clear. The beads were collected in approximately 0.5 mL of a solution of 0.01% Tween 20 in ultrapure water. A single drop placed on a microscope coverslip and allowed to dry protected from light.

Example 6

Plasticizer modified poly(methylstyrene/divinyl benzene) beads with nile red incorporated: Approximately 1 mg of commercially available 3.15 µm polymer beads, 87% methyl styrene, 13% divinyl benzene with amine functionalized surface (Bangs Laboratories, Fishers, Ind.), were rinsed with methanol according to Example 5 and transferred to a brown vial. Approximately 2-40% by wt plasticizer to polymer solutions of plasticizers, tritolyl phosphate (TTP), triphenyl phosphate (TPP), and dibutyl phthalate (DBP) (Aldrich, Milwaukee, Wis.), with nile red solution (1 mg/mL in toluene) were added to samples of beads, covered, vortexed then shaken on wrist shaker for approximately 12 hours. The beads were transferred to microcentifuge tubes and washed with Nile Red in methanol, then repeatedly with methanol until the decanted solvent was clear. The beads were collected in a solution of 0.01% Tween 20 in ultrapure water. A single drop of the suspension was placed on a microscope coverslip and allowed to dry protected from light.

Example 7

The porous silica beads prepared by the method of Example 1 were evaluated to determine their characteristic optical response signature to toluene vapor following the experimental method described above. The results are presented in FIG. 9 where the temporal optical response of 62 individual bead sensors to a pulse of toluene vapor is shown.

Example 8

The poly(methylstyrene/divinyl benzene) beads prepared by the method of Example 5 were evaluated to determine their characteristic optical response signature to methanol vapor. The results are presented in FIG. 10 where the temporal optical response of 39 individual bead sensors to a pulse of methanol vapor is shown.

Example 9

The (15-20% acryloxypropylmethylsiloxane) 80-85% dimethylsiloxane copolymer beads prepared by the method of Example 4 were evaluated to determine their characteristic optical response signature to both toluene and methanol vapor. The results are presented in FIG. 11 where the temporal optical responses of an individual bead sensor to a pulse of toluene and a pulse of methanol vapor is shown.

Example 10

The PDPO polymer coated porous silica beads prepared by the method of Example 2 were evaluated to determine their characteristic optical response signature to both toluene and methanol vapor. The results are presented in FIG. 12 where the temporal optical responses of an individual bead sensor to a pulse of toluene and a pulse of methanol vapor is shown.

Example 11

Porous silica beads prepared by the method of Example 1 were incorporated into etched microwells on the distal end of a fiber optic bundle according to the method described above. The resultant sensor array was evaluated to determine the characteristic optical response signature of the bead subpopulation to ethyl acetate vapor. The results are presented in FIG. 13 where the temporal optical response of 218 individual bead sensors to a pulse of ethyl acetate vapor is shown.

Example 12

The signal summing method of the present invention was evaluated in analyzing the experimental measurements made on poly(methylstyrene/divinyl benzene) beads prepared by the method of Example 5 and tested by the method of Example 8. The results are shown in FIG. 14 where the normalized temporal optical response for a single sensor bead, Bead #1, is compared with the summed responses of all 39 beads tested.

As shown by FIG. 14, the signal summing method of the present invention significantly reduces the experimental noise encountered in a single sensor bead measurement and provides a substantial improvement, ten-fold or greater, in the signal-to-noise ratio of analytical measurements.

Example 13

The signal summing method of the present invention was evaluated in analyzing the experimental measurements made on poly(methylstyrene/divinyl benzene) beads prepared by the method of Example 5 and tested by the method of Example 8. The results are shown in FIG. 15 where the actual relative intensities of the temporal optical response for each of the 39 sensor beads is compared to relative intensity of the temporal optical response obtained from signal summing. As shown by FIG. 15, substantial signal enhancement is obtained by signal summing with a correspondingly significant improvement, up to a hundred fold, in the detection limit for target analytes.

Example 14

The polysiloxane coated porous silica beads prepared by the method of Example 3 were evaluated to determine their characteristic optical response signature to both toluene and methanol vapor. The results are presented in FIG. 16 where the temporal optical responses of two bead sensors to both toluene and methanol are shown. The results shown in FIG. 16 demonstrates the capability of this subpopulation of bead sensors to distinguish between two analytes of interest by utilizing the characteristic optical response signatures of the bead sensors to specific analytes.

Example 15

Figure 17:
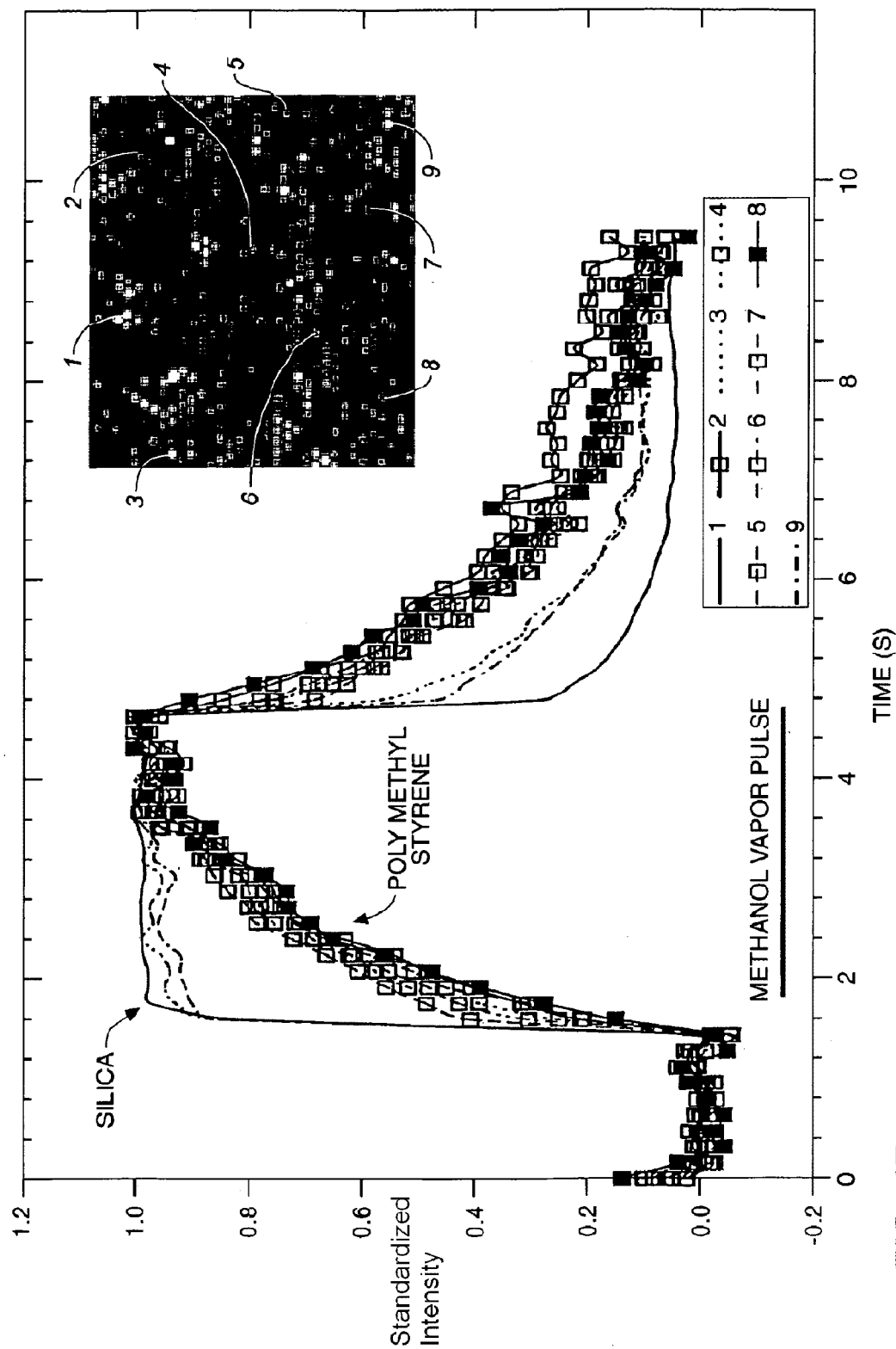
FIG. 17 compares the characteristic optical response signatures to methanol vapor which are used for decoding Nile Red infiltrated porous silica and PMS bead subpopulations in a self-encoded fiber optic sensor array of the present invention.
Figure 25:
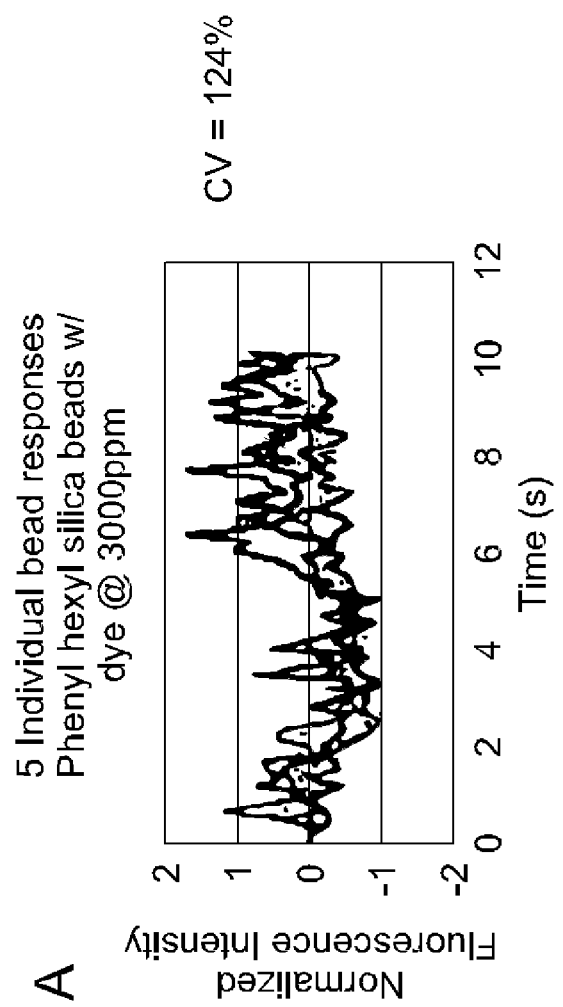
FIGS. 25A-G depict a number of individual experiments and the coefficient of variances.
Figure 25:
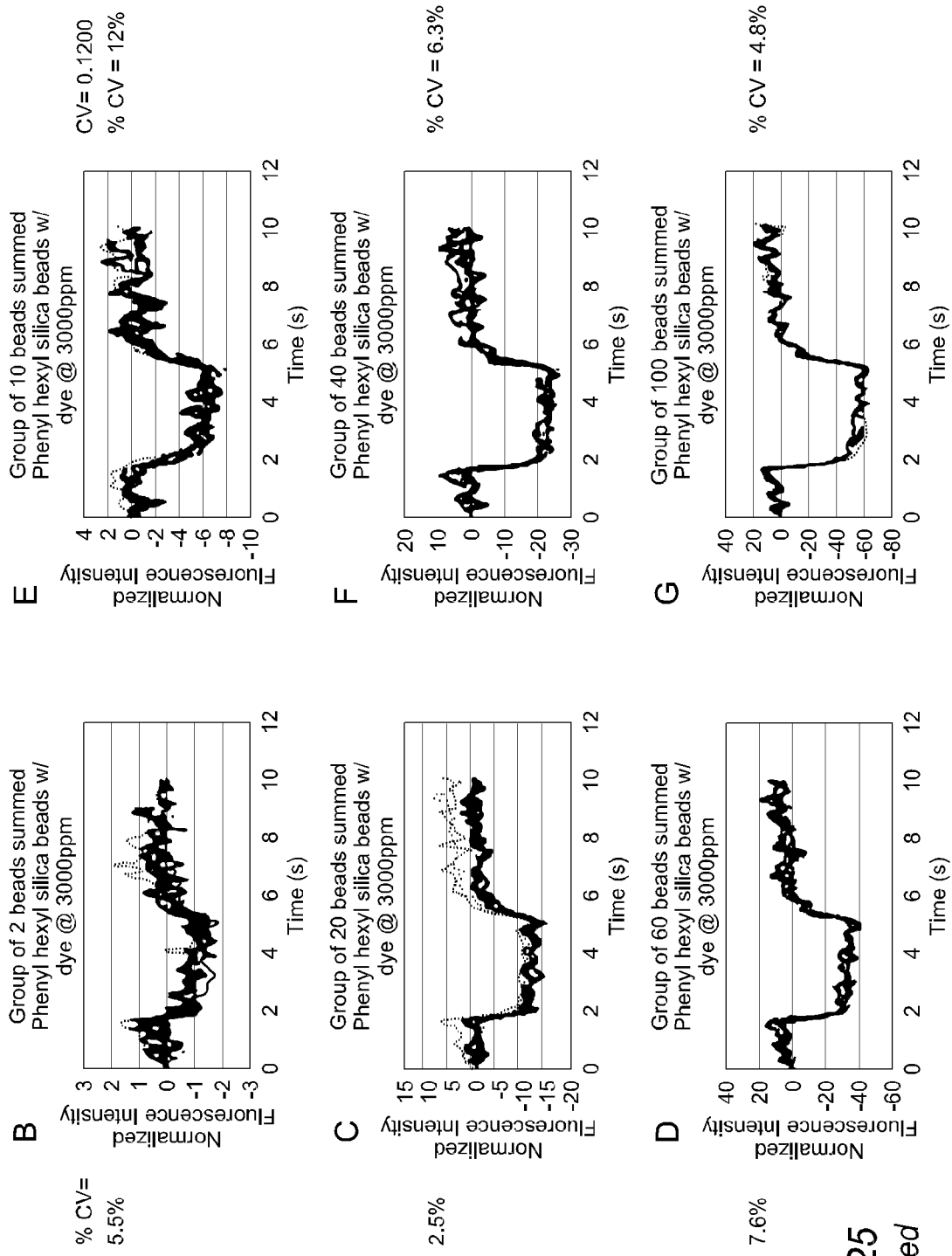

A 50/50 mixture of porous silica beads prepared by the method of Example 1 and poly(methylstyrene/divinyl benzene) beads prepared by the method of Example 5 were randomly dispersed and incorporated into etched microwells on the distal end of a fiber optic bundle according to the method of the present invention as described above. The resultant sensor array was evaluated to determine the characteristic optical response signature of the bead subpopulation to methanol vapor. An 535 nm excitation filter and 600 nm emission filter was used in this experiment. The results are presented in FIG. 17 where the normalized temporal optical response of 3 porous silica bead sensors and 6 PMS bead sensors to a pulse of methanol vapor is shown. In this example, the characteristic emitted light peak shapes of the bead subpopulations provide a distinguishable characteristic response signature for each subpopulation. FIG. 17 demonstrates the innovative self-encoding feature of the present invention where the identity and location of the beads is determined in a single measurement of a reference vapor analyte.

Example 16

The self-encoded fiber optic sensor array produced by the method of Example 15 was evaluated by measuring the characteristic temporal optical response signature of the porous silica and PMS sensor bead subpopulations of the array in response to a pulse of n-propanol vapor. The results are presented in FIG. 18 where the temporal optical response of 3 porous silica bead sensors and 6 PMS bead sensors to a pulse of n-propanol vapor is shown. In this example, the characteristic emitted light intensities of the bead subpopulations provide a distinguishable characteristic response signature for each subpopulation. FIG. 18 demonstrates the advantages of using the distinct characteristic temporal optical response signature of different bead subpopulations to detect a specific analyte of interest. Note that the identity and location of the bead sensors in the sensor array was decoded by the method of Example 15. By the combination of self-encoding the sensor array by the method of Example 15 and the sensor array measurement made by the method of the current Example 16, the sensor array was trained to detect and distinguish methanol from n-propanol.

Example 17

The self-encoded fiber optic sensor array produced by the method of Example 15 was evaluated by measuring the characteristic temporal optical response signature of the porous silica and PMS sensor bead subpopulations of the array in response to a pulse of toluene vapor. The results are presented in FIG. 19 where the temporal optical response of 3 porous silica bead sensors and 6 PMS bead sensors to a pulse of toluene vapor is shown. FIG. 19 demonstrates the advantages of using the characteristic temporal optical response signature of different bead subpopulations to detect a specific analyte of interest. Note that the identity and location of the bead sensors in the sensor array was decoded by the method of Example 15. By the combination of decoding the self-encoding the sensor array by the method of Example 15, the sensor array measurement made by the method of Example 16, and the sensor array measurement made by the method of the current Example 17, the sensor array was trained to detect and distinguish between the group of target analytes comprising methanol, n-propanol, and toluene.

Example 18

Samples of PS802 bead sensors produced by the method of Example 4, Poly methyl styrene/2% divinyl benzene bead sensors produced by the method of Example 5, and commercially available poly methyl styrene beads (Bangs Laboratory, Fishers, Ind.) were dispersed on a microscope coverslip substrate. Following equilibration of each bead subpopulation in air, each subpopulation was exposed to a pulse of saturated toluene vapor while illuminating the beads with excitation light energy. The changes in bead dimension due to the swelling response of each polymer type to toluene vapor was monitored using the apparatus of FIG. 7. The response of the bead was recorded by filming the time varying fluorescence image of the beads and capturing changes in bead image dimensions with a CCD camera. FIG. 20 illustrates the differences in swelling response of the three bead subpopulations by comparing the initial fluorescence image of each bead type in air with subsequent image of each bead type following exposure to toluene vapor. Such measurements of the swelling response characteristics of various polymer candidate materials is useful in prescreening bead sensor materials for use as bead sensor elements in the self-encoded sensor array of the present invention.

Example 19

The use of bead summing for sensitive detection. An array containing 25 oligonucleotide probes attached to encoded microspheres was made. Before attaching oligonucleotides to the microspheres, a family of dye-encoded microspheres was created. Fluorescent dyes were used to encode the microspheres. Europium(III)thenoyltrifluoro-acetonate-$3H_2O$ ($_{ex}/_{em}$=365/615) (Eu-dye), ($_{ex}/_{em}$=620/700) and 5-(and-6)-carboxytetramethyl-rhodamine, succinimidyl ester ($_{ex}/_{em}$=535/580) (TAMRA, SE) were chosen for this demonstration. The dyes were incorporated by exploiting the chemical properties of the amino-modified polystyrene microspheres as follows. 200-μL-aliquots of stock (1 mL of stock beads contains $5.8\times10^9$ beads in 0.01% merthiolate in water) 3.1 μm-diameter amine-modified poly(methylstyrene)divinylbenzene microspheres (Bangs Laboratories, Inc. Carmel, Ind.) were filtered and washed with dry THF then placed in a microcentrifuge tube. 200 μL of europium(III) thenoyltrifluoroacetonate-$3H_2O$ [Eu-dye (Acros)] dye in THF was added to the beads. Eu-dye concentrations of 0, 0.001, 0.01, 0.025, 0.05, 0.1, 0.5, and 1 M were used. The microsphere/dye suspension was shaken (VWR Vortex Genie II) for 2 h. The suspensions were filtered separately (Millipore Type HVLP) and washed thoroughly with MeOH. The beads were stored in 0.01% Tween (essential for preparation and storage to prevent the beads from clumping together) in ultrapure water until use.

Alternatively, external encoding was done. 10 μL of stock beads were rinsed (all rinsing procedures entailed placing the centrifuge tube containing the beads and solution into a microcentrifuge at 8000 rpm for 3 min, and liquid over the beads was removed using a pipette) with BT buffer (0.1 M boric acid, 0.1 M NaOH, 0.13 M $NaHCO_3$, 0.01% Tween, pH 9). The beads were suspended in 100 μL BT buffer then 5 μL of dye solution [Cy5 (Amersham) or TAMRA(Molecular Probes)] in DMF was added. Cy5 concentrations of 0, 0.01, 0.05, 0.1, 0.3 mM and TAMRA concentrations of 0, 0.1, 0.4, and 3 mM were used. The beads were shaken for 2 h then rinsed three times with BT buffer then three times with PBST buffer (0.01 M phosphate buffer saline, 0.01% Tween, pH 7.4).

The polystyrene microspheres swell in tetrahydrofuran (THF) enabling a dye to penetrate the microsphere and become entrapped when the microsphere contracts. The absorption and emission spectra of the dyes are not compromised within the microsphere's environment and their concentration remains constant over time. Eight distinguishable microsphere families were prepared by entrapping varying Eu-dye concentrations inside the microspheres. In addition to internal entrapment, the microspheres' amine-modified surface permitted coupling to amine-reactive dyes. Different concentrations of Cy5 and TAMRA were then attached to the surface amine groups of the eight Eu-dye beads. A library of 100 spectroscopically-distinguishable microsphere types was prepared using various combinations of the three dyes. Microsphere encoding was carried out prior to oligonucleotide attachment because reaction with the amine reactive dyes after probe attachment affected the hybridization reaction. On the other hand, the oligonucleotide probes on the surface of the microspheres are not affected by subsequent internal encoding with Eu-dye.

DNA attachment. After the encoded microsphere library was in hand, we functionalized each encoded microsphere with a different single stranded DNA probe. Sequences of each probe are shown in FIG. 21. A protocol used previously to create a single core fiber optic DNA array was modified to prepare the DNA-microsphere sensors.

DNA probes were synthesized with a 5'-amino-C6 modifier (Glen Research) in the Tufts Physiology Department using an ABI synthesizer. 20 nmol of the 5'-amino-terminal oligonucleotide probe were dissolved in 180 μL of 0.1 M sodium borate buffer (SBB pH 8.3). Oligonucleotide activation was initiated by adding 40 nmol of cyanuric chloride in 40 μL of acetonitrile. After 1 h, unreacted cyanuric chloride was removed by three cycles of centrifugal ultrafiltration (Microcon 3, Amicon) and recovered in 200 μL of 0.1 M SBB.

DNA functionalization. Five μL of stock beads were rinsed with 0.02 M phosphate buffer (pH 7). 150 μL of 5% glutaraldehyde in phosphate buffer was added to the beads. The beads were shaken for 1 h then rinsed three times with phosphate buffer. 150 μL of 5% polyethyleneimine (PEI) was then added to the beads. The beads were shaken for 1 h then rinsed three times with phosphate buffer then three times with 0.1 M SBB (sodium borate buffer, pH 8.3). 100

μL of 150 μM cyanuric chloride-activated oligonucleotide probe in SBB buffer was added to the beads and shaken overnight. The probe solution was removed and saved for reuse. The beads were then rinsed three times with SBB buffer. Remaining amine groups were capped with succinic anhydride to prevent non-specific binding. 100 μL of 0.1 M succinic anhydride in 90% DMSO, 10% SBB was added to the beads. The beads were shaken for 1 h then rinsed three times with SBB buffer then three times with TE buffer (10 mM Tris-HCL, pH 8.3, 1 mM EDTA, 0.1 MNaCl, 0.1% SDS).

When the cyanuric chloride-activated probes were attached directly to the amine-modified polystyrene microspheres detectable fluorescent signals were generated by hybridized labeled targets. However, by first modifying the microspheres with polyethyleneimine (PEI) before DNA functionalization the signal increased ten-fold because the number of attachment sites available was amplified (data not shown). Non-specific binding of the target to the amine-functionalized microsphere surface was prevented by capping unreacted amines with succinic anhydride. The resulting encoded probe-functionalized microspheres can be stored for months and mixed in any desired combination to create or alter the DNA sensor array.

Microsphere-based fiber-optic sensors. Recently, we reported an array consisting of randomly distributed independently addressable micron-bead-sensors using an imaging-optical-fiber substrate. This system employed imaging fibers consisting of six thousand individually clad fibers that were melted and drawn together to form a coherent, 500-μm diameter bundle. The compositional difference between the core and cladding of each fiber enables the cores to be etched selectively providing for the simultaneous formation of six thousand 3.5 μm-diameter wells in the surface of the fiber tip within seconds. See Michael et al., Anal. Chem. 70:1242 (1998); Bronk et al., Anal. Chem. 67:2750 (1995) and Pantano et al., Chem. Materials 8:2832 (1996), all of which are incorporated by reference.

Microwell formation. 500 μm-diameter imaging fiber bundles containing $6 \times 10^4$ individual fibers were chemically etched according to a previously detailed procedure; see Pantano et al. Chem. Materials 8:2832 (1996).

Array formation. Five μL of probe-functionalized beads were stored in 40 μL of TE buffer. After selecting the desired probe-functionalized microspheres, 1 μL of each bead solution was placed in a microcentrifuge tube and vortexed. 0.05 μL of this mixture was placed onto the distal face of the imaging fiber containing the microwells. After evaporation of the solvent (approximately 3 min), the distal tip of the fiber is wiped with an anti-static swab to remove excess beads. When a new sensor is desired, sonicating the fiber tip for 3 min will regenerate the substrate.

Individual beads settle spontaneously into the wells as the water droplet evaporates to produce a randomly-distributed array of thousands of microsphere sensors. Excess microspheres are removed from the fiber tip while electrostatic interaction between the beads and the wells holds each microsphere in place.

Controlling array formation. One of the primary advantages of this system is the ability to alter the types of microspheres contained in an array. Each milliliter of stock solution contains approximately $6 \times 10^9$ microspheres enabling functionalization of billions of beads at once. Even after a 20× dilution, a 1 μL volume of microsphere solution contains enough beads to produce hundreds of different arrays. The density of microspheres in solution can control the number of occupied wells. With dilute solutions, empty wells remain after the initial array production. Additional microspheres bearing different probes can be added to the unoccupied sites or to the original solution at any time to create a more diverse array. If a different selection of beads is desired, sonicating the fiber tip removes all of the beads from the wells, enabling a new sensor array to be made in the same substrate.

Optical imaging and analysis system. Coupling the imaging fiber bundle to a detection system with a CCD camera enables us to resolve each fiber independently, and hence the microsphere residing in the well at each fiber tip, while simultaneously viewing the entire array. Hybridization was visualized using fluorescent-labeled complementary targets. The microspheres bearing a fluorescent signal due to a hybridized target are selected and the identity of the probe on each bead is determined by the microspheres' spectroscopic signature.

Analysis set-up and protocol. The imaging system, described previously, consists of a light source, inverted microscope, and a modified Olympus epifluorescence microscope/charge coupled device camera (Photometrics PXL). A fiber chuck held the imaging fiber in a fixed position while electronically controlled filter wheels switch between the analytical wavelength and the encoding wavelengths, enabling complete analysis and identification of the microspheres within minutes. Excitation light was sent into the proximal tip of the imaging fiber and emission from the fluorescing molecules is captured and directed onto the CCD camera detector. Fluorescence measurements were acquired and analyzed using commercially available IPLab software (Signal Analytics).

The fiber was not removed from the imaging system during testing, rinsing, or regeneration steps. The proximal tip of the fiber was secured in the fiber chuck of the imaging system and all solutions were brought to the fiber's distal tip which housed the microbead sensors. Images acquired immediately prior to each test while the fiber tip was in buffer were subtracted from the response images. Background signals from empty wells were then subtracted from signals generated during each test.

Hybridization in real time. Each microsphere's fixed position made possible a hybridization study in real time. A DNA array containing identical beads was placed on the imaging system. The distal tip of the fiber bearing the microsphere sensors was placed in a labeled-target solution. Emission from hybridizing labeled-target was captured every minute for several minutes. In the small region of the imaging fiber selected for this study, 70 microspheres held the probe complementary to the target in solution. Each microsphere was monitored independently and simultaneously. Signals from 40 beads were averaged to provide kinetic data. At relatively high concentrations of target, hybridization could be detected immediately, as seen by the steep slope of the data. While the sensor remained on the imaging system it was regenerated by dipping the fiber tip into a room-temperature formamide solution. The same microspheres were assayed several times by placing the regenerated fiber into the target solution and repeating the experiment. Consecutive studies show that the same sensor can be used for multiple tests.

A background fluorescence image was acquired at wavelengths specific to fluorescein (excitation 490 nm emission 530 nm) with the fiber's distal tip in buffer. The fiber's distal tip was then placed in 4 μL of fluorescein-labeled target solution and one image was acquired every minute for 10 min. Subsequently, the fiber was dipped in 90% formamide in TE buffer at room temperature (rt) to regenerate the sensor and a background image was taken with the fiber in buffer. The fiber was again placed in the target solution where images were acquired for another 10 min interval.

Reproducibility and regenerability. The signal from the microspheres returns to background and the sensor can be used for multiple analyses with comparable results. 100 assays of the same DNA array sensor were performed over several days. The average of fluorescent signals obtained after hybridization with an array containing two bead types was done. The low standard deviation exemplifies the robust nature of the DNA microspheres. At periodic intervals during the 100-assay test, microspheres carrying the second probe in the same array were tested to see if regeneration affected their response. Both probe types showed no compromise in response during the tests. Each array can be used for multiple tests since it is regenerated quickly and easily. The ability to reuse a single array hundreds of times significantly increases throughput and decreases the cost of each array.

The fiber's distal tip was placed in 4 µL of labeled-target solution for 5 min, rinsed with TE buffer, and a fluorescence image was acquired for 5 s. The fiber tip was then dipped in 90% formamide in TE (rt) to remove any hybridized target and regenerate the sensor. This procedure was repeated 100 times using the IL2 target and 5 times (intermittently during the IL2 tests) using the IL6 target.

Kinetic Study. The fiber tip was placed in the target solution for a given time, rinsed with TE and a fluorescence image was acquired with the sensor in buffer. After data acquisition, the fiber was placed back in the target solution for a given time, rinsed and analyzed in buffer. The sensor was monitored at elapsed times of 10 s, 20 s, 30 s, 1 min, 2 min, 3 min, 4 min, 5 min and 10 min. After a plateau was reached, the sensor was regenerated by dipping in a 90% formamide solution in TE (rt) and the test was repeated using a different concentration of target solution.

Microsphere sensitivity. The fiber's distal tip was placed in 4 µL of target solution until the hybridization signal to noise ratio was three. The signal was monitored after rinsing the fiber tip with TE buffer and acquiring a fluorescence image for 5 s while the fiber tip was in buffer. For the hour-long assays, a 0.6 mL centrifuge tube was filled and capped. A hole was drilled in the cap to enable the fiber tip to be placed in the target solution while preventing evaporation.

Sensitivity with an intensified CCD camera. The 21-mer cystic fibrosis oligonucleotide probe and complement with F508C mutation (5'-TAT CAT CTG TGG TGT TTC CTA-3') (SEQ ID NO:11) were used for this study. The 5'-aminoterminal oligonucleotide probe was activated with 100 times excess of cyanuric chloride. The microspheres were incubated with 400 M cyanuric chloride-activated oligonucleotide. The fluorescein-labeled target was dissolved in 6× saline sodium phosphate EDTA buffer (SSPE) containing 0.1% SDS. The fiber's distal tip was placed in 10 µL of target solution during hybridization with occasional stirring. The distal tip was then washed with 6×SSPE and a fluorescence image was acquired with a Pentamax ICCD camera (Princeton Instruments) for 1 s while the fiber tip was in 120 µL of 6×SSPE.

Preparation of 10 to 125 bp ssDNA. One hundred µg of sperm DNA (587 to 831 base pairs) was incubated with nuclease S1 [3.96 U/µL (Gibco-BRL)] at 37° C. for 1 h in 30 mM sodium acetate buffer (pH 4.6) with 30 mM sodium chloride and 1 mM zinc acetate. After the reaction, the enzyme was removed from the DNA preparation by extraction with phenol:chloroform:isoamyl:alcohol (25:24:1, equilibrated to pH 8.0). DNA between 10 and 125 base pairs was recovered by ultrafiltration with Microcon 3 (10 bp cut-off) and Microcon 50 (125 bp cut-off). The DNA was quantified with OligoGreen single-stranded DNA quantitation reagent (Molecular Probes).

Multiplex Analysis. Images were acquired for 1 s and 0.5 s at wavelengths specific to each encoding dye. A 365 nm excitation filter and a 600 nm long pass emission filter were used for the Eu-dye. A 620 nm excitation filter and a 670 nm emission filter were used for the Cy5 dye. A 530 nm excitation filter and a 580 nm emission filter were used for the TAMRA. The images acquired at the three wavelength pairs were used to positionally register each microsphere sensor.

The fiber's distal tip was placed in a target solution for 5 min, rinsed with TE buffer, and fluorescence images were acquired for 5 s while the fiber was in buffer. Overlay segments were drawn to select the beads bearing a hybridization signal using IPLab software. These overlay segments were copied and pasted onto each of the encoding images and the selected beads' identity was determined. The sensor was regenerated as described above and this procedure was repeated for each of the target solutions.

Hybridization specificity in a multiplex assay. To demonstrate this microsphere array system, we first selected seven probes used in previous work (sequences 1-7 of FIG. 21). The DNA sequences chosen for the array were designed to be completely specific at room temperature. The signals at two of the three encoding wavelengths is used to positionally register the microspheres. After registration at the encoding wavelengths, the array is ready for use. The fiber tip is dipped into a fluorescent-labeled target solution. After a specified time, the fiber tip is removed from the target solution, rinsed with buffer, and placed in buffer solution. Microspheres bearing a complementary probe display a fluorescent signal due to the hybridized labeled target. Completely specific hybridizations for seven different targets in an array were observed. Replicates of each bead type located randomly within the array yield redundant information which contributes to the array's reliability. FIG. 22 shows the accuracy of the system to correctly identify the target.

We have also demonstrated single-base-pair mismatch differentiation by conducting the hybridization at 53° C. (data not shown). Similar signals are generated from the hybridized complementary fluorescent-labeled target at room temperature and at the elevated temperature. The hybridized single base mismatch fluorescent-labeled target produced 50% less signal than the complementary target at room temperature. At the elevated temperature, the signal from the hybridized single base mismatch target was at the background level.

After the initial demonstration, we selected 25 sequences from disease-related genes (oncogenes and cystic fibrosis) and disease states (lymphocyte and cytokine expression) which are completely specific at room temperature (FIG. 21). An array sensor was created with the 25 different probes each attached to a different encoded microsphere. After registration, the array was interrogated with each of the 25 target solutions as described above with sensor regeneration between each test. Approximately 20% (1295 out of 6000) of the wells were occupied with an average of 50 replicates of each bead type in the array. The resulting data (FIG. 23) enabled the correct identification of each target solution.

Hybridization at elevated temperature. An array was created using a 450 mm long fiber. The proximal end of the fiber was connected to the imaging system and the distal end was held in a vertical micropositioner. The buffer and target temperatures were controlled by a water bath. Testing was performed as described above.

Sensitivity of the microspheres. There are three aspects to sensitivity: sample volume, target concentration, and absolute number of target molecules. The smaller the volume required, the less a sample needs to be amplified for detection since the same number of absolute target molecules in a smaller volume generates a higher local concentration. Sample volumes as small as 4 µL are required with this system since only the tip of the 500 µm-diameter fiber is dipped into the solution. Typically, we use 10 µL volumes for easier handling and to avoid evaporation.

In order to evaluate the concentration sensitivity of the array, an intensified CCD (ICCD) camera was used. The camera is fitted with a microchannel plate image intensifier that is optically coupled to a CCD array. By employing the ICCD camera, the time needed to analyze the lowest concentrations was significantly reduced relative to an unintensified camera. For comparison, at 100 fM, an unintensified camera took 4 h to detect a signal. To determine the sensitivity for a given target, an array was prepared consisting of 500 identical beads. We reasoned that the sensitivity obtained by observing multiple beads in the array would provide us with a signal to background advantage. To our satisfaction, this advantage was borne out.

Sensitivity experiments were carried out as follows: the array was hybridized in 10 µL solutions containing progressively decreasing concentrations of labeled target. The lowest concentration evaluated was 1 fM. At various times, the array was taken out of the hybridization solution, rinsed, and a fluorescence image was collected. The array was then placed back into the hybridization buffer. After hybridization, the array was dehybridized with formamide and five background measurements were taken in 6×SSPE. ROI's from 10 or 100 beads in the five images were averaged to provide the mean background. The mean background values were subtracted from the fluorescence intensities of the various numbers of beads. Individual beads exhibited significant variablilty such that it was not possible to ascertain whether or not a signal was present. On the other hand, summing signals from multiple beads provided detectable signals. The average signal of ten beads gave a 7% CV while 100 beads provided more precise average values with 3% CV. Results from three representative sets of ten beads for the complementary target and two non-complementary targets are presented in FIG. 24. The hybridization time was determined when the signal was over three times the standard deviation of the background signals (>3 sd). Using this criterion, the microsphere-fiber-optic system is able to detect a 1 fM target solution using a 10 µL volume in 1 hour.

Both 10 and 100 beads from a total of 500 beads in the array were selected and monitored. In a 1 fM target solution, 10 µL contains ca. 6000 DNA molecules. With 500 identical beads in the array giving a signal, each bead would be expected to contain, on average, ca. 12 labeled target molecules on its surface. To confidently attest to the generation of signal, the average signal of at least ten beads was needed. Therefore, this system can give sufficient signal with only 120 molecules.

FIG. 24 shows the specificity of the F508C oligonucleotide array to 1 fM target concentrations. Each target was tested three times. The non-specific binding signal was always less than three times the sd of the background. Hybridization of 1 fM target solution was also monitored using microspheres made with 4 times diluted cyanuric chloride activated oligonucleotide. In this case, no signal was obtained after 1 h demonstrating that the amount of probe on the surface of the microspheres plays an important role in the sensitivity.

Analyses were performed in the presence of single-stranded salmon sperm DNA [587 to 831 base pairs (Sigma)]. With up to 10 ng of sperm DNA, there was no observable inhibition in target hybridization. The analyses were also done with 10 ng of shorter lengths of sperm DNA (10 to 125 base pairs). In this case, hybridization of 1 and 10 fM target solution was inhibited. However, the same signal could be observed (>3 sd) with an additional 30 minutes of incubation time more than the values given in FIG. 23.

Since fluorescein was used to label the DNA targets, we selected encoding dyes with spectral properties that would not overlap with the fluorescein spectrum. Covalently binding these dyes to the surface of the amine-functionalized microspheres yielded stable and reproducible signals. Unfortunately, such surface encoding reduces the number of amines available for the cyanuric chloride-activated oligonucleotide probe. Therefore, the concentrations of the dyes were optimized to enable sufficient signals from both the encoding dyes and the hybridized target. The finite number of surface amine groups reduces the range and number of dye combinations that can be generated with an external-labeling scheme. To increase the number of encoded microspheres, dyes also can be entrapped inside the bead. Lanthanide dyes are suitable for such internal encoding. The dyes' spectra are not compromised and their intensity remains constant once inside the microsphere.

The DNA sequences employed in this work play important roles in the immune system. Not only is detection of these sequences important, but quantification of their expression can provide relevant clues in expression pattern during different disease states. Competition between labeled and unlabeled targets and kinetic rates of hybridization are methods used to quantitate analytes of interest. Single base mismatches are also an important area in genomic research. The microsphere fiber optic array completely discriminates between single base pair mismatches at elevated temperatures.

This microarray has the shortest total assay time relative to other high density DNA analysis systems and can monitor hybridization directly in the target solution. The high density of probes on each bead and the small bead size contribute to the short analysis time and sensitivity of the system. DNA samples presently require PCR amplification for analysis. Standard PCR starts with $10^2$ to $10^5$ copies of template. The DNA microbead array is capable of detecting 6000 target molecules. This result shows that DNA detection can be done without PCR amplification. At first, this result seems to defy logic; a standard white light source, camera, and optics are all employed. This level of sensitivity generally requires lasers, confocal optics and avalanche photodiodes. If we consider, however, that 12 molecules confined to a well volume (bead and liquid) of approximately 30 fL provides a local concentration of 1 nM, it becomes easy to understand why we are able to detect such small numbers of molecules. Nanomolar concentrations of fluorescence can be detected readily by the optical system. Thus, confining a small number of molecules to a small volume reduces the uncertainty of finding such low absolute molecule numbers by providing a relatively high local concentration. Bead replicates improve the confidence level even further. Longer strands of DNA that are typically in template DNA did not affect the sensitivity of the system. It can be concluded that the presence of a target sequence can be determined in a genomic DNA solution without PCR amplification.

The DNA microarray presented here has smaller feature sizes and higher packing densities compared to other DNA arrays. We have demonstrated the fiber optic microarray using a 500 μm-diameter imaging fiber with well diameters of 3.5 m. Fibers have also been tapered to produce nanometer scale wells serving as host to nanometer-diameter beads. Using longer fibers, the microarray sensor tp can be brought to the sample and used to sequentially test multiple solutions. Utilizing the imaging fiber's remote sensing capabilities, arrays with nanometer dimensions potentially can be used for direct intracellular analysis.

The advantages of this high-density randomly-distributed micrometer-sized high-resolution microsphere-based DNA array include cost effective production of the microbead array in seconds, high throughput analysis, easy replacement or addition with other microspheres when different testing is desired and facile regeneration of the sensor and substrate. In addition, the array can be brought to the sample solution rather than the solution being brought to the array. We are presently working on improving the sensitivity of the system to further reduce amplification requirements. With appropriate modifications, this general approach can be applied to the fabrication of libraries containing combinatorial peptides, antibodies, and other molecules. While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of statistically analyzing response signals obtained from a sensor element array to determine the statistical validity of said response signals, said method comprising:
   a) providing an array comprising a population of sensor elements at a density of least 20,000 sensor elements per 1 mm$^2$, said population of sensor elements comprising a plurality of subpopulations of sensor elements, the plurality of subpopulations of sensor elements comprising a first subpopulation comprising sensor elements having the same first bioactive agent and a second subpopulation comprising sensor elements having the same second bioactive agent;
   b) contacting said array with a composition comprising at least a target analyte, thereby producing a response signal at said sensor elements of at least one of said first and second subpopulations;
   c) obtaining individual response signals from 5 to 100 separate sensor elements from at least one of said first and second subpopulations; and
   d) performing a statistical analysis on said response signals from at least one of said first and second subpopulations, whereby statistical validity of said response signals is determined.

2. The method of claim 1, wherein said sensor elements are beads and said array comprises subpopulations of beads dispersed on a substrate.

3. The method of claim 2 wherein said substrate is a fiber optic bundle.

4. The method of claim 2 further comprising identifying the location of sensor element within each sensor subpopulation within the array.

5. The method according to claim 2, further comprising determining outlying beads and excluding outlying beads from said subpopulation.

6. The method according to claim 2, wherein said substrate is selected from the group consisting of glass and plastic.

7. The method according to claim 1, wherein at least one of said bioactive agents is a nucleic acid.

8. The method according to claim 7, wherein said nucleic acid is 25 nucleobases in length.

9. The method according to claim 7, wherein said nucleic acids comprise nucleic acid pairs, said nucleic acid pairs having the same sequence at all but one nucleotide position.

10. The method according to claim 1, wherein at least one of said bioactive agents is a protein.

11. The method according to claim 1, wherein said statistical analysis comprises calculating the mean of at least said response signals from said first of said plurality of subpopulations.

12. The method according to claim 1, wherein said statistical analysis comprises calculating the standard deviation of at least said response signals from said first of said plurality of subpopulations.

13. The method according to claim 1, further comprising evaluating the statistical validity of said response signals.

14. The method according to claim 1, further comprising performing a second statistical analysis on said response signals.

15. The method according to claim 14, wherein said second statistical analysis comprises evaluating said measurements using confidence intervals.

16. The method according claim 14, wherein said second statistical analysis comprises using said response signals to perform hypothesis testing.

17. The method according to claim 1, further comprising comparing said statistical analysis of response signals obtained from at least two subpopulations.

18. The method according to claim 17, herein said statistical analysis comprises performing a cluster analysis of response signals from each of said subpopulations.

19. The method according to claim 1, wherein individual response signals from 5 to 20 separate response elements are obtained.

20. The method according to claim 1, wherein individual response signals from roughly 10 separate response elements are obtained.

21. The method according to claim 1, wherein individual response signals from 10 separate response elements are obtained.

22. The method according to claim 1, wherein said sensor elements are attached to a planar substrate.

23. The method according to claim 22, wherein said composition does not flow-through said substrate.

24. The method according to claim 22, wherein said sensor elements are arranged in a regular pattern addressable in the X-Y coordinate plane.

25. The method according to claim 22, wherein said sensor elements are randomly distributed on said planar substrate.

26. The method according to claim 22, wherein said planar substrate is selected from the group consisting of glass and plastic.

27. The method according to claim 22, wherein said planar substrate is approximately the dimensions of a microscope slide cover slip.

28. The method according to claim 1, wherein said target analyte is present in solution.

29. The method according to claim 28, wherein said solution is applied directly to said sensor elements.

30. The method according to claim 29, wherein said sensor elements are immersed in said solution.

31. The method according to claim 30, wherein said sensor elements are immersed in said solution by dipping the sensor elements in said solution.

* * * * *

UNITED STATES PATENT AND TRADEMARK OFFICE
CERTIFICATE OF CORRECTION

PATENT NO. : 7,348,181 B2 Page 1 of 1
APPLICATION NO. : 09/287573
DATED : March 25, 2008
INVENTOR(S) : Walt et al.

It is certified that error appears in the above-identified patent and that said Letters Patent is hereby corrected as shown below:

Page 2, Column 2 (Foreign Patent Documents), Line 4, which reads "WO03/002979", should read -- WO03/02979 --

Column 1, line 7, after "U.S. application" delete "U.S. application" (second occurrence)

Column 1, line 8, delete "1997" and insert -- 1997, now U.S. Patent No. 7,115,884, -- therefor Column 61, line 32, in Claim 4, after "of" insert -- each --

Column 62, line 16, in Claim 18, delete "herein" and insert -- wherein -- therefor Signed and Sealed this Twenty-third Day of September, 2008

JON W. DUDAS
*Director of the United States Patent and Trademark Office*

SEQUENCE LISTING

<160> NUMBER OF SEQ ID NOS: 31

<210> SEQ ID NO 1
<211> LENGTH: 29
<212> TYPE: DNA
<213> ORGANISM: Artificial Sequence
<220> FEATURE:
<223> OTHER INFORMATION: Probe

<400> SEQUENCE: 1
tttttttttc aacttcatcc acgttcacc                29

<210> SEQ ID NO 2
<211> LENGTH: 33
<212> TYPE: DNA
<213> ORGANISM: Artificial Sequence
<220> FEATURE:
<223> OTHER INFORMATION: Probe

<400> SEQUENCE: 2
tttttttttt tttggcttct cttggctgtt act            33

<210> SEQ ID NO 3
<211> LENGTH: 35
<212> TYPE: DNA
<213> ORGANISM: Artificial Sequence
<220> FEATURE:
<223> OTHER INFORMATION: Probe

<400> SEQUENCE: 3
tttttttttt tttaaccgaa tcccaaactc accag          35

<210> SEQ ID NO 4
<211> LENGTH: 31
<212> TYPE: DNA
<213> ORGANISM: Artificial Sequence
<220> FEATURE:
<223> OTHER INFORMATION: Probe

<400> SEQUENCE: 4
tttttttttt ttccactgct tcccctctg t               31

<210> SEQ ID NO 5
<211> LENGTH: 33
<212> TYPE: DNA
<213> ORGANISM: Artificial Sequence
<220> FEATURE:
<223> OTHER INFORMATION: Probe

<400> SEQUENCE: 5
tttttttttt ttgttgggtc agggqtggtt att                33

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
tgaacgtgga tgaagttg                18

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
agtaacagcc aagagaaccc aaa                23

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
ctggtgagtt tgggattctt gta                23

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
acagaggggg aagcagttgg                20

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
aataaccacc cctgacccaa c                21

<210> SEQ ID NO 11
<211> LENGTH: 21
<212> TYPE: DNA
<213> ORGANISM: Homo sapiens

<400> SEQUENCE: 11
tatcatctgt ggtgtttcct a                21

<210> SEQ ID NO 12
<211> LENGTH: 21
<212> TYPE: DNA

```
<213> ORGANISM: Artificial Sequence
<220> FEATURE:
<223> OTHER INFORMATION: Probe

<400> SEQUENCE: 12
tcaacttcat ccacgttcac c                                              21

<210> SEQ ID NO 13
<211> LENGTH: 21
<212> TYPE: DNA
<213> ORGANISM: Artificial Sequence
<220> FEATURE:
<223> OTHER INFORMATION: Probe

<400> SEQUENCE: 13
tgggttctct tggctgttac t                                              21

<210> SEQ ID NO 14
<211> LENGTH: 23
<212> TYPE: DNA
<213> ORGANISM: Artificial Sequence
<220> FEATURE:
<223> OTHER INFORMATION: Probe

<400> SEQUENCE: 14
tacaagaatc ccaaactcac cag                                            23

<210> SEQ ID NO 15
<211> LENGTH: 20
<212> TYPE: DNA
<213> ORGANISM: Artificial Sequence
<220> FEATURE:
<223> OTHER INFORMATION: Probe

<400> SEQUENCE: 15
ccaactgctt cccctctgt                                                 20

<210> SEQ ID NO 16
<211> LENGTH: 21
<212> TYPE: DNA
<213> ORGANISM: Artificial Sequence
<220> FEATURE:
<223> OTHER INFORMATION: Probe

<400> SEQUENCE: 16
gttgggtcag gggtggttat t                                              21

<210> SEQ ID NO 17
<211> LENGTH: 15
<212> TYPE: DNA
<213> ORGANISM: Artificial Sequence
<220> FEATURE:
<223> OTHER INFORMATION: Probe

<400> SEQUENCE: 17
ggagctggtg gcgta                                                     15

<210> SEQ ID NO 18
<211> LENGTH: 10
<212> TYPE: DNA
<213> ORGANISM: Artificial Sequence
<220> FEATURE:
<223> OTHER INFORMATION: Probe

<400> SEQUENCE: 18
ccggcggtgt                                                           10
```

```
<210> SEQ ID NO 19
<211> LENGTH: 16
<212> TYPE: DNA
<213> ORGANISM: Artificial Sequence
<220> FEATURE:
<223> OTHER INFORMATION: Probe

<400> SEQUENCE: 19
cattatactt gtagag                                              16

<210> SEQ ID NO 20
<211> LENGTH: 15
<212> TYPE: DNA
<213> ORGANISM: Artificial Sequence
<220> FEATURE:
<223> OTHER INFORMATION: Probe

<400> SEQUENCE: 20
tgtagaatta tcttc                                               15

<210> SEQ ID NO 21
<211> LENGTH: 21
<212> TYPE: DNA
<213> ORGANISM: Artificial Sequence
<220> FEATURE:
<223> OTHER INFORMATION: Probe

<400> SEQUENCE: 21
cctctatact ttaacgtcaa g                                        21

<210> SEQ ID NO 22
<211> LENGTH: 21
<212> TYPE: DNA
<213> ORGANISM: Artificial Sequence
<220> FEATURE:
<223> OTHER INFORMATION: Probe

<400> SEQUENCE: 22
aagtttaacc tataccctgt c                                        21

<210> SEQ ID NO 23
<211> LENGTH: 16
<212> TYPE: DNA
<213> ORGANISM: Artificial Sequence
<220> FEATURE:
<223> OTHER INFORMATION: Probe

<400> SEQUENCE: 23
cctatgatga atatag                                              16

<210> SEQ ID NO 24
<211> LENGTH: 16
<212> TYPE: DNA
<213> ORGANISM: Artificial Sequence
<220> FEATURE:
<223> OTHER INFORMATION: Probe

<400> SEQUENCE: 24
aatatgataa tggcct                                              16

<210> SEQ ID NO 25
<211> LENGTH: 15
<212> TYPE: DNA
<213> ORGANISM: Artificial Sequence
<220> FEATURE:
```

-continued

```
<223> OTHER INFORMATION: Probe

<400> SEQUENCE: 25
tacgccacca gctcc                                                    15

<210> SEQ ID NO 26
<211> LENGTH: 10
<212> TYPE: DNA
<213> ORGANISM: Artificial Sequence
<220> FEATURE:
<223> OTHER INFORMATION: Probe

<400> SEQUENCE: 26
acaccgccgg                                                          10

<210> SEQ ID NO 27
<211> LENGTH: 16
<212> TYPE: DNA
<213> ORGANISM: Artificial Sequence
<220> FEATURE:
<223> OTHER INFORMATION: Probe

<400> SEQUENCE: 27
ctctacaagt ataatg                                                   16

<210> SEQ ID NO 28
<211> LENGTH: 21
<212> TYPE: DNA
<213> ORGANISM: Artificial Sequence
<220> FEATURE:
<223> OTHER INFORMATION: Probe

<400> SEQUENCE: 28
gaagatgtta aagtatagag g                                             21

<210> SEQ ID NO 29
<211> LENGTH: 21
<212> TYPE: DNA
<213> ORGANISM: Artificial Sequence
<220> FEATURE:
<223> OTHER INFORMATION: Probe

<400> SEQUENCE: 29
ctagacgtta aagtatagag g                                             21

<210> SEQ ID NO 30
<211> LENGTH: 16
<212> TYPE: DNA
<213> ORGANISM: Artificial Sequence
<220> FEATURE:
<223> OTHER INFORMATION: Probe

<400> SEQUENCE: 30
ctatattcat catagg                                                   16

<210> SEQ ID NO 31
<211> LENGTH: 16
<212> TYPE: DNA
<213> ORGANISM: Artificial Sequence
<220> FEATURE:
<223> OTHER INFORMATION: Probe

<400> SEQUENCE: 31
aggccattat catatt                                                   16
```